US006755782B2

United States Patent
Ogawa

(10) Patent No.: US 6,755,782 B2
(45) Date of Patent: Jun. 29, 2004

(54) ENDOSCOPE DIRT REMOVER

(75) Inventor: Akihisa Ogawa, Hino (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 09/996,267

(22) Filed: Nov. 28, 2001

(65) Prior Publication Data
US 2002/0065450 A1 May 30, 2002

(30) Foreign Application Priority Data

Nov. 29, 2000 (JP) .......................... 2000-363480
Nov. 26, 2001 (JP) .......................... 2001-359072

(51) Int. Cl.⁷ .............................................. A61B 1/00
(52) U.S. Cl. ...................................... 600/127; 600/157
(58) Field of Search ................................ 600/127, 129, 600/155, 157, 175, 114, 121

(56) References Cited

U.S. PATENT DOCUMENTS

| 3,145,249 A | | 8/1964 | Meltzer ........................... 88/1 |
|---|---|---|---|
| 5,382,297 A | * | 1/1995 | Valentine et al. ............. 134/15 |
| 5,392,766 A | | 2/1995 | Masterson et al. ............. 128/4 |
| 5,514,084 A | * | 5/1996 | Fisher ............................ 604/1 |
| 5,518,502 A | * | 5/1996 | Kaplan et al. ............. 600/157 |
| 5,654,824 A | | 8/1997 | Tarr et al. ................... 359/507 |
| 2002/0022762 A1 | * | 2/2002 | Beane et al. ................. 600/101 |

FOREIGN PATENT DOCUMENTS

| JP | 58-61723 | * | 12/1983 |
|---|---|---|---|
| JP | 8-29699 | * | 2/1996 |

* cited by examiner

Primary Examiner—John P. Leubecker
(74) Attorney, Agent, or Firm—Ostrolenk, Faber, Gerb & Soffen, LLP

(57) ABSTRACT

An endoscope dirt remover according to the present invention comprises a tube through which an insert section of an endoscope is inserted, an elastic member coupled with the tube, and a wiper blade coupled with the elastic member at wiping the dirt of the objective lens, at least part of the wiper blade coming into contact with an objective lens of the endoscope and moving on the objective lens together with deformation of the elastic member.

56 Claims, 33 Drawing Sheets

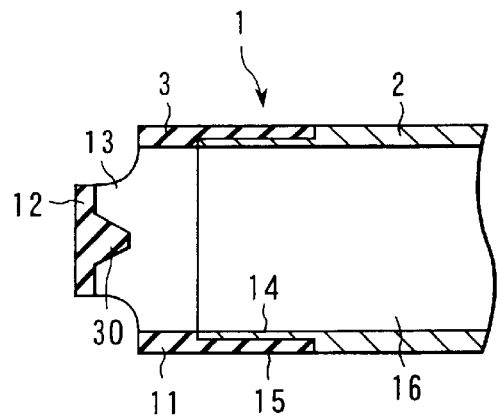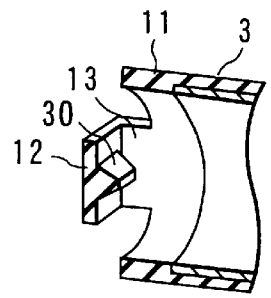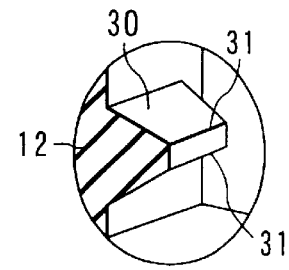
FIG. 3A  FIG. 3B  FIG. 3C
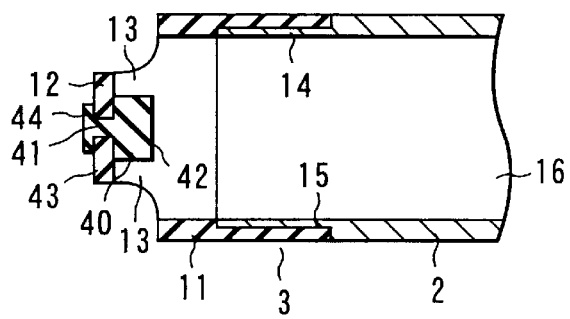
FIG. 4
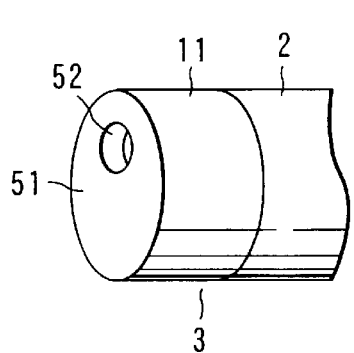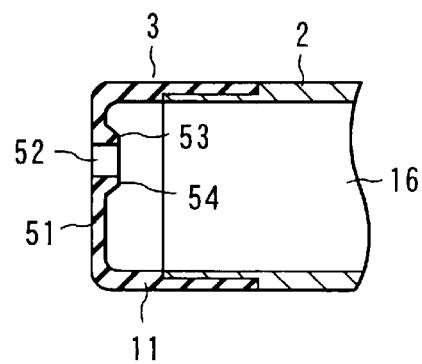
FIG. 5A  FIG. 5B

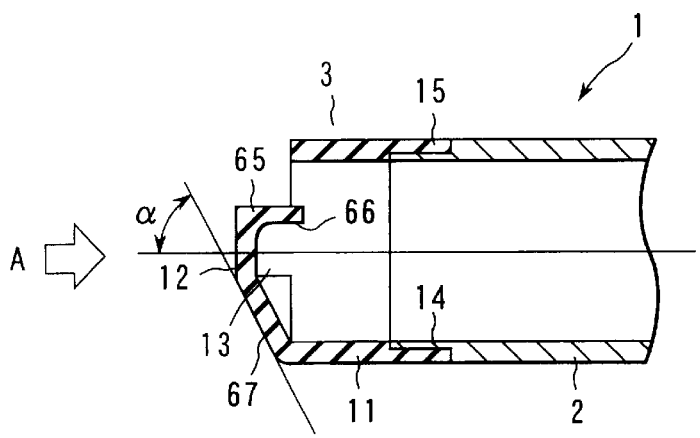
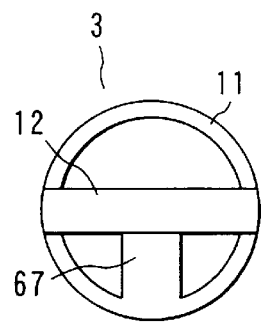
FIG. 8A  FIG. 8B
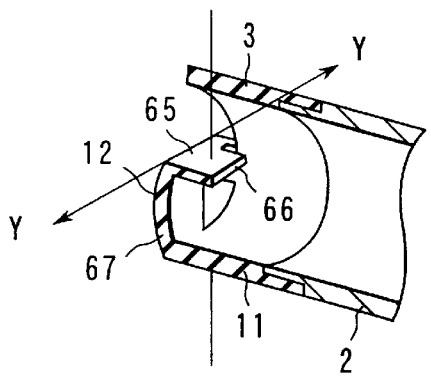
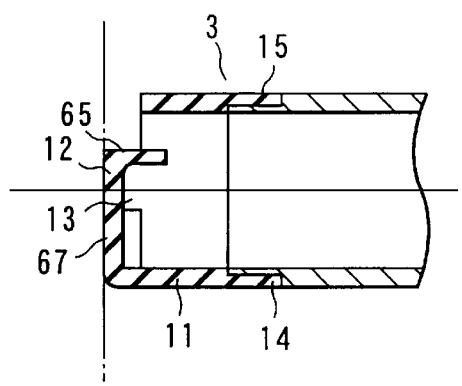
FIG. 8C  FIG. 8D
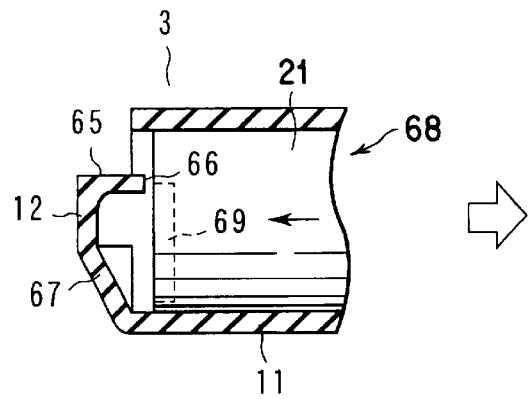
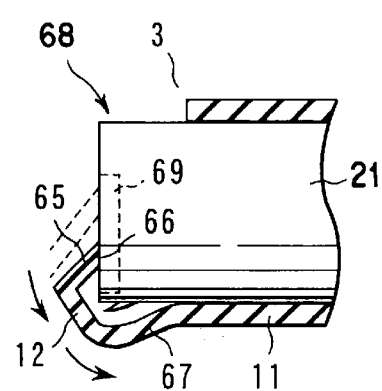
FIG. 9A  FIG. 9B

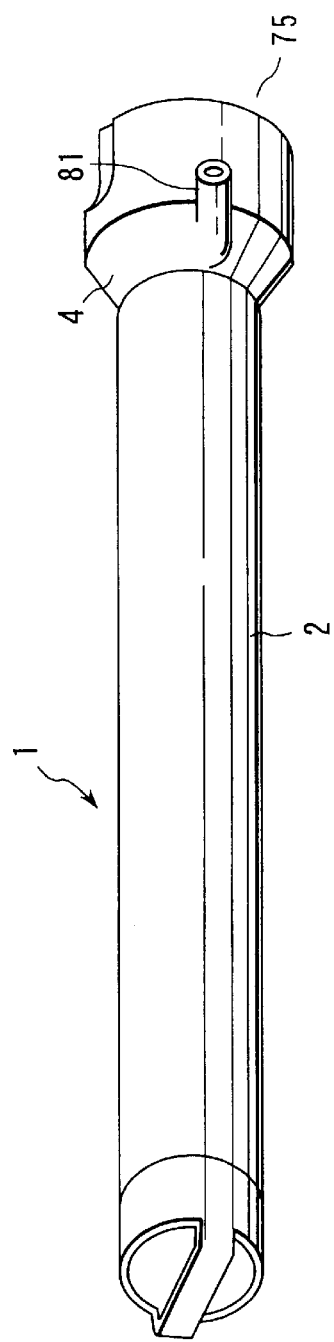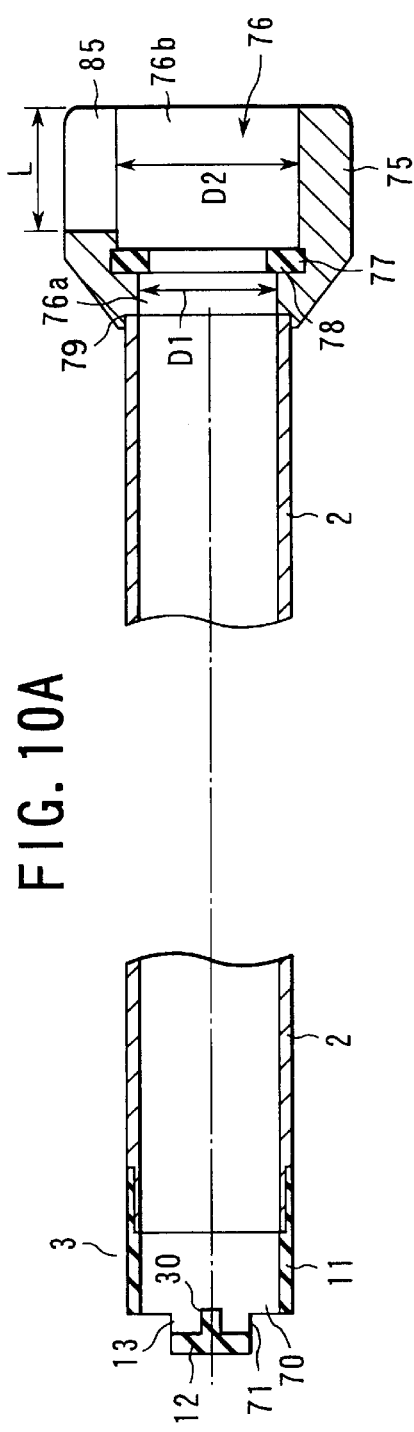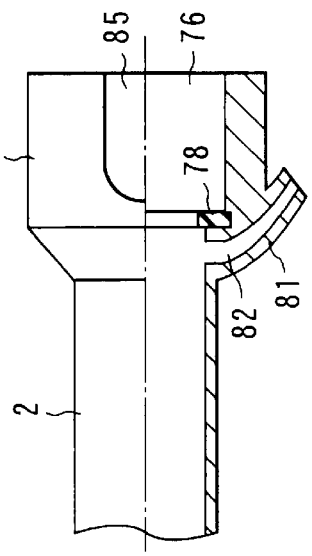
FIG. 10A
FIG. 10B
FIG. 10C

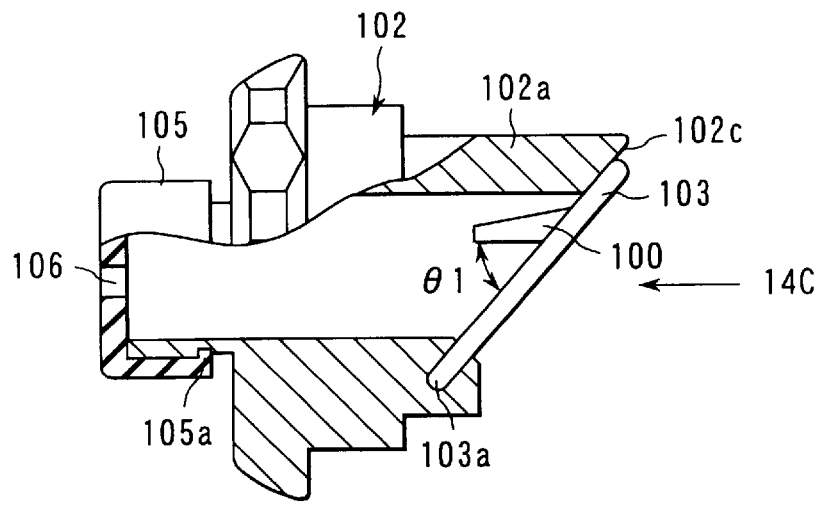
FIG. 14A
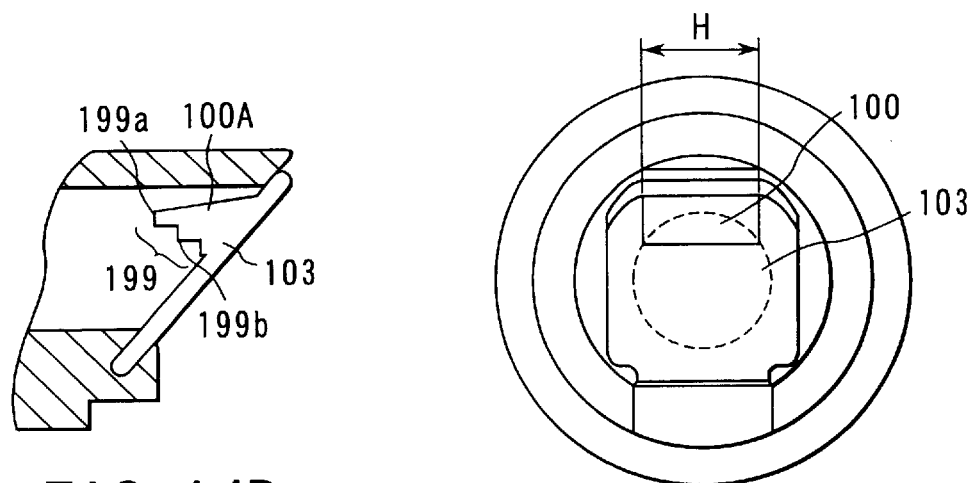
FIG. 14B
FIG. 14C
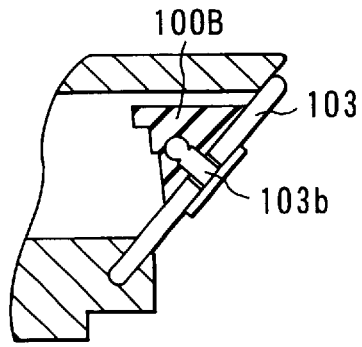
FIG. 14D

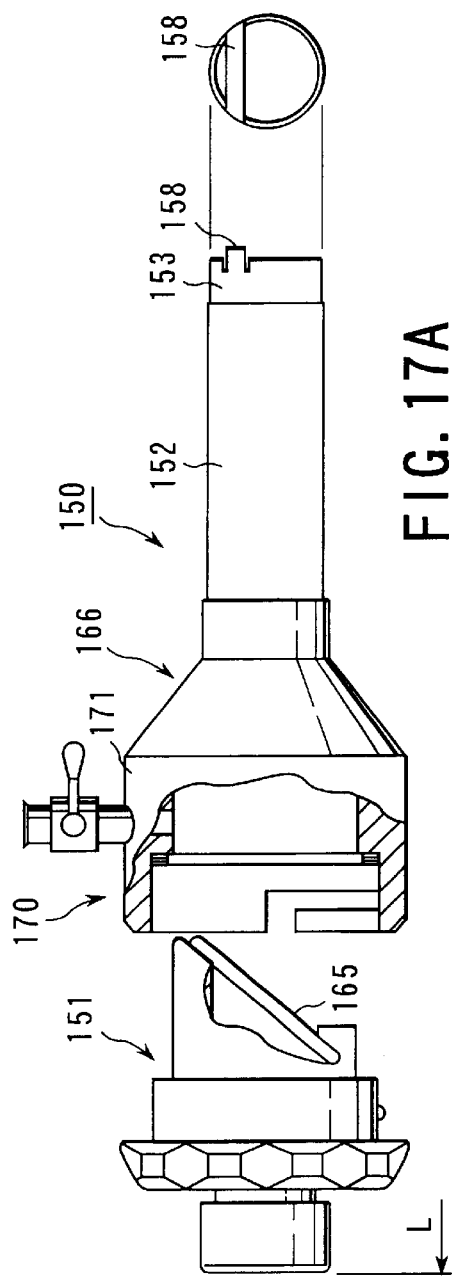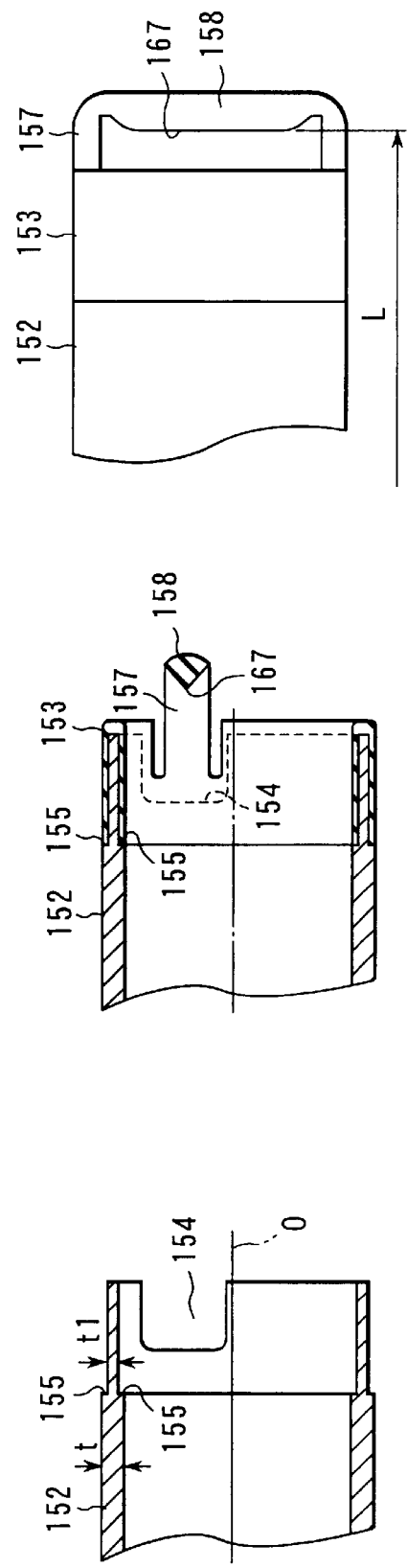

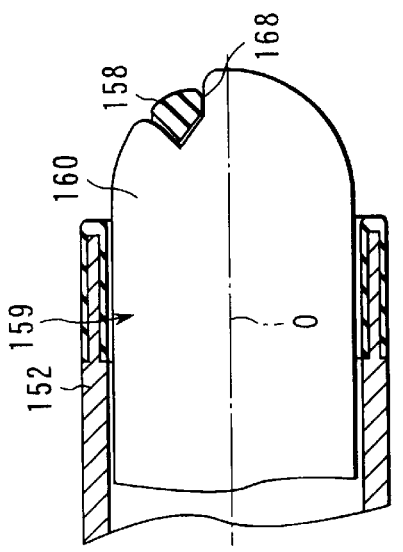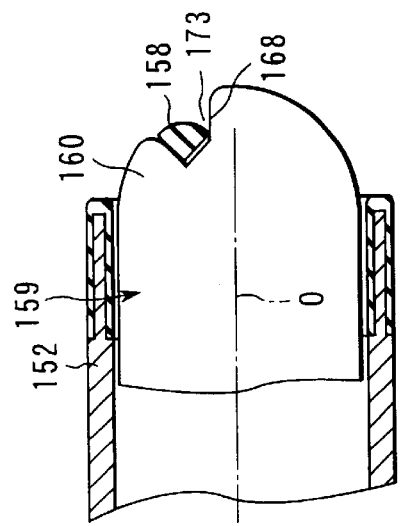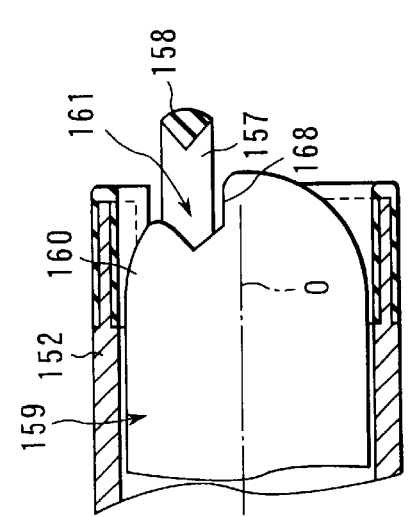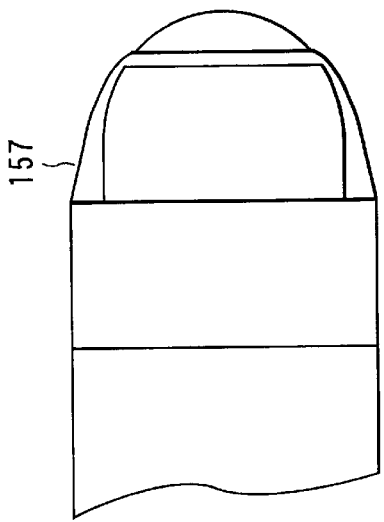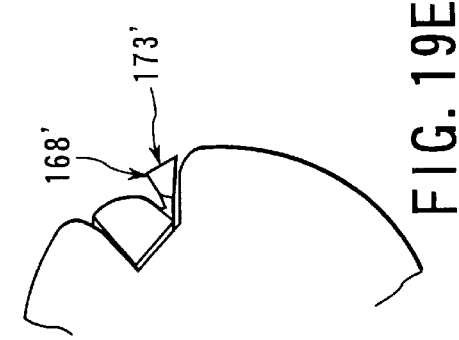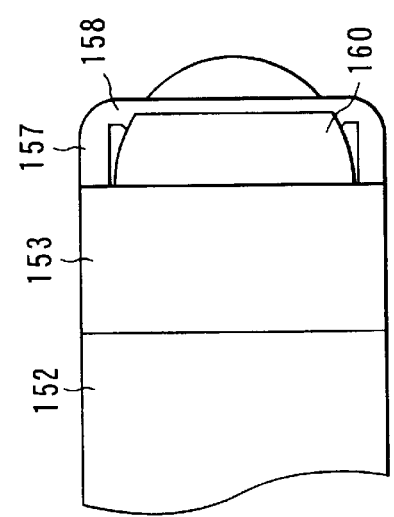

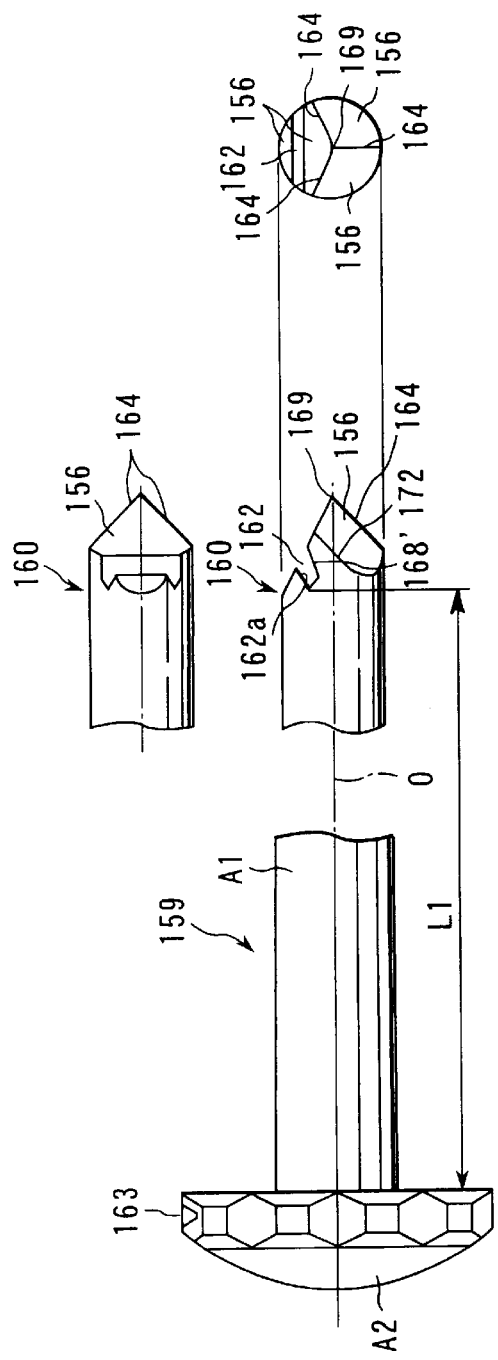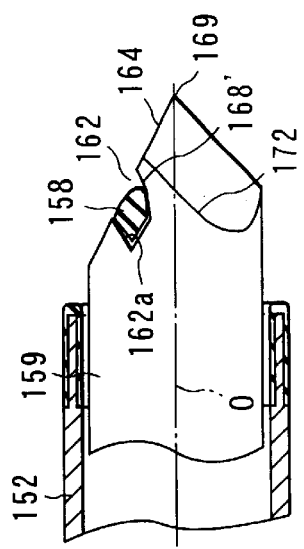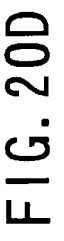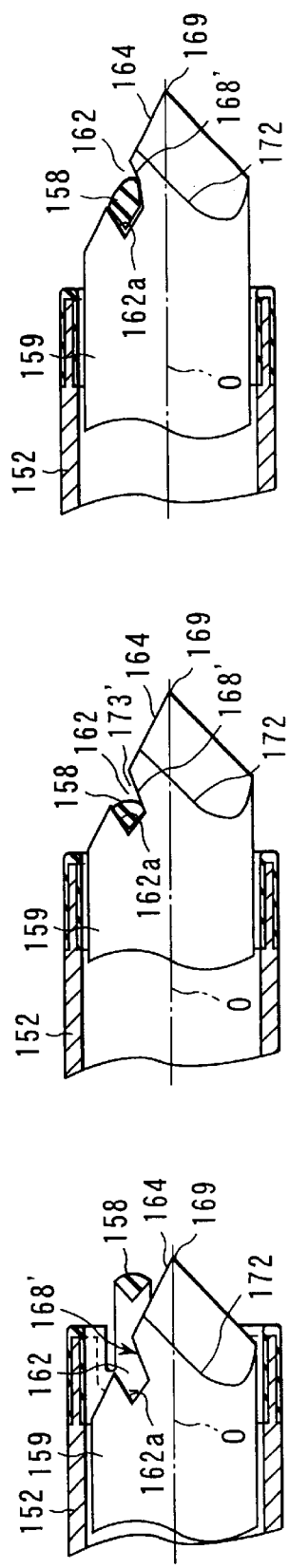

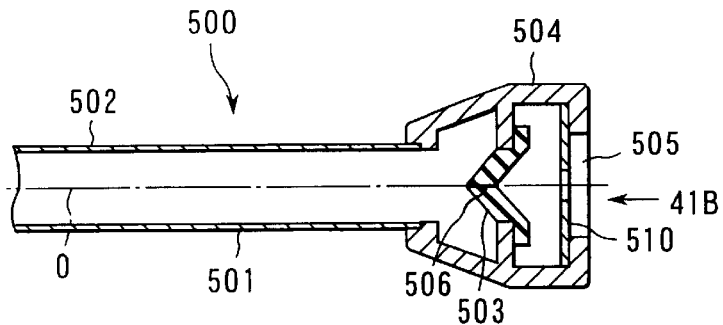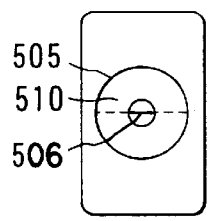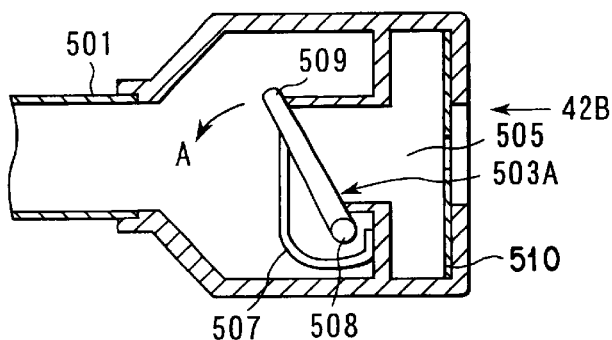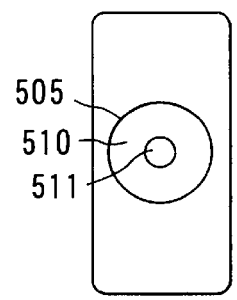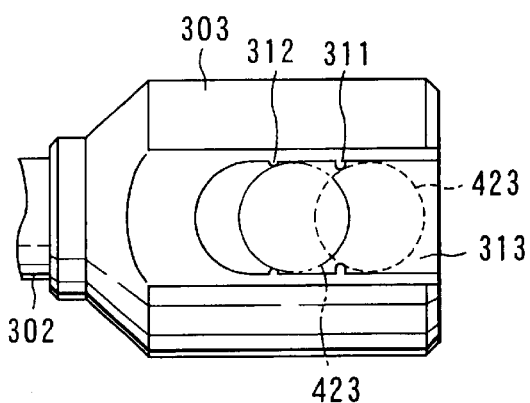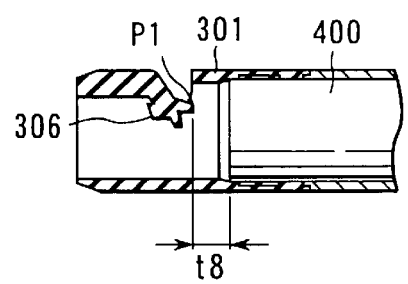
FIG. 41A
FIG. 41B
FIG. 42A
FIG. 42B
FIG. 43
FIG. 44

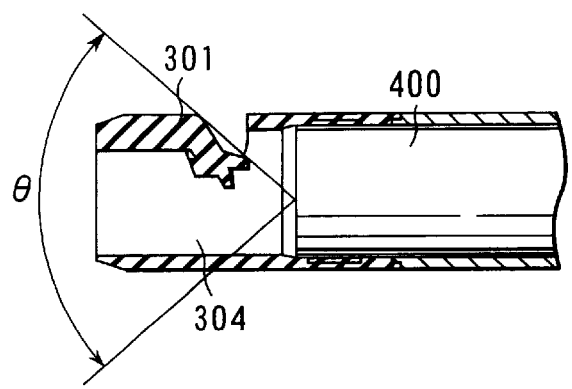
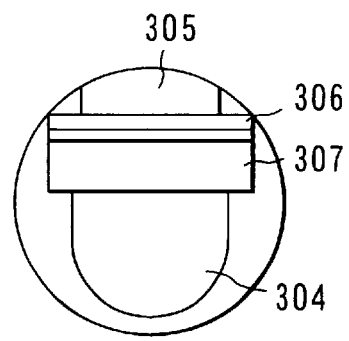
FIG. 45A     FIG. 45B
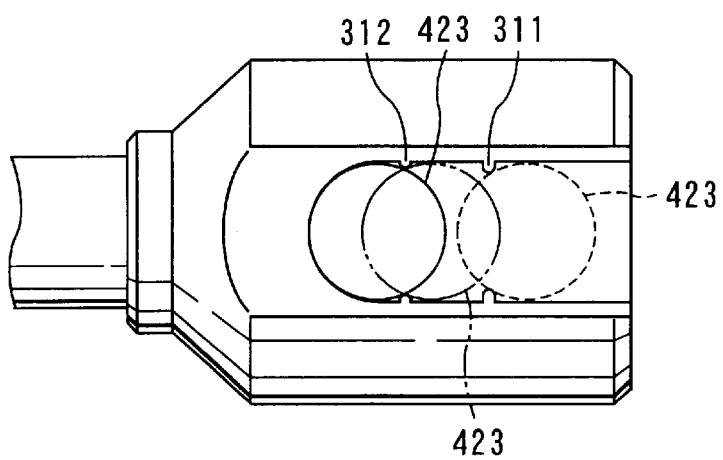
FIG. 46
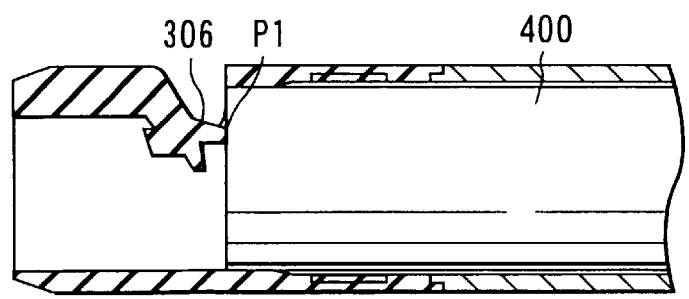
FIG. 47

ENDOSCOPE DIRT REMOVER

CROSS-REFERENCE TO RELATED APPLICATIONS

This application is based upon and claims the benefit of priority from the prior Japanese Patent Application No. 2000-363480, filed Nov. 29, 2000; and No. 2001-359072, filed Nov. 26, 2001, the entire contents of both of which are incorporated herein by reference.

BACKGROUND OF THE INVENTION

Field of the Invention

The present invention relates to an endoscope dirt remover configured to remove the dirt of an endoscope.

Generally, to wash out the dirt adhered to an objective lens face of the endoscope, a means to wash the dirt by jetting a fluid from nozzles provided at the endoscope is known. This makes it possible to wash the dirt adhered to the objective lens face during the condition in which an insert section of the endoscope is inserted into a body. Thus, the dirt adhered to the objective lens face can be removed without removing the insert section of the endoscope from the inside of the body to the outside of the body. Therefore, even when the objective lens face is contaminated during treatment or observation, there is no need to interrupt the operation and to remove the endoscope from the inside of the body to the outside. In addition, there is an advantage that speedy action can be taken against unintentional bleeding or the like, and moreover, a surgeon's stress or an operator's (of the endoscope) stress is alleviated.

In surgical operation under the endoscope, for example, as shown in U.S. Pat. No. 5,400,767, there is proposed another prior art for removing dirt in which the insert section of the endoscope is inserted into a washing sheath; physiological saline or the like as a washing liquid is injected from the frontal side into the washing sheath; the physiological saline or the like is guided to the objective lens face, and the dirt adhered to the objective lens face is washed out.

Further, for example, as in Jpn. UM Appln. KOKAI Publication No. 62-176817 or Jpn. Pat. Appln. KOKAI Publication No. 8-29699, there is provided a technique for removing the dirt adhered to the objective lens face without using the liquid so as to wipe a surface of the objective lens by a wiper. In any of these two publications, the surface of the objective lens is wiped by the wiper, and the dirt is mechanically removed.

When the dirt adhered to the objective lens face of the endoscope is washed away by the jetted fluid from nozzles or in U.S. Pat. No. 5,400,767 in which the insert section of the endoscope is used to be inserted into the washing sheath or the like, slight dirt such as humor or blood can be removed. However, hard dirt such as tissue pieces cannot be easily removed. Even if the dirt has been successfully removed, a state in which wash liquid remains on the surface of the objective lens, i.e., a state in which water is poorly removed is established, and the field of view is often curtailed. Therefore, removing the endoscope from the body to the outside, and wiping the outer surface of the objective lens may be required.

On the other hand, in case of Jpn. UM Appln. KOKAI Publication No. 62-176817 or Jpn. Pat. Appln. KOKAI Publication No. 8-29699, it may be required that a wiping member is abutted and pressed to a predetermined extent, against the objective lens face. A wiping member presented in the previous idea is configured so that only one end of the member is supported by one shaft. Thus, it is difficult to uniformly and sufficiently apply a compression force to the objective lens face at the side of the wiping member that is not supported by the shaft. Therefore, it is difficult to uniformly remove the dirt on the objective lens face. Further, a wiper mechanism is provided at the endoscope itself. Because such a mechanism is incorporated, a configuration of the endoscope becomes complicated, and the equipment itself becomes expensive. Furthermore, this mechanism cannot be used for the endoscope that has been already used in facilities after the mechanism has been provided afterward.

BRIEF SUMMARY OF THE INVENTION

The endoscope dirt remover of the present invention comprises: a tube through which an insert section of an endoscope is inserted; an elastic member coupled with the tube; and a wiper blade coupled with the elastic member and wiping the dirt of the objective lens, at least part of the wiper blade coming into contact with an objective lens of the endoscope and moving on the objective lens together with deformation of the elastic member.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3A is a longitudinal sectional view showing a distal section of an endoscope dirt remover according to a second embodiment of the present invention;

FIG. 3B is a perspective view showing a state in which the distal section of the endoscope dirt remover shown in FIG. 3A is longitudinally cut;

FIG. 3C is an enlarged perspective view of essential portions shown in FIG. 3B

FIG. 4 is a longitudinal sectional view showing a distal section of an endoscope dirt remover according to a third embodiment of the present invention;

FIG. 5A is a perspective view showing a distal section of an endoscope dirt remover according to a fourth embodiment of the present invention;

FIG. 5B is a longitudinal sectional view showing the distal section of the endoscope dirt remover shown in FIG. 5A;

FIG. 8A is a longitudinal sectional view showing a distal section of an endoscope dirt remover according to a sixth embodiment of the present invention;

FIG. 8B is a front view showing the distal section of the endoscope dirt remover shown in FIG. 8A;

FIG. 8C is a perspective view showing a state in which the distal section of the endoscope shown in FIG. 8A is longitudinally cut;

FIG. 8D is a longitudinal sectional view showing a modified distal section of the endoscope dirt remover shown in FIG. 8A;

FIG. 9A is a perspective view showing a state in which the endoscope is inserted into the endoscope dirt remover shown in FIG. 8A;

FIG. 9B is a perspective view of a distal section showing a state in which the endoscope is pushed to the tip end side from the state shown in FIG. 9A;

FIG. 10A is a perspective view showing a distal section of an endoscope dirt remover according to a seventh embodiment of the present invention;

FIG. 10B is a longitudinal sectional view showing the distal section of the endoscope dirt remover shown in FIG. 10A;

FIG. 10C is a longitudinal sectional view showing a grip section of the endoscope dirt remover shown in FIG. 10A;

FIG. 14A is a sectional view showing a configuration of a valve of a distal section of the endoscope dirt remover shown in FIG. 13;

FIG. 14B is a sectional view showing a first modified example of the valve configuration shown in FIG. 14A;

FIG. 14C is a front view seen from the arrow 14C shown in FIG. 14A;

FIG. 14D is a sectional view showing a second modified example of the valve configuration shown in FIG. 13;

FIG. 17A is a side view having a partially sectional view of the endoscope dirt remover which has a dirt removing function at a tip end of an insert section thereof;

FIG. 17B is a sectional view showing a tip end of a tube section when the distal section is not mounted on the tube section of the endoscope dirt remover shown in FIG. 17A;

FIG. 17C is a sectional view showing a state in which the distal section is mounted on the tube section of the endoscope dirt remover shown in FIG. 17A;

FIG. 17D is a plan view when the distal section of the endoscope dirt remover shown in FIG. 17A is seen from the upper side;

FIG. 19A is a sectional view showing a first actuation state when the inner needle shown in FIG. 18 is inserted into the endoscope dirt remover shown in FIG. 17A;

FIG. 19B is a sectional view showing a second actuation state when the inner needle shown in FIG. 18 is inserted into the endoscope dirt remover shown in FIG. 17A;

FIG. 19C is a sectional view showing a third actuation state when the inner needle shown in FIG. 18 is inserted into the endoscope dirt remover shown in FIG. 17A;

FIG. 19D is a plan view in the actuation state shown in FIG. 18;

FIG. 19E is a side view showing a tip end of the second actuation state when an inner needle shown in FIG. 20A is used instead of the inner needle shown in FIG. 18;

FIG. 19F is a plan view in the actuation state shown in FIG. 19C;

FIG. 20A is a side view and a front view of an inner needle according to a modified example of the inner needle shown in FIG. 18;

FIG. 20B is a sectional view showing a first actuation state when the inner needle shown in FIG. 20A is inserted into the endoscope dirt remover shown in FIG. 17A;

FIG. 20C is a sectional view showing a second actuation state when the inner needle shown in FIG. 20A is inserted into the endoscope dirt remover shown in FIG. 17A;

FIG. 20D is a sectional view showing a third actuation state when the inner needle shown in FIG. 20A is inserted into the endoscope dirt remover shown in FIG. 17A;

FIG. 41A is a side sectional view showing an endoscope guide tube;

FIG. 41B is a view seen in the direction indicated by the arrow 41B shown in FIG. 41A;

FIG. 42A is a side sectional view according to a modified example of the endoscope guide tube shown in FIG. 41A;

FIG. 42B is a view seen in the direction indicated by the arrow 42B shown in FIG. 42A;

FIG. 43 is a plan view showing a position of a light guide post relevant to the grip section shown in FIG. 35C;

FIG. 44 is a sectional view showing a state when the endoscope is inserted into the endoscope dirt remover shown in FIG. 35A;

FIG. 45A is a sectional view showing a field of view of the endoscope when the endoscope is inserted into the endoscope dirt remover shown in FIG. 35A;

FIG. 45B is a view showing an endoscope image in the state shown in FIG. 45A;

FIG. 46 is a plan view showing a position of the light guide post relevant to the grip section shown in FIG. 35C;

FIG. 47 is a sectional view showing a state when a first projection section is abutted against a tip end of the endoscope when the endoscope is inserted into the endoscope dirt remover shown in FIG. 35A;

DETAILED DESCRIPTION OF THE INVENTION

Hereinafter, preferred embodiments of the present invention will be described with reference to the accompanying drawings.

Figure 1A:
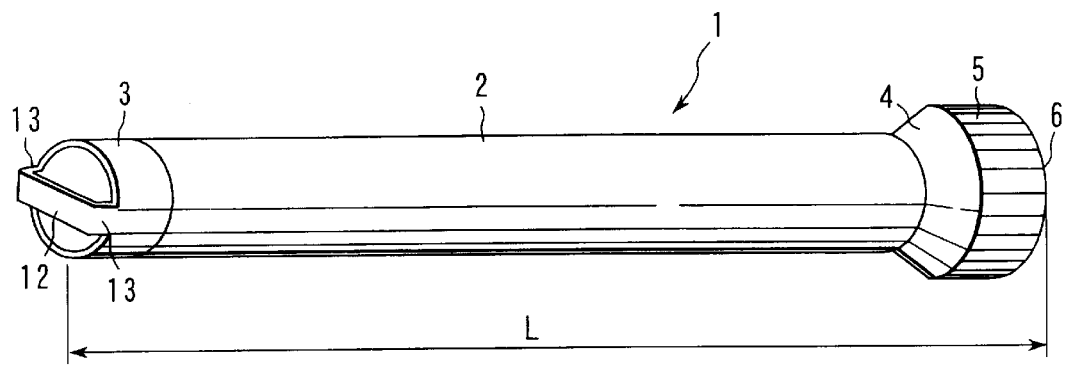
FIG. 1A is a perspective view showing an endoscope dirt remover according to a first embodiment of the present invention.

FIG. 1 and FIG. 2 each show a first embodiment of the present invention. As shown in FIG. 1, an endoscope dirt remover 1 according to the present embodiment comprises a sheath (tube) 2 formed of a straight tube shaped member, wherein a distal section 3 is provided at a tip end of the sheath 2, and a grip section 4 is a frontal section is provided at a proximal end of the sheath 2. The endoscope dirt remover 1 is configured as a tube body capable of inserting an insert section of the endoscope from the grip section 4 into the sheath 2 and distal section 3.

The grip section 4 mounted on atheproximal end of the sheath 2 has an outer diameter greater than that of the sheath 2, and a slip proof irregularity 5 is formed on the surface of the outer periphery of the grip section 4. A through hole (not shown) communicating into the sheath 2 is formed inside of the grip section 4. Further, a proximal end 6 of the grip section 4 is formed as a flat end face that is vertical to a longitudinal axial direction of the dirt remover 1.

Figure 1B:
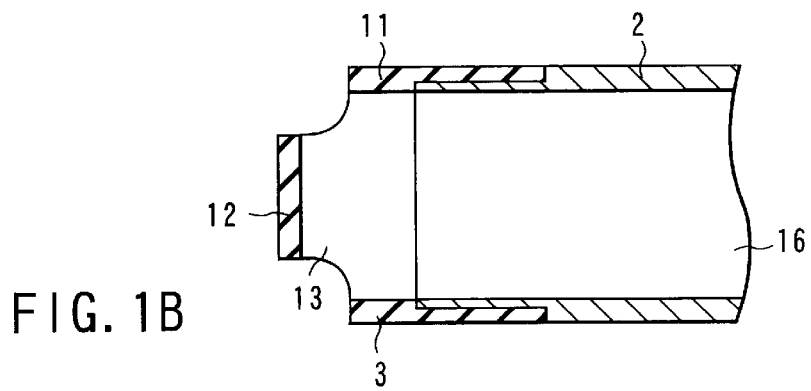
FIG. 1B is a longitudinal sectional view showing a distal section of the endoscope dirt remover shown in FIG. 1A.
Figure 1C:
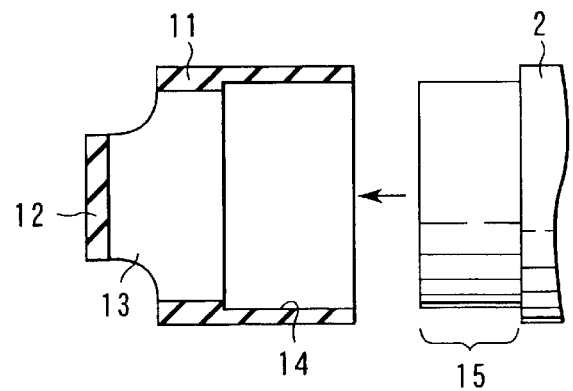
FIG. 1C is an exploded longitudinal sectional view showing the distal section of the endoscope remover shown in FIG. 1A.

At the distal section 3 of the endoscope dirt remover 1, a tube shaped section 11 having an inner hole through which an insert section (in particular, a tip end) of the endoscope can be inserted is provided as a base body. An abutment section (wiper blade) 12 which is a band shaped (strip shaped) member positioned across its opening center is disposed at an opening at the tip end side of the tube shaped section 11. Both ends of the abutment section 12 are coupled to opening end rims at the tip end side of the tube shaped section 11 by each rise section(coupling portion) 13. Further, the abutment section 12 and the rise section 13 are formed as members integrated with the tube shaped section 11. As shown in FIG. 1C, an engagement stepped section 14 is formed on the proximal inner face of the tube shaped section 11. The thus configured distal section 3 is integrally molded of an elastic element having its proper hardness such as silicon or polyurethane, for example. Of course, the quantity of the resilience force is stronger as the hardness of the elastic element is higher. Here, although the abutment section 12 and the rise section 13 are identical to each other in thickness, the thickness of the abutment section 12 may be greater than that of the rise section 13. An element forming the distal section 3 may be transparent.

As shown in FIG. 1C, an engagement step 15 is formed at the outer periphery of the distal section of the sheath 2. As shown in FIG. 1B, the engagement stepped section 14 of the distal section 3 is fixedly bonded to be intimately engaged with this engagement step 15. A method for bonding the sheath 2 with the distal section 3 may not be fixedly bonded, and, for example, the engagement stepped section 14 and the engagement step 15 may be fixedly pressed-in. Further, the sheath 2 and the distal section 3 may be molded integrally by insertion molding.

As described above, the sheath 2 and the distal section 3 are substantially equal to each other in inner diameter and outer diameter when they are connected to each other. A through hole 16 through which the insert section of the endoscope can be inserted is formed of the inside of the sheath 2 and the inside of the distal section 3.

A full length L of the endoscope dirt remover 1 is set to be shorter than an effective length of an insert section 21 (refer to FIG. 2) of the endoscope 20. While a tip end 23 (refer to FIG. 2) of a frontal grip section 22 of the endoscope 20 is abutted against the proximal end 6 of the grip section 4 of the endoscope dirt remover 1, the full length L of the endoscope dirt remover 1 is set to its proper dimensions such that a tip end of the insert section 21 of the endoscope 20 is not excessively protruded from the distal section 3 of the endoscope dirt remover 1. In the present embodiment, a quantity X of which a tip end of the insert section 21 of the endoscope 20 is protruded from the tip end of the endoscope dirt remover 1 is specifically approximately 5 to 20 mm (refer to FIG. 2C). Of course, the full length L of the endoscope dirt remover 1 is greater than that of an endoscope guide tube (not shown).

Now, with reference to FIGS. 2A, 2B and 2C, a description will be given with respect to a method for removing the dirt on an objective lens face of the endoscope during operation using the endoscope dirt remover 1 according to the present embodiment.

The endoscope 20 is of oblique viewing type. That is, a surface of an objective lens 25 disposed at a tip end of the insert section 21 of the endoscope 20 is not vertical to a center axis of the insert section 21, but has a predetermined angle relative of the center axis of the insert section 21. A light guide post 26 is provided at the frontal grip section 22 of the endoscope 20, and this light guide post 26 is connected to a so called light guide cable that transmits light from a light source to the endoscope side.

Figure 2A:
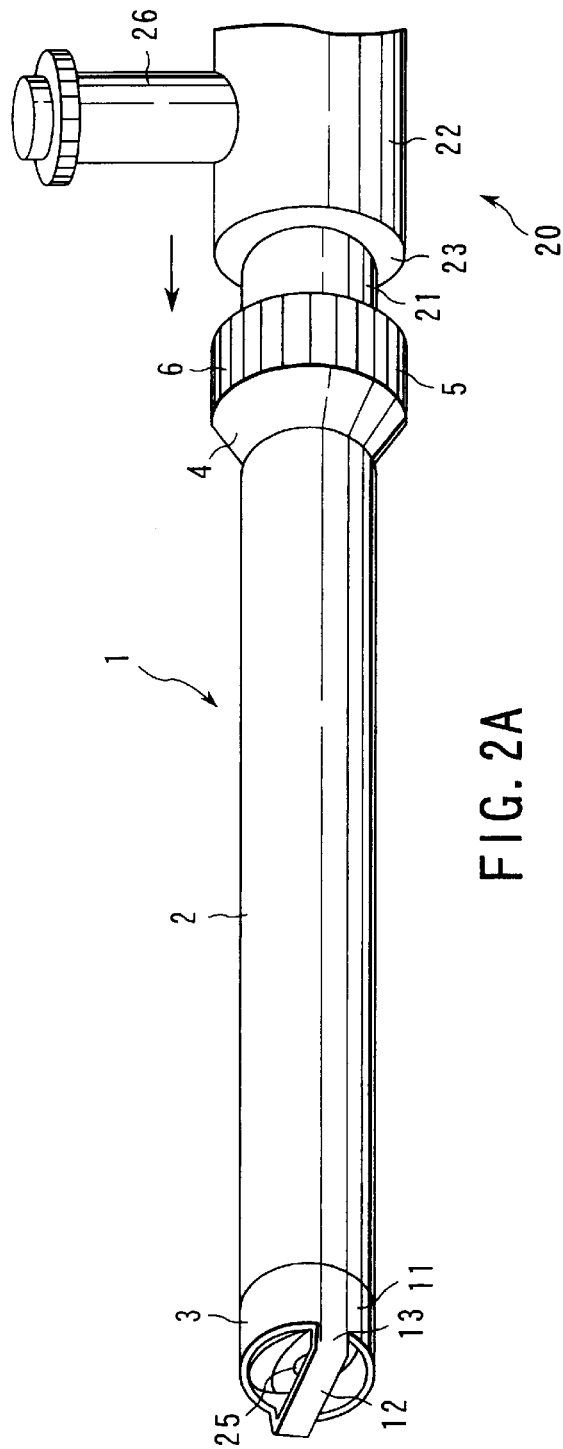
FIG. 2A is a perspective view showing a state in which the endoscope is inserted into the endoscope dirt remover shown in FIG. 1A.

First, before operation, as shown in FIG. 2A, the insert section 21 of the endoscope 20 is inserted into the endoscope dirt remover 1 through a hole of the grip section 4. At this time, the insert section 21 is pushed into the remover 1 at a position at which a surface of the objective lens 25 of the endoscope 20 does not abut against the abutment section 12 of the distal section 3. The endoscope 20 thus combined with the endoscope dirt remover 1 is inserted into the endoscope guide tube (trocar) which is frequently used in endoscope surgical operation, and is introduced into a cavity through this endoscope guide tube. The endoscope guide tube used here is set to dimensions such that the insert section of the endoscope dirt remover 1 can be inserted.

In the state shown in FIG. 2A, a surgeon or an operator of the endoscope can observe an inside state of the cavity or the endoscope guide tube from a gap between the tube shaped section 11 and the abutment section 12 through the endoscope image. Therefore, the surgeon or the operator can recognize through the endoscope image that the distal section 3 of the endoscope dirt remover 1 is introduced into the cavity. When the distal section 3 of the endoscope dirt remover 1 is formed of a transparent element, the surgeon or the operator can observe the inside state of the cavity or the endoscope guide tube through a member of the distal section 3 better.

At a stage at which the endoscope 20 and the endoscope dirt remover 1 are introduced into a cavity through the endoscope guide tube in the state shown in FIG. 2A, the distal section 3 of the endoscope dirt remover 1 is first protruded from the tip end of the endoscope guide tube. When it is verified that the distal section 3 of the endoscope dirt remover 1 protrudes into the cavity through endoscope imaging, the grip section 5 of the endoscope dirt remover 1 is fixedly gripped by hand, and only the insert section 21 of the endoscope 20 is advanced(into the cavity). In this manner, the abutment section 12 abuts against the surface of the objective lens 25 of the insert section 21 of the endoscope 20 (first position: refer to FIG. 2B). At this time, the abutment section 12 and the rise section 13 are made of an elastic member, so that they extend after being compressed on the surface of the objective lens 25. Therefore, even if the surface of the objective lens 25 is inclined, the abutment section 12 and the rise section 13 can come into intimate abutment against the surface of the objective lens 25. Namely, as shown in FIG. 2B, the abutment section 12 extends obliquely while forming a predetermine angle relevant to the center axis of the endoscope dirt remover 1. When the distal section 3 is fixed to be pressed into the tip end of the sheath, the force quantity of press-in and fixing is designed to be greater than a force quantity when the abutment section and the rise section to be pressed on the surface of the objective lens extend. Thus, the distal section 3 is not released from the tip end of the sheath.

When the insert section 21 of the endoscope 20 is further advanced from this state, a resilience force is generated at the abutment section 12 by a contraction action of the elastic element. Due to this resilience force, the abutment section 12 further abuts strongly against the surface of the objective lens 25. That is, by merely advancing the insert section 21 of the endoscope 20, the abutment 12 moves smoothly along the surface of the inclined objective lens 25, as shown in FIG. 2B and FIG. 2C, and wipes the surface of the objective lens 25 in a frictional manner. In this manner, the dirt adhered to the surface of the objective lens 25 is reliably wiped out. Then, when the insert section 21 of the endoscope 20 is advanced, finally, the abutment section 12 slips laterally of the surface of the objective lens 25 off from the field of view, and is retracted on a side face of the insert section 21 of the endoscope 20 (second position: refer to FIG. 2C). Thus, the abutment section 12 is completely retracted out of the field of view through the objective lens 25, thereby making it possible to observe the intra-operative cavity, for example, the inside of the abdominal cavity through the endoscope 20. Of course, the above dirt removing operation can be also carried out intra-operatively.

As described above, the full length L of the endoscope dirt remover 1 is set to be shorter than an effective length of the insert section 21 of the endoscope 20. Further, while the tip end 23 (refer to FIG. 2) of the frontal grip section 22 of the endoscope 20 is abutted against the proximal end 6 of the grip section 4 of the endoscope dirt remover 1, the full length L of the endoscope dirt remover 1 is set to its proper dimensions such that the tip end of the insert section 21 of the endoscope 20 is not excessively protruded from the distal section 3 of the endoscope dirt remover 1. Thus, in a state in which the abutment section 12 is pressed by the insert section 21 of the endoscope 20 and completely retracted out of the field of view through the objective lens 25 as described above (in a state in which the abutment section 12 slips laterally of the objective lens 25), the abutment section is positioned at a lateral site of the insert section 21 of the endoscope 20 so as to be standby in the vicinity of the surface of the objective lens 25 (refer to FIG. 2C).

Figure 2C:
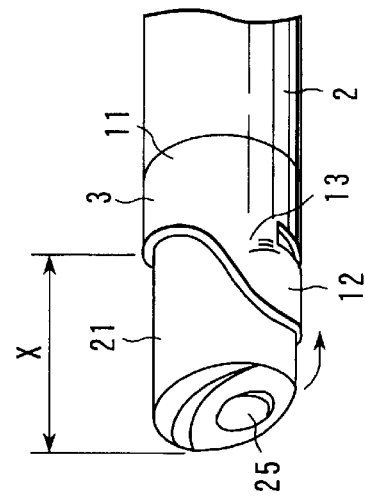
FIG. 2C is a perspective view of the distal section showing an observation state in which the endoscope is further pushed to the tip end side from the state shown in FIG. 2B.
Figure 2B:
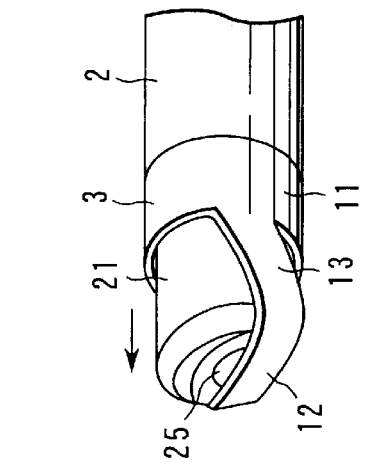
FIG. 2B is a perspective view of a distal section showing a state in which the endoscope is pushed to the tip end side from the state shown in FIG. 2A.

Surgical operation under the endoscope is started in a state shown in FIG. 2C. In this surgical operation under the endoscope, isolation of body tissues, coagulation of bleeding and the like are carried out by using treatment equipment such as electric surgical knife and ultrasonic dissection coagulation apparatus. At this time, smoke, fat components of scorched tissues, water evaporation and the like are scattered in the cavity. These scattered objects adhere to the surface of the objective lens 25 of the endoscope 20, and the surface of the objective lens 25 becomes dirty, which obscures the field of view. Due to a temperature difference between the inside of the cavity and the endoscope 20 itself, condensation forms on the surface of the objective lens 25, and the field of view may be clouded. This makes it impossible to continue operation. Thus, a cleaning operation for recovering the field of view can be carried out in accordance with the procedure below.

First, the grip section 4 of the endoscope dirt remover 1 is gripped, and the endoscope dirt remover 1 is advanced to the tip end side of the insert section 21 of the endoscope 20. In this manner, the abutment section 12 retracted on the side face of the insert section 21 of the endoscope 20 starts sliding in the direction of the objective lens 25. Finally, as shown in FIG. 2A, the abutment section 12 is returned to be positioned frontally of the objective lens 25. The surgeon manipulating the remover 1 can feel such sliding of the abutment section 12 manually through a feeling of resistance. With the feeling of resistance when the abutment section 12 is thus slid, a frictional resistance between the abutment section 12 positioned on the side face of the insert section 21 of the endoscope 20 and the side face of the insert section 21 of the endoscope 20 is greatly related. As described above, the abutment section 12 is standby on the side face of the insert section 21 in the vicinity of the surface of the objective lens 25. When the abutment section 12 is manipulated to be slid for the purpose of cleaning, a distance when the abutment section 12 moves to the objective lens 25 is reduced. Therefore, an acting time of force required for sliding operation of the abutment section 12 can be reduced, and operability can be improved.

As shown in FIG. 2A, while the abutment section 12 is positioned frontally of the objective lens 25, the grip section 4 of the endoscope dirt remover 1 is slid(retracted) to the proximal end side of the insert section 21 of the endoscope 20. In this manner, the abutment section 12 abuts against the surface of the objective lens 25, as shown in FIG. 2B. Then, the abutment section 12 extends so as to be pressed on the surface of the objective lens 25 by its elastic action, and intimately abuts against the surface of the inclined objective lens 25. As described above, the abutment section 12 continuously extends further obliquely while forming a predetermined angle relevant to the center axis of the endoscope dirt remover 1, and finally, is moved laterally of the insert section 21. In a series of such movement processes of the abutment section 12, a friction occurs between the abutment section 12 and the surface of the objective lens 25. Due to this frictional action, the dirt adhered to the surface of the objective lens 25 is moved in a direction in which the abutment section 12 moves, i.e., laterally of the insert section 21. At the abutment section 12, as the quantity of resilience force is stronger, i.e., as a pressure contact force relevant to the surface of the objective lens 25 is stronger, a frictional force between the abutment section 12 and the objective lens 25 increases, and the movement of the dirt can be accelerated.

As described above, when the abutment section 12 is completely retracted out of the field of view through the objective lens 25, and is positioned laterally of the insert section 21 (refer to FIG. 2C), the dirt moves from the surface of the objective lens 25 together with the retracted abutment section 12. Thus, the field of view in a cavity using the endoscope 20 is recovered. In a series of dirt removing operations described above, when a degree of recovering the field of view is low, the dirt removing operation described above may be carried out repeatedly.

As has been described above, in the present embodiment, only the endoscope dirt remover 1 is merely advanced and retracted relevant to the endoscope 20, whereby the dirt of the objective lens 25 can be removed. That is, there is no need to move the endoscope 20 itself, thus making it possible to remove the dirt without displacing the field of view that has been observed. Therefore, after dirt removal, surgical operation under the endoscope can be carried out smoothly. The dirt on the surface of the objective lens 25 of the endoscope 20 can be removed without interrupting surgical operation while the endoscope 20 is inserted into the cavity. Further, since the dirt can be mechanically removed with a simple configuration, unlike another washing means, the dirt of the endoscope can be removed inexpensively and reliably.

In the present embodiment, when the thickness of the abutment section 12 is greater than that of the rise section 13, the expansion/contraction during manipulation concentrates at the rise section 13. Thus, the expansion/contraction change quantity of the abutment section 12 is reduced. If the change quantity of the abutment section 12 is thus reduced, the floating of the abutment section 12 relevant to the surface of the objective lens 25 does not occur, so that the abutment section 12 can be abut evenly against the surface of the objective lens 25. Further, in the present embodiment, the endoscope 20 may be held by a scope holder or the like (not shown) which maintains a position of the endoscope 20.

FIG. 3 shows a second embodiment of the present invention. An endoscope dirt remover 1 according to the present embodiment is identical to the endoscope dirt remover 1 according to the first embodiment described above in basic configuration, and is different in configuration of a distal section 3. Hereinafter, a description will be given by focusing on such a difference from the first embodiment.

As shown in FIG. 3A, the distal section 3 as an elastic member of the endoscope dirt remover 1 according to the present embodiment is composed of: a tube shaped section 11 as a base body having an inner hole through which an endoscope 20 can be inserted; an abutment section (wiper blade) 12 positioned at a tip end side of this tube shaped section 11; and a rise section 13 communicating the tube shaped section 11 with the abutment section 12. These constituent elements are same as those according to the first embodiment described above. However, in the present embodiment, a projection section 30 is provided integrally with an inside face of the abutment section 12. This projection section 30 is smaller in width than the band shaped (strip shaped) abutment section 12, and is positioned substantially at the center in a width direction of the abutment section 12. In addition, the projection section 30 is formed in a configuration which is long and deep in a furrow shape along the longitudinal direction of the abutment section 12. A sectional shape of the projection section 30 is trapezoidal, and may be any other shape such as rectangular and triangular shapes. As shown in FIG. 3C, an edge 31 is provided on the top of the projection section 30.

The projection section 30 is designed so as to be positioned upwardly of the objective lens 25 of the endoscope 20 when the endoscope 20 is mounted on the endoscope dirt remover 1. The lengths of the projection section 30 and the edge 31 are designed to be greater than the diameter of the objective lens 25 so as to completely cross the objective lens 25.

Now, a description will be given with respect to a manipulation method for removing the dirt on the objective lens 25 of the endoscope 20 intra-operatively using the endoscope dirt remover 1 according to the present embodiment. Since this manipulation method is basically identical to that of the first embodiment described above, only a difference will be described here. The following description assumes the procedure carried out after the dirt described in the first embodiment is adhered after the endoscope dirt remover 1 and the endoscope 20 have been introduced into a cavity through the endoscope guide tube.

First, the grip section 4 is gripped by hand, and the endoscope dirt remover 1 is slid(advanced) in the tip end direction of the endoscope 20. In this manner, the abutment section 12 retracted onto the side face of the insert section 21 of the endoscope 20 is pressed by its own elastic resilience force and that of the rise section 13, tube shaped section 11 or the like, and is started to slid toward the objective lens 25. The abutment section 12 is finally positioned frontally of the objective lens 25 of the endoscope 20. Namely, in the cavity, the abutment section 12 is restored to the state shown in FIG. 2A.

During such a sliding operation of the abutment section 12, a feeling of manipulation resistance that the surgeon feels, manually greatly depends on a frictional resistance between the abutment section 12 retracted to the side face of the insert section 21 of the endoscope 20 and the side face of the insert section 21. However, in the present embodiment, as in the first embodiment described above, the abutment section 12 is standby on the side face of the insert section 21 in the vicinity of the objective lens 25. Thus, the distance when the abutment section 12 moves to the objective lens 25 is short, and the frictional resistance can be reduced.

When the abutment section 12 returns to the state shown in FIG. 2A, the grip section 4 of the endoscope dirt remover 1 is slid(retracted) to the proximal end direction of the endoscope 20. In this manner, the edge 31 of the projection section 30 abuts against the surface of the objective lens 25 over its substantially full length. After that, when the remover 1 is further moved to the proximal end side of the endoscope 20, the abutment section 12 made of an elastic element extends to be pressed on the surface of the objective lens 25, and the edge 31 intimately abuts against the inclined objective lens 25. Namely, the edge 31 extends while forming a predetermined angle relevant to the center axis of the endoscope dirt remover 1. At this time, a friction occurs between the objective lens 25 and the edge 31, and the dirt adhered onto the objective lens 25 starts moving in the sliding direction of the edge 31. At the abutment section 12, only the edge 31 comes into contact with the objective lens 25, and thus, a contact area of the abutment section 21 and the objective lens 25 is smaller than that according to the first embodiment. Therefore, non-uniform abutment of the abutment section 12 relevant to the objective lens 25 can be reduced, and the capability of removing the adhered dirt is improved.

As described above, when the endoscope dirt remover 1 is slid to the proximal end direction of the endoscope 20, the abutment section 12 abuts against the objective lens 25 or moves along the inclination of the objective lens 25 due to its own resilience force and the force caused by the contraction action of the element of the rise section 13. Finally, the abutment section 12 is positioned on the side face of the insert section 21 of the endoscope 20. Therefore, the abutment section 12 is retracted out of the field of view through the objective lens 25, resulting in enabling observation in a cavity using the endoscope 20. In a series of dirt removing operations described above, when the degree of recovering the field of view is low, the dirt removing operations(the cleaning operation) described above may be carried out repeatedly. In this case, in the present embodiment, since the projection section 30 is provided at the abutment section 12, and a contact area of the abutment section 12 and the side face of the insert section 21 is small. Therefore, the frictional resistance between the abutment section 12 and inset section 21 is small as compared to the first embodiment and the movement resistance of the abutment section 12 can be reduced. Thus, the surgeon can make cleaning operation described above smoothly.

As has been described above, in the present embodiment as well, as in the first embodiment, only the endoscope dirt remover 1 is merely advanced or retracted relevant to the endoscope 20, whereby the dirt of the objective lens 25 can be removed. That is, there is no need to move the endoscope 20 itself, thus making it possible to remove the dirt without displacing the field of view that has been observed. Therefore, after the dirt removal, surgical operation under the endoscope can be carried out smoothly. In the present embodiment as well, the projection section 30 is provided at the abutment section 12, and the edge 31 is provided at the projection section 30. Thus, the capability of removing the dirt of the objective lens 25 is improved more remarkably than that according to the first embodiment.

FIG. 4 shows a third embodiment of the present invention. An endoscope dirt remover 1 according to the present embodiment is identical to the endoscope dirt remover 1 according to the first embodiment described above in basic configuration, and is different in configuration of a distal section 3. Hereinafter, a description will be given by focusing such a difference from the first embodiment.

As shown in FIG. 4, the distal section 3 of the endoscope dirt remover 1 according to the present embodiment is composed of: a tube shaped section 11 as a base body having an inner hole through which an endoscope 20 can be inserted; an abutment section 12 positioned at the tip end side of this tube shaped section 11; and a rise section 13 communicating the tube shaped section 11 with the abutment section 12. These constituent elements are same as those according to the first embodiment.

In the present embodiment, a projection section 40 that is protruded inwardly of a sheath 2 is provided on an inner face of the abutment section 12. This projection section 40 is formed of an independent member engaged with a mount hole 41 formed at the abutment section 12. This independent member is formed of a porous material or the like having elasticity. Specifically, the member is formed of: an element with its changed hardness such as polyurethane or silicon; a form element obtained by foaming an element identical thereto; or a water absorptive element for absorbing water, for example.

The projection section 40 is smaller in width than the band shaped (strip shaped) abutment section 12, and is positioned substantially at the widthwise center of the abutment section 12. Further, it is desirable that the projection section 40 is formed in a configuration which is long and deep in a furrow shape along the longitudinal direction of the abutment section 12. Thus, the sectional shape of the projection section 40 is rectangle, and may be another shape such as trapezoidal shape or triangular shape.

In the present embodiment, although the abutment section 12, the tube shaped section 11, and the rise section 13 are formed integrally, the projection section 40 is formed independently of these sections 11, 12, and 13. In addition, its surface properties and hardness are different from those of these sections 11, 12, and 13. Of course, a difference between the abutment section 40 and each of the integrally formed sections 11, 12, and 13 may occur only in surface properties or may occur in hardness.

In the present embodiment, the projection section 40 has an edge 42 as in the second embodiment described above. Specifically, the projection section 40 has the edge 42 which abuts against the objective lens 25; a small diameter section 43 engaged with the mount hole 41 of the abutment section 12; and a hook section 44 which prevents escaping of the small diameter section 43 out of the mount hole 41. When the small diameter section 43 of the projection section 40 is engaged with the mount hole 41 of the abutment section 12, the abutment section 12 is sandwiched between the projection section 40 and the hook section 44. Then, the projection section 40 is fixed to prevent slip from the abutment section 12.

The projection section 40 is designed so as to be positioned upwardly of the objective lens 25 of the endoscope 20 when the endoscope 20 is mounted on the endoscope dirt remover 1. The lengths of the projection section 30 and edge 31 are defined to be greater than the diameter of the objective lens 25 so as to completely cross the objective lens 25 (so that the edge 31 can abut against the objective lens 25 over the substantially full length). Although the inner diameter of the mount hole 41 of the abutment section 12 is defined to be smaller than the outer diameter of the hook section 44, the abutment section 12 is formed of an elastic element. Thus, the inner diameter of the mount hole 41 can be elastically increased, making it possible to insert the hook section 44 into the mount hole 41. In the present embodiment, it is preferable that the projection section 40 be fixedly bonded with the abutment section 12. In this case, it is desirable that an adhesive(for example, a silicon based adhesive) have properties capable of maintaining its elastic force even if the adhesive is dried.

Now, a description will be given with respect to a manipulation method for removing the dirt on the objective lens 25 of the endoscope 20 intra-operatively by using the endoscope dirt remover 1 according to the present embodiment. Since this manipulation method is basically identical to that according to the second embodiment described above, only a difference will be described here. The following description assumes the procedures carried out after the dirt as described in the first embodiment is adhered to the objective lens 25 of the endoscope 20 after the endoscope dirt remover 1 and the endoscope 20 have been introduced into the cavity through the endoscope guide tube.

First, the grip section 4 is gripped manually, and the endoscope dirt remover 1 is slid(advanced) in the tip end direction of the endoscope 20. In this manner, the abutment section 12 retracted onto the side face of the insert section 21 of the endoscope 20 in the cavity is pressed by its own elastic resilience force and the elastic resilience force of the rise section 13, tube shaped section 11 or the like, and is started to be slid toward the objective lens 25. The abutment section 12 is finally positioned frontally of the objective lens 25 of the endoscope 20. Namely, in the cavity, the abutment 12 is restored in the state shown in FIG. 2A.

After the abutment section 12 has been restored in the state shown in FIG. 2A, the grip section 4 of the endoscope dirt remover 1 is slid(retracted) in the proximal end direction of the endoscope 20. In this manner, the edge 42 of the projection section 40 abuts against the surface of the objective lens 25 over its substantially full length. After that, when the remover 1 is further moved to the proximal end side of the endoscope 20, the abutment section 12 made of an elastic element extends to be pressed on the surface of the objective lens 25. Then, the edge 42 intimately abuts against the inclined objective lens 25. Namely, the edge 42 extends while forming a predetermined angle relevant to the center axis of the endoscope dirt remover 1. At this time, a friction occurs between the objective lens 25 and the edge 42, and the dirt adhered onto the objective lens 25 starts moving in the sliding direction of the edge 42. At this time, the projection section 40 is formed as a porous member, and thus, the liquid or dirt on the objective lens 25 that interrupts the field of view can be absorbed (the capability of removing the dirt adhered onto the objective lens 25 is improved more remarkably). When the projection section 40 is formed of a water absorptive resin, the force of liquid or dirt absorption is improved more remarkably. If the hardness of the projection section 40 is low, the edge 42 is easily deformed when the projection section 40 abuts against the objective lens 25, making it possible to bring the projection section 40 into intimate abutment against the objective lens 25. When the hardness of the projection section 40 is thus different from that of any other section, or more specifically, if the hardness of the projection section 40 is low, and the hardness of any other portion is high, the projection section 40 can be intimately abutted against the objective lens 25. Thus, non-uniform abutment between the object lens 25 and the abutment section 12 can be reduced. The orientation or force quantity when the abutment section 12 is pressed to the objective lens 25 is same as those according to the embodiment described above.

If the endoscope dirt remover 1 is further slid(retracted) to the proximal end side from the above state, the abutment section 12 tends to be restored in its original position due to the contraction action of its element. As a result, the abutment section 12 moves along the inclination on the objective lens 25, comes out of the field of view through the objective lens 25, and is retracted to the side part of the endoscope 20. At this time, the dirt is removed from the top of the objective lens 25 together with the retracted abutment section 12 and the projection section 40, and the field of view is recovered. When the abutment section 12 is completely retracted out of the field of view through the objective lens 25, the inside of the cavity can be observed by the endoscope 20.

When the projection section 40 is moved and retracted to the side part of the endoscope 20, the projection section 40 is crashed properly between the abutment section 12 and the side face of the endoscope 20. After the projection section 40 that is a porous member has been crashed, the liquid contained therein is pushed outside of the projection section 40. Therefore, when the projection section 40 has moved again onto the objective lens 25, no liquid always remains in the projection section 40. The liquid on the objective lens 25 that interrupt the field of view can be absorbed by the projection section 40 with an always proper absorption rate.

As described above, if the projection section 40 and the abutment section 12 are fixed to each other by adhesive having properties capable of maintaining resilience force even if dried, the abutment section 12 and the projection section 40 are properly expanded/contracted in the dirt removing operation described above. This can prevent cracks of the adhesive section, and can maintain functions inherit to both of the elements 12 and 40.

In the present embodiment, the projection section 40 is thus different from each of the integrally formed sections 11, 12, and 13 in surface properties and hardness, thus making it possible to improve the capability of removing the dirt of the objective lens 25 more remarkably.

FIG. 5 and FIG. 6 each show a fourth embodiment of the present invention. An endoscope dirt remover 1 according to the present embodiment is identical to the endoscope dirt remover 1 according to the first embodiment described above in basic configuration, and is different in configuration of a distal section 3. Hereinafter, a description will be given by focusing such a difference from the first embodiment.

As shown in FIG. 5, a tip end face of the tube shaped section 11 of the distal section 3 of the endoscope dirt remover 1 is covered with a tip end wall section 51, and a through hole 52 is formed at the tip end wall section 51. Further, the hole 52 is arranged eccentrically at the upper side of the tip end wall section 51. As shown in FIG. 5B, a projection part 53 is provided all around an end rim of the hole 52 positioned at the through hole 16, and an edge 54 is formed at the protruded tip end of the projection part 53.

As shown in FIG. 6, a tip end face of the insert section 21 of the endoscope 20 is inclined including the objective lens 25. A tip end part 56 which is the most protrusive at the tip end face of the insert section 21 is positioned corresponding to the hole 52 formed at the distal section 3 of the endoscope dirt remover 1 when the endoscope 20 is inserted into the endoscope dirt remover 1. Namely, the hole 52 is formed at the tip end wall section 51 so as to be positioned in substantial correspondence with the protruded tip end part 56. Therefore, if the insert section 21 of the endoscope 20 is inserted into the endoscope dirt remover 1, the protrusive tip end part 56 of the insert section 21 is positioned facing to the hole 52 of the endoscope dirt remover 1.

The distal section 3 of the endoscope dirt remover 1 may be integrally formed of a transparent element, including a portion of the tip end wall section 51, and it is needless to say that it is made of an elastic element having its proper hardness. Of course, only the portion of the tip end wall section 51 may be formed so as to be transparent.

Now, a description will be given with respect to a manipulation method for removing the dirt onto the objective lens 25 of the endoscope 20 intra-operatively by using the endoscope dirt remover 1 according to the present embodiment. This manipulation method is basically identical to that according to the third embodiment described above. Only a difference will be described here. Prior to operation, the insert section 21 of the endoscope 20 is inserted into the endoscope dirt remover 1 through the hole of the grip section 4. Here, the tip end part 56 of the endoscope does not come into contact with the tip end wall section 51 (not shown). In this state, the tip end part is inserted into the endoscope guide tube, and is inserted into the abdominal cavity. When the distal wall section 51 is made of a transparent material, it is possible to observe the inside of the endoscope guide tube and the inside of the abdominal cavity through the wall section 51 by the endoscope 20.

Figure 6A:
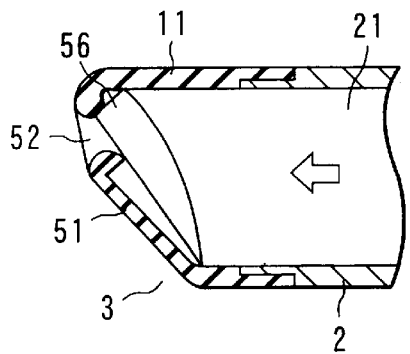
FIG. 6A is a perspective view showing a state in which the endoscope is inserted into the endoscope dirt remover shown in FIG. 5A.
Figure 6B:
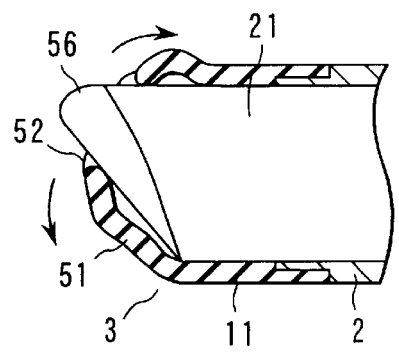
FIG. 6B is a perspective view of a distal section showing a state in which the endoscope is pushed to the tip end side from the state shown in FIG. 6A.
Figure 6C:
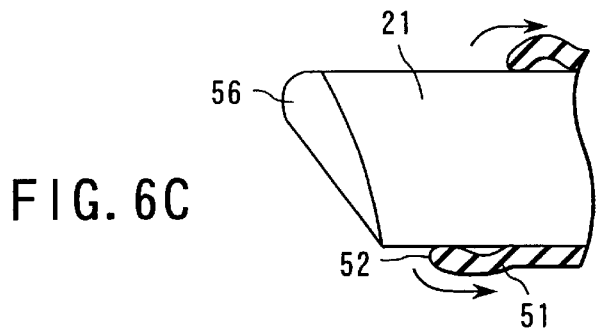
FIG. 6C is a perspective view of a distal section showing an observation state in which the endoscope is further pushed to the tip end side from the state shown in FIG. 6B.

First, after the endoscope 20 has been introduced into the cavity, the grip section 4 of the endoscope dirt remover 1 is gripped, and only the endoscope 20 is advanced into the peritoneal cavity in order to clearly observe the inside of the cavity. Then, the protruded tip end part 56 of the insert section 21 of the endoscope 20 abuts against the projection part 53 around the hole 52, as shown in FIG. 6A. When only the endoscope 20 is further advanced, the tip end part 56 is exposed to the inside of the cavity from the distal section 3 of the endoscope dirt remover 1 while expanding the hole 52 and projection part 53, as shown in FIG. 6B and FIG. 6C. Therefore, the inside of the cavity can be observed by the endoscope 20.

The tip end part 56 of the endoscope 20 is integrally molded with an elastic member. When the tip end part 56 passes through the hole 52, the hole 52 or projection part 53 expands without breakage. A peripheral rim portion of the expanded hole 52 comes into substantially intimate contact with an outer periphery face of the insert section 21 of the endoscope 20. In this state, surgical treatment under the endoscope is carried out.

The procedures after the dirt described above in the first embodiment has been adhered to the objective lens 25 intra-operatively will be described below.

First, the grip section 4 of the endoscope dirt remover 1 is gripped, and the endoscope dirt remover 1 is slid (advanced) in the tip end direction of the endoscope 20. Then, the tip end wall section 51 and tube shaped section 11 at a site of the tip end side of the endoscope 20 start moving to the objective lens 25, as shown in FIG. 6B. When the endoscope dirt remover 1 is further advanced in the tip end direction, the projection part 53 is positioned frontally of the objective lens 25 and the hole 52 and projection part 53 are restored in their original sizes, as shown in FIG. 6A. In this state, the endoscope dirt remover 1 is slid(retracted) in the proximal end direction of the endoscope 20. In this manner, the protrusive tip end part 56 of the endoscope 20 abuts against a rim of the hole 52, as shown in FIG. 6A and FIG. 6B. If sliding is further continued, the hole 52 is expanded, and the tip end part 56 of the endoscope 20 is exposed to the inside of the cavity. At this time, an edge 54 of the projection part 53 provided at the full inward periphery of the hole 52 is more intimately abutted against the objective lens 25 due to the expansion of the hole 52. Namely, the edge 54 extends while forming a predetermined angle relevant to the center axis of the endoscope dirt remover 1. Due to a friction caused between the objective lens 25 and the edge 54 in this duration, the dirt adhered onto the objective lens 25 starts moving in the sliding direction of the edge 54. If the endoscope dirt remover 1 is further slid (retracted) in the proximal end direction of the endoscope 20, an inner diameter of the hole 52 is expanded to so that the inner diameter of the hole 52 is equal to the outer diameter of the tip end part 56 of the endoscope 20. Thus, as shown in FIG. 6C, the distal section 3 of the endoscope dirt remover 1 is retracted to the side part of the endoscope 20 out of the field of view through the objective lens face 25. At this time, the dirt is removed from the top of the objective lens 25 at a lateral site of the insert section 21 of the endoscope 20 together with the retracted projection part 53, and the field of view of the endoscope 20 is recovered, making it possible to observe the inside of the cavity by the endoscope 20 again. When the degree of recovering the field of view during this dirt removing operation is low, dirt removing operation is carried out repeatedly as in the embodiment described above.

According to the present embodiment, the shape of the distal section 3 of the endoscope dirt remover 1 can be simplified, and thus, the endoscope dirt remover 1 can be provided inexpensively.

Figure 7:
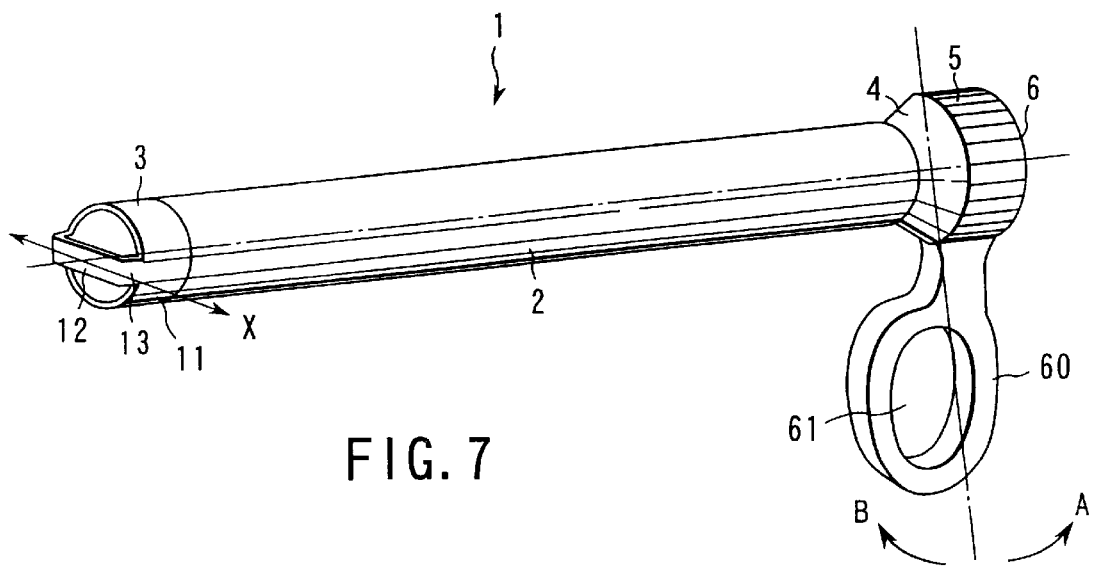
FIG. 7 is a perspective view showing an endoscope dirt remover according to a fifth embodiment of the present invention.

FIG. 7 shows a fifth embodiment of the present invention. An endoscope dirt remover 1 according to the present embodiment is identical to the endoscope dirt remover 1 according to the first embodiment described above in basic configuration, and is different in configuration of a grip section 4. Hereinafter, a description will be given by focusing on such a difference from the first embodiment.

As shown in FIG. 7, a handle 60 is additionally provided at the grip section 4 of the endoscope dirt remover 1 according to the present embodiment. The handle 60 extends downwardly while forming a substantially right angle relevant to the center axis of the endoscope dirt remover 1. However, during endoscope insertion, if the endoscope 20 and the handle 60 do not interfere with each other, the handle 60 may extend toward the direction indicated by the arrow A in the figure. If a patient's body part and the handle 60 do not interfere with each other, the handle 60 may extend in the direction indicated by the arrow B in the figure. The handle 6 extends while forming a substantially right angle relevant to the longitudinal direction X of the abutment section 12 of the distal section 3. However, the handle 60 is not limited to this shape. A finger hook hole 61 is formed at the distal section of the handle 60.

Now, a description will be given with respect to a manipulation method for removing the dirt on an objective lens face of an endoscope by using the endoscope dirt remover 1 according to the present embodiment. The manipulation method according to the present embodiment is identical to that according to the first embodiment described above, and is different only in that the handle 60 is provided. Hereinafter, only the associated difference will be described.

If the dirt is adhered to the objective lens 25 of the endoscope 20 intra-operatively, the surgeon hooks fingers gripping the endoscope 20 on the handle 60. Then, the fingers hooked by the handle 60 is moved in the tip end direction or proximal end direction of the endoscope 20, whereby the endoscope dirt remover 1 can be advanced/retracted in the axial direction of the endoscope 20. When the handle 60 is thus provided, the endoscope dirt remover 1 can be manipulated by one hand, and the operability of the endoscope dirt remover 1 and the endoscope 20 is improved.

FIG. 8 and FIG. 9 each show a sixth embodiment of the present invention. An endoscope dirt remover 1 according to the present embodiment is identical to the endoscope dirt remover 1 according to the first or second embodiment described above in basic configuration, and is different in configuration of a distal section 3. Further, a combinable endoscope 68 is added. Now, the endoscope 68 will be described here. The endoscope 68 is called a so-called forward (direct)-viewing endoscope such that a surface of an objective lens 69 thereof is orthogonal to a center axis of an insert section of the endoscope 68. The other constituent elements are similar to those of the endoscope 20. Hereinafter, a description will be given by focusing on such a difference from the first or second embodiment.

FIG. 8 shows a configuration of the distal section 3 of the endoscope dirt remover 1 according to the present embodiment. In the present embodiment, as in the second embodiment, the distal section 3 comprises: a tube shaped section 11; a band shaped abutment section having a face orthogonal to the center axis of the tube shaped section 11; and a rise section 13 which couples the abutment section 12 with the tube shaped section 11. The material and hardness or the like of these sections 11, 12, and 13 are identical to those according to the first embodiment or second embodiment. Of course, at least part of these sections 11, 12, and 13 may be formed of a transparent elastic member.

A projection 65 is integrally provided at an upper end rim of the abutment section 12 so as to be protruded toward an objective lens 69 of an endoscope 68. This projection 65 is formed in a rectangular sectional shape, as shown in FIG. 8A. However, the sectional shape of the projection 65 may be trapezoidal or may be triangular. Further, the protrusive portion 65 is deep, as shown in FIG. 8C, and is long along the longitudinal direction Y of the abutment section 12. Moreover, an edge section 66 is formed at the protrusive tip end of the projection 65. Furthermore, the projection 65 is positioned upwardly of the objective lens 69 of the endoscope 68, and is formed so that the edge section 66 can abut against the objective lens 69 over its full width. It is desired that the abutment 12 is thicker than the rise section 13 and an auxiliary plate 67.

An auxiliary plate 67 is provided at the lower rim of the abutment section 12 to be in contiguous contact with the lower rim. This auxiliary plate 67 extends in a direction orthogonal to the longitudinal direction of the abutment section 12, and extends obliquely downwardly while forming an arbitrary angle a relevant to the center axis of the endoscope dirt remover 1, as shown in FIG. 8A. In addition, the auxiliary plate 67 is arranged over the opening lower end rim of the tube shaped section 11 from the lower rim of the abutment section 12, and is integrally coupled with the distal section 3. The auxiliary plate 67 may extend while forming a right angle relevant to the center axis of the endoscope dirt remover 1, as shown in FIG. 8D. The distal section 3 may be made of a transparent material including this auxiliary plate 67.

Now, a method using the endoscope dirt remover 1 according to the present embodiment will be described here.

The procedures before introducing the endoscope dirt remover 1 and the endoscope 68 into the cavity through the endoscope guide tube are identical to those according to the first, or second embodiment.

After it is verified that the distal section 3 of the endoscope dirt remover 1 has been completely introduced into the cavity from the tip end of the endoscope guide tube, the grip section 4 of the endoscope dirt remover 1 is gripped, and only the endoscope 68 is pushed into the cavity. In the case, if the distal section 3 is made of transparent material, it may be easy to identify whether the distal section 3 is inserted into the cavity. When only the endoscope 68 is pushed, as shown in FIG. 9A, the upward site of an objective lens 69 abuts against the edge section 66 of the projection 65. After that, when only the endoscope 68 is further advanced into the cavity, the projection 65, the abutment section 12, the rise section 13, and the auxiliary plate 57 are deformed to be pressed by the endoscope 68. Then, the auxiliary plate 67 and the abutment section 12 including the edge section 66 of the projection 65 slip on the objective lens 69 along the direction of the arrow (downwardly shown in the figure) shown in FIG. 9B, and moves laterally of the endoscope 68. Finally, all of the projection 65, the abutment section 12, the rise section 13, and the auxiliary plate 67 are completely retracted from the top of the objective lens 69 of the endoscope 68 and positioned on the side surface of the endoscope 68, making it possible to observe the inside of the cavity caused by the endoscope 68. The abutment section 12 is moved along the direction of the arrow shown in FIG. 9B due to the effect of the auxiliary plate 67. Such movement will be described below.

When the surface of the objective lens 69 of the endoscope 68 is contaminated intra-operatively, the dirt is removed in the same manner as that in the first embodiment or second embodiment. That is, the endoscope dirt remover 1 is advanced (slid) toward the tip end side relevant to the endoscope 68. In this manner, the projection 65, the abutment section 12, and the auxiliary plate 67 are moved from the side surface of the endoscope 68 to the tip end of the endoscope 68. Thus, these portions (12,65,67) are deformed in reversed order as described above, and is restored in the original state shown in FIG. 9A. At this time, the edge section 66 at the projection 65 of the endoscope dirt remover 1 sufficiently rubs the surface of the objective lens 69, and thus, the dirt of the objective lens 69 of the endoscope 68 is scratched. Thus, the dirty is moved from the surface of the objective lens 69 to the other surface. In this case, a cleaning effect is improved by slowly moving the edge section 66.

Next, only the endoscope dirt remover 1 is pulled toward the proximal end side of the inset section of the endoscope 68. In this manner, as shown in FIG. 9A, the projection 65 is strongly pressed onto the upward site of the objective Lens 69, the auxiliary plate 67 is expanded. At this time, the compression force of the auxiliary plate 67 is acted as well. This contraction effect strongly works in the direction indicated by the arrow shown in FIG. 9B. Then, the abutment section 12 is moved in a direction of the arrow shown in FIG. 9B in which the abutment section is retracted from the top of the objective lens 69. By a series of these operations, the edge section 66 of the projection 65 is moved on the objective lens 69, and the remaining dirt is scratched and removed. In this case, if the thickness of the abutment section 12 is larger than that of the rise section 13 and the auxiliary plate 67, the abutment section 12 isn't deformed easily. Thus, the projection 65 can uniformly abut against the surface of the objective lens 69. Therefore, a cleaning effect is improved. Finally, the abutment section 12 and the projection 65 move to a position at which they are retracted from the objective lens 69, i.e. move to the side surface of the endoscope 68, making it possible to observe the inside of the cavity caused by the endoscope 68 again. In this case, if the endoscope dirt remover according to the present embodiment is combined with the oblique viewing endoscope, the dirt on the objective lens 69 can be removed beyond question.

In the present embodiment, although actuation at the distal section 3 for removing the dirt on the objective lens 69 is substantially same as that according to the second embodiment, the compression force of the auxiliary plate 67 is different from that according to the second embodiment in that the compression force of the auxiliary plate 67 contributes to retracting movement of the abutment section 12. That is, at the endoscope dirt remover 1 according to the present embodiment the abutment section 12 and the tube shaped section 11 are coupled with each other by the auxiliary plate 67 and the rise section 13. Even without help for the inclination degree of the objective lens of the endoscope, the projection 65 can be moved to be retracted from a first position to a second lateral position on the objective lens 69. Thus, the present invention can be applied to the endoscope 68 of so called direct viewing type in which the objective lens 69 is orthogonal to the center axis of the endoscope.

Figure 11:
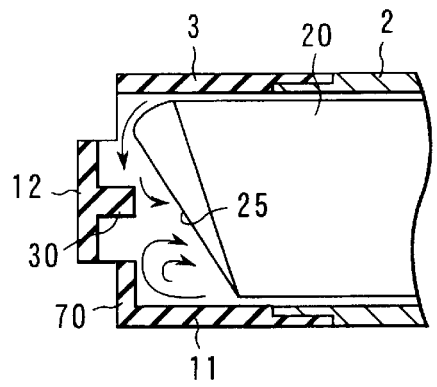
FIG. 11 is a longitudinal sectional view of a distal section showing actuation of the endoscope dirt remover shown in FIG. 10A.
Figure 12A:
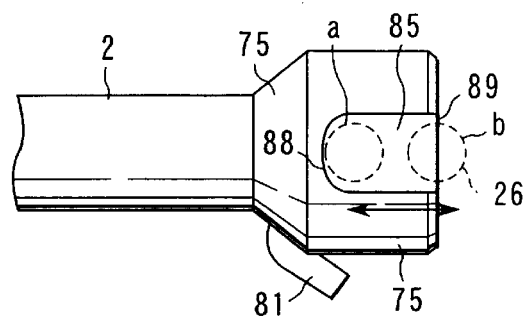
FIG. 12A is a plan view showing the grip section of the endoscope dirt remover shown in FIG. 10A.

FIG. 10 to FIG. 12 each shows a seventh embodiment of the present invention. An endoscope dirt remover according to the present embodiment is identical to the endoscope dirt remover 1 according to the second embodiment described above in basic configuration.

FIG. 10 shows the endoscope dirt remover 1 according to the present embodiment. As shown in the figure, the endoscope dirt remover 1 comprises: a sheath 2 formed of a straight line shaped tube body; a distal section 3; and a grip section 4 like in the second embodiment described above.

The present embodiment is different from the second embodiment in that a return section 70 is provided at a tip end of the distal section 3 and in structure of a frontal section 75 forming the grip section 4. Of course, the present embodiment is same as the second embodiment in the other configuration, material, and hardness. Hereinafter, a description will be given by focusing on such a difference in construction.

The return section 70 orthogonal to the center axis of the dirt remover 1 is provided downwardly of the abutment section 12 of the distal section 3 so as to be opposed to a tip end face of the endoscope. This return section 70 is formed so as to substantially cover the periphery in the downward region of the abutment section 12 positioned at the tip end side of the tube shaped section 11. Further, an upper end of the return section 70 is distant from a lower end of the abutment section 12, and a gap 71 is formed between the return section 70 and the abutment section 12. As shown in FIG. 10B and FIG. 11, an inner face of the return section 70 and a protrusive tip end of the projection section 30 are provided on the substantially same vertical plane. The return section 70 is formed integrally to be in contiguous contact with a tip end lower rim of the tube shaped section 11.

On the other hand, the frontal section 75 forming the grip section 4 has an inner hole 76 through which the endoscope can be inserted. This inner hole 76 consists of: a small diameter portion 76a having a first inner diameter D1 into which the insert section of the endoscope can be inserted; and a large diameter section 76b having an inner diameter D2 through which a thick main body section (frontal grip section 22) of the endoscope can be inserted. The inner diameter of the sheath 2 is equal to the first inner diameter D1, and the inner hole of the sheath 2 and the inner hole 76 of the frontal section 75 coaxially communicate with each other. An engagement section 79 of the frontal section 75 can be engaged with the end of the sheath 2, and the sheath 2 and the frontal section 75 are fixedly bonded with each other at this engagement portion.

A groove shaped fixing stepped section 77 is formed between the small diameter portion 76a and the longer diameter portion 76b of the inner hole 76 of the frontal section 75. An air tightness ring 78 is engaged with this fixing stepped section 77. The inner diameter of the fixing stepped section 77 is greater than any of the first inner diameter D1 of the small diameter portion 76a and the second inner diameter D2 of the large diameter portion 76b. The air tightness ring 78 is formed of an elastic member similar to a material used at the distal section 3, and its central inner diameter is defined to be slightly smaller than D1. Thus, the central inner diameter of the ring 78 is smaller than the outer diameter of the insert section of the endoscope. Further, the outer diameter of the air tightness ring 78 is defined to be equal to the inner diameter of the fixing stepped section 77, and the outer periphery portion of the air tightness ring 78 is fixedly bonded while the ring is engaged in the fixing stepped section 77. This air tightness ring 78 is engaged in a frictional manner in pressure contact with the outer periphery face of the insert section 21 of the endoscope to be inserted into the endoscope dirt remover 1.

A water injection section 81 is provided at the frontal section 75. This water injection section 81 has a water injection path 82 which communicates with the inner hole 76, as shown in FIG. 10C. The water injection path 82 communicates with a region portion of the inner hole 76 positioned at the tip end side rather than the air tightness ring 78, i.e., with the small diameter portion 76a. The water injection section 81 has its shape capable of connecting a syringe (not shown) which is generally used during surgical operation.

An endoscope positioning cutout section 85 which communicates with the large diameter portion 76b is formed at the peripheral wall section of the frontal section 75. A cutout width of this cutout section 85 is set in dimensions in which the light guide post 26 (refer to FIG. 2) of the endoscope 20 can be inserted. Further, the cutout section 85 is closed at the tip end side, and is opened at the proximal end side. The cutout section 85 is provided at the upper portion of the frontal section 75, and extends in a direction orthogonal to the longitudinal direction of the abutment section 12 of the distal section 3. For the length L of the cutout section 85, when the light guide post 26 of the endoscope 20 abuts against an abutment end 88 closed at the tip end depth of the cutout portion 85 (at a dashed position "a" shown in FIG. 12A), the distal section of the endoscope 20 is protruded from the distal section 3, thereby permitting observation using the endoscope 20. In addition, when the light guide post 26 of the endoscope is positioned at an open end 89 of the cutout section 85 (at a dashed position "b" shown in FIG. 12A), as shown in FIG. 11, the objective lens 25 of the endoscope 20 is positioned inwardly of the distal section 3, and the projection section 30 of the distal section 3 is set so as to be adjacently opposed without being in contact with the objective lens 25.

Figure 12B:
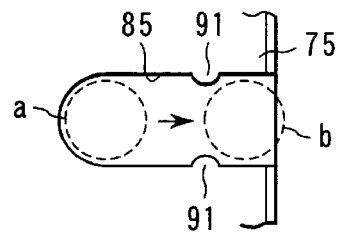
FIG. 12B is a plan section showing essential portions of a grip section according to a modified example of FIG. 12A.

As shown in FIG. 12B, at the open end 89a of the cutout section 85, a projection 91 restricting a position of the light guide post 26 of the endoscope 20 may be provided at the cutout section 85. A projection quantity of this projection 91 into the cutout section 85 is set in quantity such that the projection 91 can come into contact with the light guide post 26, and the light guide post 26 can be inserted into the depth of the cutout section 85 over the projection 91.

Now, a method of removing the dirt on the objective lens 25 of the endoscope 20 by using the endoscope dirt remover 1 according to the present embodiment will be described with reference to FIG. 11 and FIG. 12. The endoscope 20 for use in the present embodiment is obtained as a so-called oblique viewing endoscope in which the objective lens 25 forms a predetermined angle relevant to the center axis of the endoscope 20.

First, prior to surgical operation, the insert portion of the endoscope 20 is inserted to be plugged into the sheath 2 from the large diameter portion 76b of the inner hole 76 provided at the frontal section 75 of the endoscope dirt remover 1. At this time, the endoscope 20 is advanced so that the objective lens 25 of the endoscope 20 does not abut against the abutment section 12 of the distal section 3. That is, the light guide post 26 of the endoscope 20 is aligned with a cutout width of the endoscope positioning cutout section 85, and is positioned at the open end 89 of the cutout section 85 (dashed line position "b" shown in FIG. 12). At this time, the insert section 21 of the endoscope passes through the air tightness ring 78. The center inner diameter of the ring 78 is designed to be smaller than the outer diameter of the insert section 21 of the endoscope. Thus, the insert section is inserted substantially intimately through the inner diameter of the ring.

In carrying out surgical operation, the dirt remover 1 mounted on the endoscope 20 is inserted into the endoscope guide tube that is frequently used in many surgical operation under the endoscope, and is introduced into the cavity. The outer diameter of the insert section of the endoscope dirt remover 1 is defined in its dimensions such that the insert section can be inserted into the endoscope guide tube. In this case, the internal state of the cavity can be observed through a gap between the abutment section 12 and the tube shaped section 11, and the fact that the distal section 3 is reliably introduced into the cavity can be recognized. When the distal section 3 is formed of a transparent elastic member, the inside of the cavity can be better observed.

When it is verified that the distal section 3 has completely jumped from the endoscope guide tube to the inside of the cavity, the frontal section 75 of the endoscope dirt remover 1 is gripped, and only the endoscope 20 is pushed into the tip end side. In this manner, as is the case with the second embodiment, the objective lens 25 of the endoscope 20 abuts against the projection section 30 of the abutment section 12. When the endoscope 20 is further pushed to the tip end side from this state, the objective lens 25 abuts against the return section 70, and then abuts against the projection section 30. The distal section 3 including the abutment section 12 or return section 70 is extended by the characteristics of its elastic element while it is pressed to the surface of the objective lens 25 of the endoscope 20. Thus, the edge portion of the projection section 30 moves along the inclination of the objective lens 25 so as to be intimately abutted against the objective lens 25. Namely, the abutment section 12 and the return section 70 extend while forming a predetermined angle relevant to the center axis of the endoscope dirt remover 1.

When the endoscope 20 is further advanced to the tip end side from this state, the abutment section 12 and the return section 70 increase the resilience force due to the contraction action of an elastic element thereof. As is the case with the second embodiment, the abutment section 12 and the return section 70 are retracted to be moved laterally of the objective lens 25 of the endoscope 20. At this time, as shown in FIG. 12, the light guide post 26 of the endoscope 20 abuts against the abutment end 88 of the positioning cutout section 85 (dashed line position "a" shown in FIG. 12).

During the endoscope 20 is used, although the abutment section 12 and the return section 70 are retracted from the objective lens 25, and are positioned laterally of the endoscope 20, positions thereof are very close to the objective lens 25. Such a position is determined depending on the length L of the positioning cutout section 85, as shown in FIG. 12. According to such position setting, the endoscope 20 can be prevented from being excessively protruded from the distal section 3 and being increased in resistance.

If the dirt is adhered to the objective lens 25 of the endoscope 20 during surgical operation, as described in the second embodiment, the endoscope dirt remover 1 may be advanced/retracted relevant to the endoscope 20. However, when the dirt cannot be removed completely by merely advancing and retracting the endoscope dirt remover 1, it is possible to completely remove the dirt in accordance with the following procedures.

First, the endoscope dirt remover 1 is set (washing position) so that the light guide post 26 of the endoscope 20 is positioned at the dashed line position "b" shown in FIG. 12. At this time, the objective lens face 25 of the endoscope 20 is positioned inside of the distal section 3, as shown in FIG. 11, and is adjacently opposed without being in contact with the projection section 30 of the distal section 3. This position is predetermined depending on the distance L of the cutout section 85, as described above. Thus, the objective lens 25 of the endoscope 20 can be set at its proper position by moving the light guide post 26 at its proper position. Further, as described above, when the projection 91 is provided partially of the positioning cutout section 85, the touch sense is conveyed to the surgeon's hand when the light guide post 26 travels over the projection 91. Thus, even if the position of the frontal light guide post 26 is visually checked, the objective lens 25 can be set at its proper position, and operability is improved more remarkably.

When the endoscope dirt remover 1 is set at its washing position as shown in FIG. 11, physiological saline is injected into the endoscope dirt remover 1 by a syringe (not shown) which is frequently used in surgical operation. Specifically, the syringe is connected to the water injection section 81. The water injection section 81 is formed in the shape in which the syringe can be connected, thus easily making connection between the syringe and the water injection section 81. When the syringe is connected to the water injection section 81, physiological saline is fed from the syringe into the inner hole 76 of the endoscope dirt remover 1 through the water injection section 81. Of course, syringe manipulation is such a water injecting manipulation that is generally made during surgical operation.

The physiological saline injected from the syringe is fed into the small diameter portion 76a of the inner hole 76 of the frontal section 75 through the water injection path 82. At this time, the air tightness ring 78 comes into intimate contact with the side face of the endoscope insert section, thereby preventing liquid leakage. Thus, the physiological saline flows the direction of the distal section 3. The physiological saline oriented in the direction of the distal section 3 reaches the objective lens 25 of the endoscope 20 through a slight gap between the inner hole of the endoscope dirt remover 1 and the insert section of the endoscope 20. At this time, the return section 70 is provided at the distal section 3. Thus, as indicated by the arrow shown in FIG. 11, the physiological saline abuts against the wall face of the distal section 3, a convection current occurs between the distal section 3 and the objective lens 25, and the objective lens 25 is washed. Redundant physiological saline flows from a gap 71, for example, around the abutment section 12 into the cavity together with the adhered dirt.

After the above manipulation has completed, the endoscope dirt remover 1 is moved to the proximal end side, and the objective lens 25 of the endoscope 20 is exposed into the cavity. Of course, when such a manipulation is made, the projection section 30 of the abutment section 12 abuts against the objective lens face 25, and is moved to retract out of the field of view. By this manipulation, however, the physiological saline remaining on the objective lens 25 can be removed readily. Thus, there can be avoided inconvenience that the field of view is interrupted by the physiological saline that remains on the objective lens 25 after washed. The above manipulation is carried out repeatedly until the dirt on the objective lens 25 has been completely removed.

In the present embodiment, washing means by liquid can be used, and thus a washing effect is remarkably improved so that the hard dirt adhered on the objective lens 25 can be easily removed.

FIG. 13 to FIG. 28 each show an eighth embodiment of the present invention. The present embodiment is directed to an embodiment of an endoscope dirt remover compatible with an endoscope guide tube (endoscope guide tube (trocar) with dirt removing function).

Figure 13:
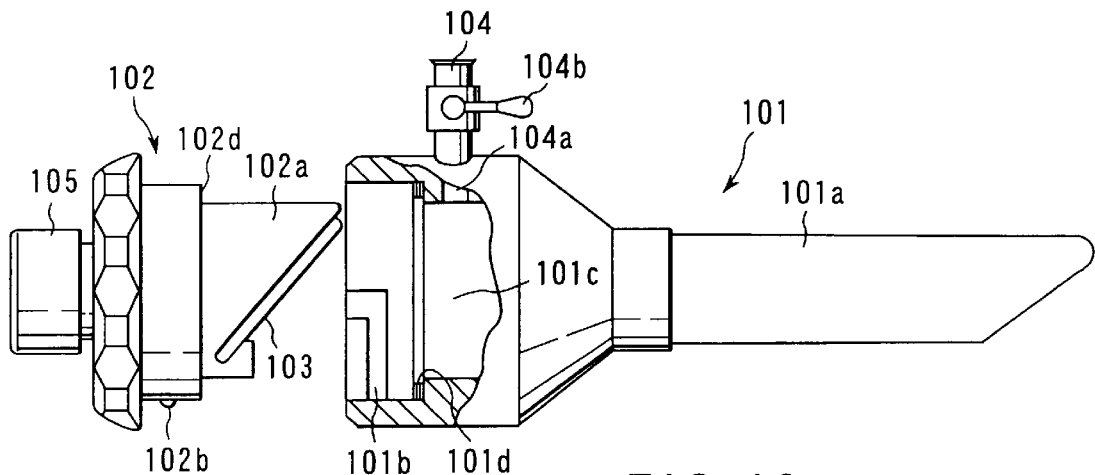
FIG. 13 is a side view having a partial sectional view of an endoscope dirt remover according to an eight embodiment of the present invention.
Figure 15A:
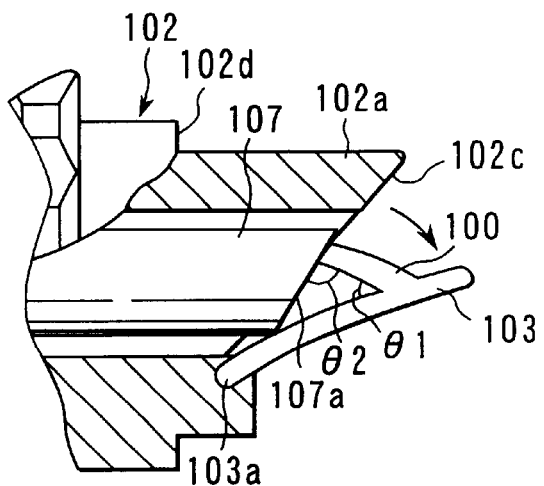
FIG. 15A is a sectional view showing a first actuation state of the endoscope dirt remover shown in FIG. 13.
Figure 15B:
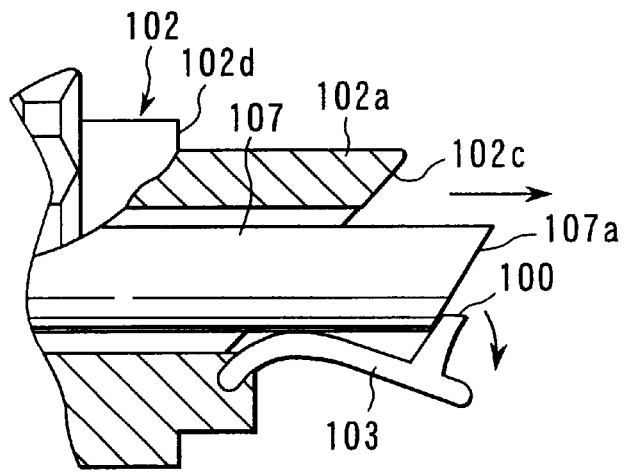
FIG. 15B is a sectional view showing a second actuation state of the endoscope dirt remover shown in FIG. 13.
Figure 22A:
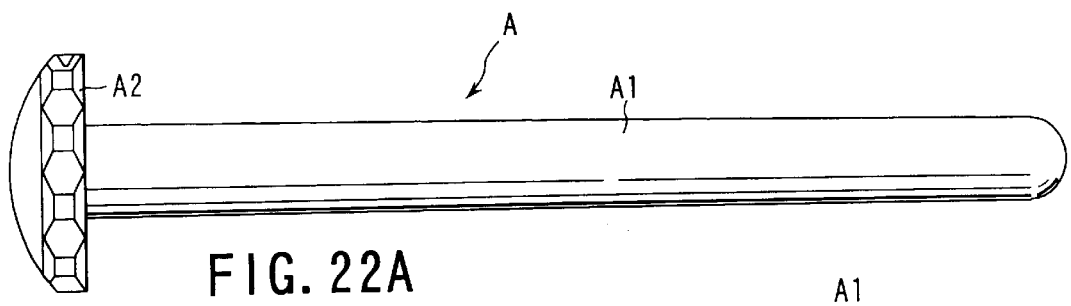
FIG. 22A is a side view of the inner needle.

As shown in FIG. 13, the endoscope dirt embodiment according to the present embodiment is composed of: a tip end insert section 101; a proximal end section 102; and an internal needle A (refer to FIG. 22). As shown in FIG. 22, the internal needle A comprises an insert section A1 and a grip section A2. In this case, a tip end of the insert section A1 may be formed in an obtuse shape as shown in FIG. 22A, and also may be formed in an acute shape as shown in FIG.

22B. The outer diameter of the insert section A1 is defined in its dimensions such that the insert section can be inserted substantially tightly into the tip end insert section 101. In addition, the length of the insert section A1 is sufficiently greater than that obtained by combining the tip end insert section 101 and the proximal section 102.

As shown in FIG. 13, the tip end insert section 101 has: a tube section 101a to be inserted percutaneously into a living body; a junction section 101b; an inner hole 101c through which an endoscope 107 (refer to FIG. 15) can be inserted; an elastic ring 101d arranged at a step at the proximal end side of the inner hole 10c; and a air feed section 104 having formed thereat an air feed tube path 104a which communicates with the inner hole 10c. The air feed section 104 has a lever 104b, and the air feed tube path 104a is shut out or released relevant to the outside by this lever 104b. Also, the elastic is formed of an elastic material such as silicon.

As shown in FIG. 13 and FIG. 14A, the proximal section 102 has: a valve body section 102a having an inner hole through which the endoscope 107 can be inserted; a valve section 103 positioned at a tip end side; a junction projection section 102b; and an insert cap 105. A contact face 102c contacting with the valve section 103 is formed at a tip end of the valve body section 102a. As shown in FIG. 14A in detail, the diameter of the junction projection section 102b is defined in its dimensions such that the projection section 102b can be inserted through the junction section 101b of the tip end insert section 101. Further, the junction projection 102b is arranged at a position at which the elastic ring 101d can be sufficiently pressed into contact with an intimate contact face 102d of the proximal section 102. The outer diameter of the valve body section 102a is smaller than the inner diameter of the elastic ring 101d, and is defined to its dimensions such that the valve body section 102a can be inserted into the inner hole 101c.

The insert cap 105 is formed of an elastic element such as silicon, for example, and is intimately connected to the proximal section 102. Although the insert cap 105 may be fixedly bonded with the proximal section 102, a projection 105a protruded at the insert cap 105 may be configured to be intimately engaged into a recess of the proximal section 102 (FIG. 14A). In this case, the proximal section 102 is provided with a recess corresponding to the projection 105a. A through hole 106 is provided on a face at the proximal end of the insert cap 105. The outer diameter of this hole 106 is smaller than those of the insert section of the endoscope 107 and the insert section A1 of the inner needle A.

The valve section 103 is fixedly bonded with the proximal section 102 at a connection portion 103a which is one end of the valve section. The valve section 103 is formed of an elastic element such as silicon. A wiper projection section 100 is provided at the inner face side (the proximal side) of the valve section 103. The wiper projection section 100 is arranged so as to be positioned in the valve body section 102a while the valve section 103 is closed, i.e., while the valve section 103 abuts against the inclined contact face 102c of the proximal section 102. In addition, an angle formed between the wiper projection section 100 and an inner face of the valve section 103 is set to θ1. Preferably, this angle θ1 is set so that an angle θ2 formed between the wiper projection section 100 and a tip end face (lens face) 107a of the endoscope 107 abutting against the wiper projection section 100 (refer to FIG. 15A) is within the range between 30 to 90 degrees. As shown in FIG. 14C, a width H of the wiper projection section 100 is included in the inner hole of the valve body section 102a, and is set to be greater than a width of the lens face 107a of the endoscope 107.

A modified example of the shape of the wiper projection section is shown in FIG. 14B. A wiper projection section 100A shown in FIG. 14B has a step shaped section 199. The step shaped section 199 comprises a first abutment portion 199a abutting against the lens face 107a of the endoscope 107 and a second abutment portion 199b. A position of the wiper projection section 100A on the valve section 103 is set in the same manner as described above.

Although the wiper projection sections 100 and 100A are molded integrally with the valve section 103, as shown in FIG. 14D, a wiper projection section 100B is formed independently of the valve section 103 so that the wiper projection section 100B may be fixedly bonded with the valve section 103 by a fastener 103.

Figure 16:
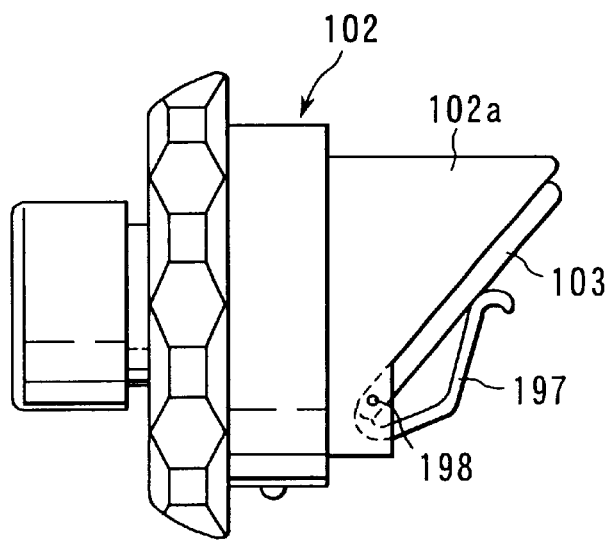
FIG. 16 is a side view showing a third modified example of the valve configuration shown in FIG. 14A.

FIG. 16 shows a modified example of the valve section 103. This valve section 103 is formed of a hard resin so as to be turned around a fulcrum 198 provided at the valve main body 102a. Further, the valve section 103 is always biased in a direction such that the valve section 103 is closed by a plate spring 197 mounted on the valve body section 102a at one end of the valve section.

Figure 22B:
FIG. 22B is a side view showing a tip end of the inner needle according to a modified example of the inner needle shown in FIG. 22A.
Figure 23:
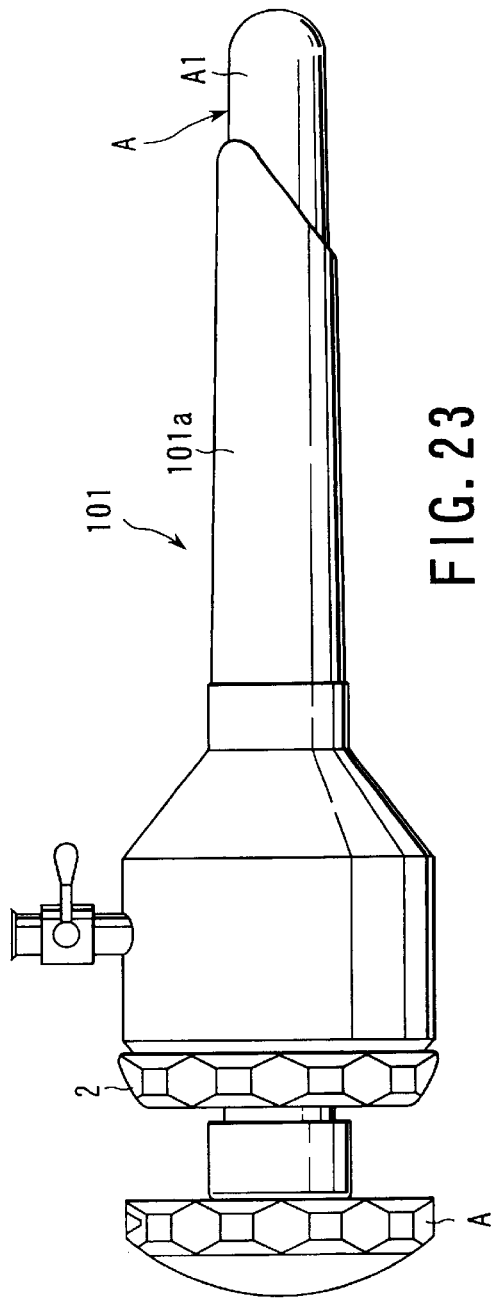
FIG. 23 is a side vie showing a state when the inner needle shown in FIG. 22A is inserted into the endoscope dirt remover shown in FIG. 13.
Figure 24C:
FIG. 24C is a sectional view showing a protection cap according to a modified example of the protection cap shown in FIG. 24B.
Figure 24B:
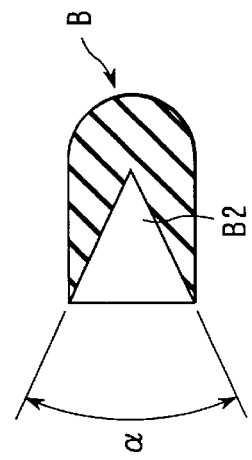
FIG. 24B is a sectional view of the protection cap shown in FIG. 24.
Figure 24A:
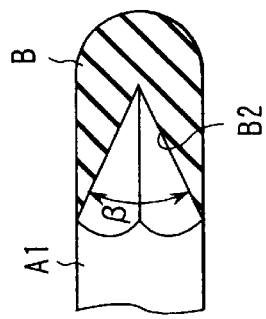
FIG. 24A is a sectional view showing a state when a protection cap is attached to the distal section of the inner needle shown in FIG. 22B.

FIG. 24 shows a protection cap B removably mounted at a sharp distal section of the insert section A1 of the inner needle A shown in FIG. 22B. The protection cap B is formed in an obtuse angle at its tip end, and has a tapered inner hole B2 forming the shape analogous to the tip end shape of the inner needle A at its proximal end. The outer diameter of the protection cap B is slightly smaller than that of the inner needle A. It is preferable that the surface properties of the protection cap B is like a pair surface. A tapered angle α of the tapered shape of the inner hole B2 (refer to FIG. 24B) is smaller than a tapered angle β (refer to FIG. 24A) of the tapered shape at the sharp tip end of the inner needle A (α>β). The protection cap B is formed of an elastic, flexible material, and it is preferable that the shear strength is high. The tip end side of the protection cap B may be a tapered obtuse shape, as shown in FIG. 24C.

Figure 25:
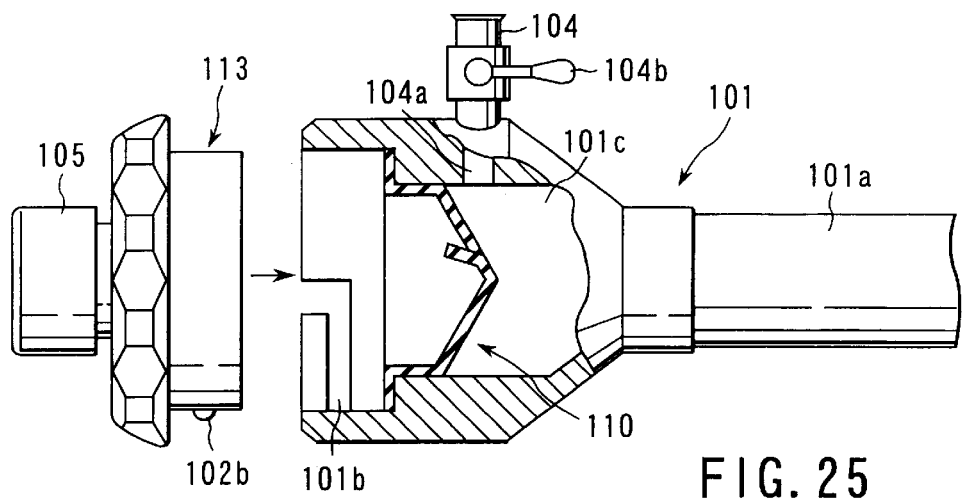
FIG. 25 is a side view having a partial sectional view of an endoscope dirt remover having a duckbill valve.
Figure 26A:
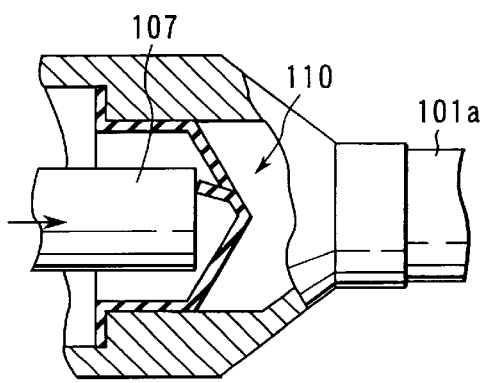
FIG. 26A is a sectional view showing a first actuation state of the duckbill valve shown in FIG. 25.
Figure 26B:
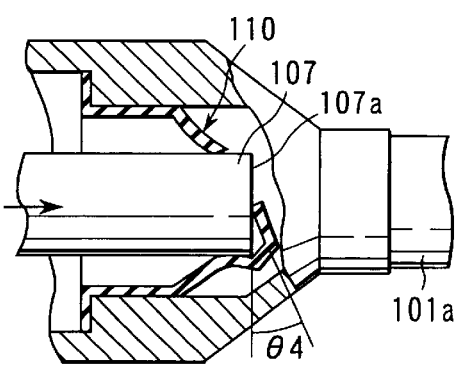
FIG. 26B is a sectional view showing a second actuation state of the duckbill valve shown in FIG. 25.

In general, the valve constitution of an endoscope guide tube includes a structure in which one end of the valve is fixed, and is opened/closed by an elastic force of the valve itself and a structure in which a hard valve is opened/closed by a spring. On the other hand, as in a duck bill valve 119 shown in FIG. 28, there is provided a valve constitution in which only parts having a cutout 119a provided at a part of the elastic member are used. An endoscope dirt remover compatible with an endoscope guide tube of this valve constitution (endoscope guide tube with dirt removing function) is shown in FIG. 25.

This endoscope dirt remover forms a configuration in which the ring 101d of the endoscope dirt remover shown in FIG. 13 is replaced with a duck bill valve 110. In addition, a proximal section 113 of this endoscope dirt remover forms a structure the valve section 103 and the valve body section 102a are removed from the proximal section 102 shown in FIG. 13. Another configuration of the proximal section 113 is similar to the proximal section 102.

Figure 27A:
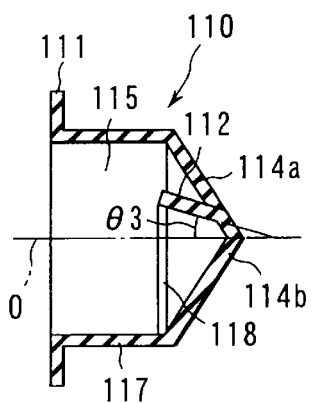
FIG. 27A is a sectional view showing the duckbill valve shown in FIG. 25.
Figure 27B:
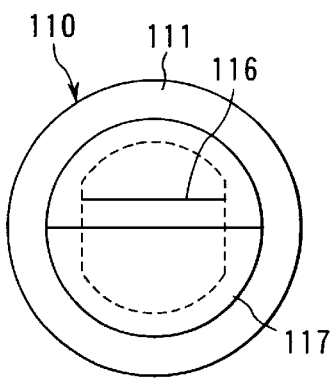
FIG. 27B is a front view of the duckbill valve shown in FIG. 27A.
Figure 28:
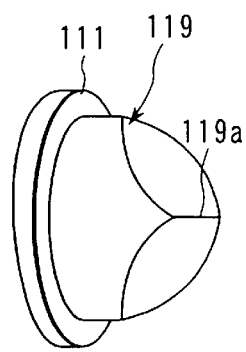
FIG. 28 is a perspective view showing another duckbill valve.

As shown in FIG. 27A, the duck bill valve 110 is composed of: a rib section 111 at its proximal end side; inclined sections 114a and 114b at its tip end side; a wiper projection section 112; an inner hole 115 through which the endoscope 107 can be inserted; a slit 116 (refer to FIG. 27B); and a main body section 117. The outer diameter of the rib section 111 is defined in dimensions such that the rib section 111 hooks on a step at the proximal end side of the inner hole 101c of the tip end insert section 101. In addition, the main body section 117 has an external shape such that the main body 117 section is housed in the inner hole 101c of the tip end insert section 101. The proximal side portion of the wiper projection section 112 communicates with the inclined section 114b. Further, the tip end side of the inclined section 114a comes into intimate contact with the proximal side portion of the wiper projection section 112, and the slit 116 is formed. It is preferable that the wiper projection section 112 be positioned at, and extend to a proximal end side more than a transition line 118 transiting from the main body section 117 to the inclined sections 114a and 114b. In addition, the wiper projection section 112 extends to the inclined section 114a relevant to a center line O of the duck bill valve 110, and forms a predetermined angle θ3 with the center line O. This angle θ3 is defied so that an angle θ4 (refer to FIG. 26B) formed by the wiper projection section 112 and the tip end face (lens face) 107a of the endoscope 107 abutting against the wiper projection section 112 is within the range of 30 to 90 degrees.

Now, a description will be described with respect to a method for removing the dirt on the lens face of the endoscope 107 during surgical operation under the endoscope by using the endoscope dirt remover shown in FIG. 13.

First, the proximal section 102 is mounted on the insert distal section 101. Connection between the insert distal section 101 and the proximal section 102 is made by engaging the joint projection section 102b with the joint section 101b of the tip end insert section 101. The joint projection section 102b is aligned with a cutout of the joint section 101b, and the proximal section 102 is pushed in the tip end direction. After that, when the proximal section 102 is rotated along the shape of the joint section 101b, the joint projection section 102b moves along the joint section 101b, the elastic ring 101d is compressed on the intimate contact face 102d of the proximal section 102, and the internal air tightness of the inner hole 101c is maintained.

Next, the inner needle A is inserted into the hole 106 of the proximal section 102. At this time, when the tip end of the insert section A1 of the inner needle A is formed in an obtuse shape, the inner needle A is inserted into the tip end insert section 101 until the grip section A2 and the insert cap 105 has abutted against each other. However, when he tip end of the insert section A1 of the inner needle A is formed in a sharp shape, the inner needle A is inserted in accordance with the following procedure.

First, before inserting the inner needle A, the protection cap B is mounted at the tip end of the inner needle A. At this time, the protection cap B is flexible, and the tapered angle α of the inner hole B2 is smaller than the tapered angle β at the tip end of the inner needle A. Thus, the protection cap B is deformed in accordance with the tip end shape of the inner needle A. Therefore, the protection cap B is mounted substantially intimately relevant to the inner needle A by its elastic resilience force of which the cap is restored in its original shape. In addition, the protection cap B is high in shear strength, and is not cut off at a sharp portion of the inner needle A. The protection cap B is arranged so as not to be greater than the outer diameter of the inner needle A at its outer diameter when it is mounted at the tip end of the inner needle A.

In the above state, the inner needle A with the protection cap is inserted into the hole 106 of the insert cap 105. At this time, the insert cap 105 is made of an elastic element, and the diameter of the hole 106 is deformed according to insertion of the inner needle A. At this time, since the outer surface of the protection cap B is like a pair surface, the surface resistance between the insert cap and the protection cap can be reduced. Therefore, the resistance when the inner needle A passes through the hole 106 can be very small (it is should be noted that if the tip end shape of the protection cap B is formed in a tapered obtuse shape (refer to FIG. 24C), the resistance when the inner needle A passes through the hole 106 is further small, and the insert properties is improved more remarkably). When the protection cap B is attached to the inner needle A, the outer diameter of the protection cap B isn't larger than that of the inner needle A so that the insert section of the inner needle can be inserted into the tube section (valve body section) 102a of the proximal section 102 smoothly.

When the inner needle A passes through the inner hole of the proximal section 102, first, the needle A abuts against the wiper projection section 100 of the valve section 103. Then, the wiper projection section 100 is deformed, and the valve section 103 is deformed at the tip end side around the connection portion 103a. As a result, the valve section 103 is released from the contact face 102c with the valve body section 102, and the valve 103 is released. Then, the inner needle A passes from a gap of the opened valve to the tip end direction, and is exposed to the outside from a tip end of the tube section 101a. When the protection cap B is mounted at the sharp distal section of the inner needle A, the wiper projection section 100 is not scratched or damaged at the sharp section when the inner needle A is inserted.

A length of the insert section A1 of the inner needle A is sufficiently greater than that when the tip end insert section 101 and the proximal section 102 are combined with each other. Thus, when the grip section A2 abuts against the insert cap 105, the sharp tip end of the inner needle A is reliably exposed to the outside from the tip end of the tip end insert section 101. When a tip end of the inner needle A is exposed to the outside from the tip end of the tip end insert section 101, the protection cap B is removed from the sharp tip end section of the inner needle A. While the tip end insert section 101, the proximal section 102, and the inner needle A are combined with each other, these are punctured from a patient's body surface to an internal part of a living body, and then, the inner needle A is pulled out from the tip end insert section 101 and the proximal section 102. At this time, the valve section 103 is restored in its original state from the deformed state by its elastic force, and comes into intimate contact with the contact face 102c of the valve body section 102a. In this manner, the inner hole of the tip end insert section 101 is maintained by the valve section 103 with air tightness, and the pressure gas fed to the inner cavity of the living body does not leak to the outside. Of course, after the inner hole of the tip end insert section 101 is maintained by the valve section 103 with air tightness, the gas feed tube path may be connected to the air feed section 104 so as to feed air to the inner cavity of the living body.

Next, in order to observe the inside of the living body, the endoscope 107 is inserted into the tip end insert section 101 from the insert cap 105. The endoscope 107 is introduced into the living body from the tip end of the tip end insert section 101 through the valve section 103. Since the inner diameter of the hole 106 of the insert cap 105 is smaller than the outer diameter of the insert section of the endoscope, the hole 106 is expanded to be pushed by the insert section of the endoscope 107, and comes into intimate contact with the outer periphery of the insert section of the endoscope 107. Therefore, when the endoscope 107 is passed through the valve section 103, the gas fed into the living body is prevented from being discharged to the outside of the body.

When the inside of the living body can be observed by the endoscope, the subsequent work is carried out in accordance with general procedures for surgical operation under the endoscope.

Now, a description will be given with respect to a method for restoring the field of view when the lens face 107a of the endoscope 107 is cloudy or is contaminated as the first embodiment, during surgical operation.

When an attempt is made to restore the field of view, the endoscope 107 is slid toward the proximal section 102 until the valve section 103 has been closed. Then, the endoscope 107 is slid again in its tip end direction. At this time, the wiper projection section 100 abuts against the endoscope 107. The abutment position is more proximal than the position of the connection portion 103a. Thus, at first, the wiper projection section 100 is pushed to the tip end surface of the endoscope 107, whereby the valve section 103 is deformed. Namely, the wiper projection section 100 always abuts against the endoscope 107 upwardly of the lens face 107a, and the projection section 100 can reliably abut against the tip end face of the endoscope. Thus, non-uniform wiping can be reduced (refer to FIG. 15A). When the endoscope 107 is further advanced to the tip end side, the wiper projection section 100 is deformed, and the valve section 103 is deformed at the tip end side around the connection portion 103a (the valve section 103 is released from the contact face 102c). At this time, the wiper projection section 100 abuts against the valve section 103 at the angle of θ1, the wiper projection section 100 abuts against the lens face 107a at the angle of θ2 (30 to 90 degrees). A supplemental description of the angle θ2 will be given here. When the wiper projection section and the lens face abut against each other in the range of the angle θ2, it is found that the dirt can be easily removed from experience. When the endoscope 107 is further advanced, the wiper projection section 100 moves on the lens face 107a, and enters the state shown in FIG. 15B. Finally, the endoscope 107 is inserted into the tip end insert section 101 over the wiper projection section 100, and is introduced into the living body. Since the wiper projection section abuts against the lens face 107a at the angle of θ2, the dirt on the lens can be better removed, the oil film can be uniformed, and the field of view can be restored. Where the degree of restoring the field of view is low after a series of dirt removing operations described above is made once, the operation is carried out repeatedly. As shown in FIG. 16, in a structure in which the valve section 103 is opened/closed by the plate spring 197 as well, the dirt can be removed by the similar operating method.

A dirt removing operation when the valve section 103 forms a configuration shown in FIG. 25 will be described below.

First, if the lens face 107a of the endoscope 107 is contaminated, the endoscope 107 is slid toward the proximal section 102 until the valve section 103 has been closed in the same manner as described above. Then, the endoscope 107 is again slid in its tip end direction. At this time, since the wiper projection section 112 on the duck bill valve 100 is positioned at the proximal end side more than the transition line 118, the wiper projection section 112 first abuts against the lens face 107a of the endoscope 107 (refer to FIG. 26A). Then, if the endoscope 107 is advanced, the inclined sections 114a and 114b are deformed. As a result, a slit formed by end portions of the inclined sections 114a and 114b come into intimate abutment against each other as well is deformed and opened. The endoscope 107 is inserted into the tip end insert section 101 through this opening. Of course, the angle θ4 at which the wiper projection section 112 abuts against the lens face 107a is in the range of angle similar to θ2 described previously. Namely, the angle θ3 is designed to be θ4 that is an optimal abutment angle (θ2 described previously).

An angle $θ_4$ when the wiper projection section 112 abuts against the lens face 107a and the fact that the wiper projection section 112 firstly abuts against the endoscope 107 upwardly of the lens face 107a are as described above. Therefore, as the endoscope 107 is advanced, the wiper abutment section 112 moves on the lens face 107a. Finally, the endoscope 107 moves to the tip end side (the side surface of the insert section of the endoscope) over the wiper abutment section 112, and the field of view is restored. When an operation of the valves of two types described previously is described, the forward-oblique viewing endscope and forward (direct)-viewing endoscope type endoscopes are shown on the drawings, respectively. The forward-oblique viewing endscope and forward (direct)-viewing endoscope can be used in both of the valve structures, and the wiper projection section (100 or 112) functions without any problem. A case in which a dirt removing function (wiper projection section) is provided at the valve section 103 has been described above. Hereinafter, a case in which a dirt removing function is provided at the tip end of the tube section 101a of the tip end insert section 101 will be described.

FIG. 17 to FIG. 20 each show such endoscope dirt remover 150. As shown in FIG. 17, the endoscope dirt remover 150 is composed of: a proximal section 151; a tip end insert section 166; and an inner needle 159 (refer to FIG. 18). A configuration of a valve section 165 of the proximal section 151 is different from that of the valve section 103 of the proximal section 102 described above. That is, no wiper projection section is provided at the valve section 165. The other configuration of the proximal section 151 is similar to that of the proximal section 102 described above.

Differences between the tip end insert section 101 described above and the tip end insert section 166 lie in a configuration of a tube section 152 to be inserted into the body and an indicator (marking) 170 provided on a body section 171 of the tip end insert section 166. The other configuration is similar to the tip end insert section 1 described above. A distal section 153 having a wiper projection section 158 is provided at the tip end side of the tube section 152. The detail at the tip end side of the tube section 152 is shown in a sectional view of FIG. 17B. As shown in FIG. 17B, relief sections 154 are provided at both sides at the tip end of the tube section 152. As shown in FIG. 17B, these relief sections 154 are positioned at one side (upper side shown in FIG. 17B) relevant to the center axis O, and opposed to each other (one of these relief section 154 isn't shown in FIG. 17B). In addition, steps 155 are formed, respectively, on the internal and external faces of the distal section of the tube section 152. That is, thickness t1 of the distal section of the tube section 152 is smaller than thickness "t" of other sites of the tube section 152.

FIG. 17C shows a state in which the distal section 153 is provided at the tip end side of the tube section 152. The distal section 153 is formed of a silicon or polyurethane based elastic element, for example. In addition, the distal section 153 is insert molded (integrally molded) at a portion at which the step 155 of the tube section 152 is provided. A rise section 157 and the wiper projection section 158 are provided at the distal section 153. As shown in FIG. 17D which is a top view of the tip end section 153, the wiper projection section 158 is formed in a band shape (strip shape) having a predetermined width, and extends so as to cross the distal section 153 vertically to its axial direction. Further, the rise sections 157 are formed at both sides of the wiper projection section 158. In addition, as shown in FIG. 17C, the rise section 157 is disposed in each relief section 154 of the tube section 152. An inward site of the wiper projection section 158 (a site to be opposed to the inner hole of the tube section 152) is formed in a protrusive shape, and an edge 167 is formed. The indicator 170 provided on the body section 171 of the tip end insert section 166 is provided in a direction in which the wiper projection section 158 of the distal section 153 is arranged. L shown in FIG. 17A and FIG. 17D indicates a distance between the distal face of the proximal section 151 when the proximal section 151 and tip end insert section 166 are combined with each other and the edge section 167 of the wiper projection section 158.

Figure 18:
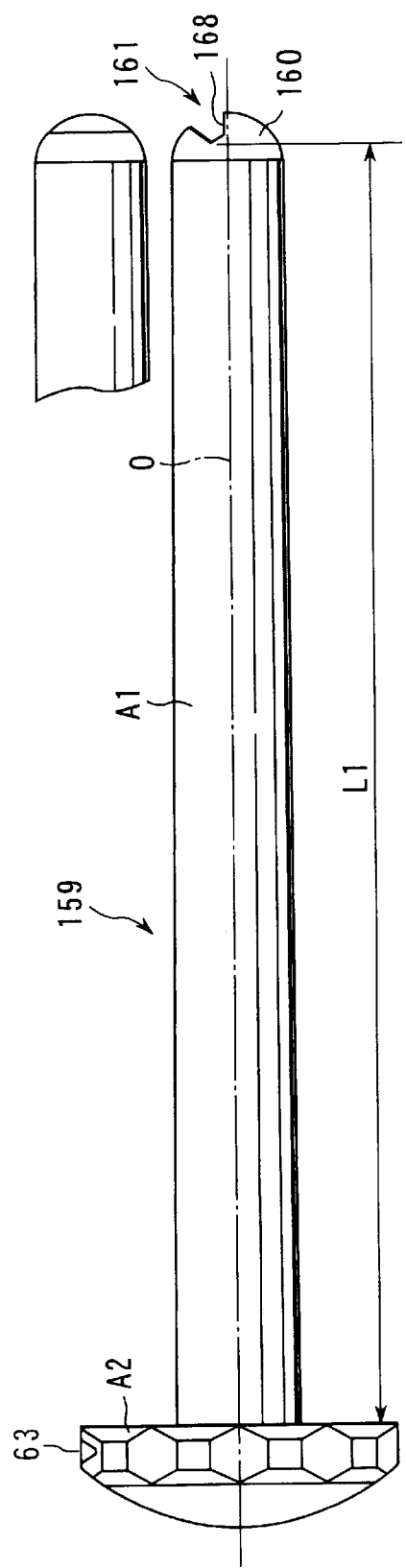
FIG. 18 is a side view of an inner needle.

FIG. 18 shows the entirety of the inner needle 159. Differences between the inner needle 159 and the inner needle A described above lie in only a configuration of a tip end and an indicator 163 provided on the grip section A2 (the other constituent elements are similar to those of the internal needle A described above). A distal section 160 of the inner needle 159 is formed in a hemispherical shape, and communicate with the insert section A1. A retracting section 161 is provided at a part of this hemispherical shape. The retracting section 161 is formed of a cutout provided vertical to an axial direction of the inner needle 159. This cutout shape substantially coincides with the shape of the wiper projection section 158, and has a slide face 168 on which the wiper projection section 158 moves. The slide face 168 is substantially parallel to the center axis O. The retracting section 161 is designed so that the wiper projection section 158 is housed in the retracting section 161 when the inner needle 159 is combined with a part assembly between the proximal section 151 and the tip end insert section 166. It is preferable that a rise line section adjacent to the retracting section 161 is slightly formed in an R shape. In addition, the indicator 163 provided on the grip section A2 is provided in a direction in which the retracting section 161 provided at the distal section of the inner needle 159 is arranged.

On the other hand, a modified example in which the tip end of the inner needle 159 is formed of a conical shape is shown in FIG. 20. This cone forming the distal section 160 of the inner needle 159 is composed of three faces 156 on which an apex 169 is defined as the most tip end. A rise line 164 of the mutually adjacent faces 156 forms a blade shape cooperatively. In addition a rise line between the face 156 and the insert section A1 is not formed in a blade shape each other.

In this example, although a retracting section 162 is provided on the face 156, the retracting section 162 is reached to a rise section 172 formed by the face 156 and the insert section A1. The retracting section 162 is structured to be cutout, and substantially coincides with the shape of the wiper projection section 158. In addition, a slide face 168' formed in the retracting section 162 slightly forms an angle relevant to the center axis O. Of course, the slide face 168' may be parallel to the center axis O. In addition, the retracting section 162 has a face 162a extending in a direction substantially vertical to the center axis O and parallel to the face 156. It is preferable that a rise line section adjacent to the retracting section 162 be slightly formed in an R shape. In the inner needle 159, a distance L1 between a face of the grip section A2 abutting against the proximal section 151 and a site of the retracting section 162 abutting against the edge 167 of the wiper projection section 158 (refer to FIG. 20A) is slightly greater than the distance L.

Now, a description will be given with respect to surgical operation under the endoscope using the above constructed endoscope dirt remover 150.

First, the proximal section 151 is assembled with the tip end insert portion 166. This assembling is carried out in the same manner as that in the endoscope dirt remover shown in FIG. 13. Next, the inner needle 159 is assembled with this part assembly (assembler between the proximal section 151 and the tip end insert section 166). Hereinafter, a case in which the inner needle whose tip end is formed in a hemispheric shape (obtuse shape) is assembled, will be described.

The inner needle 159 is inserted into the proximal section 151. The inner needle 159 opens the valve section 165 in the proximal section 151 by its tip end, and is inserted into the tip end insert section 166. Then, as shown in FIG. 19, the tip end of the inner needle 159 is exposed to the outside via the inside of the distal section 153 of the tube section 152. Specifically, as shown in FIG. 19A, the distal section 160 of the inner needle 159 is positioned in the vicinity of the wiper projection section 158. At this time, the center of the inner needle 159 substantially coincides with that of the tube section 152. In addition, the wiper projection section 158 is arranged at a position to be shifted more one-sidedly than the center axis O. When the inner needle 159 is advanced to the tip end side, if the orientation of the indicator 163 provided on the grip section A2 is aligned with that of the indicator 170 provided on the body section 171 of the tip end insert section 166, the retracting section 161 at the tip end of the inner needle 159 and the wire projection section 158 are positioned in the substantially same direction so that the wiper projection section 158 can be reliably introduced into the retracting section 161.

When the inner needle 159 is further advanced from the state shown in FIG. 19A, the wiper projection section 158 is positioned in the retracting section 161, as described above (refer to FIG. 19B). At this time, since the slide face 168 in the retracting section 161 is parallel to the center axis O, there is almost no resistance when the wiper projection section 158 is introduced into the retracting section 161. In order to reduce a degree of a gap 173 generated when the wiper projection section 158 is assembled with the retracting section 161, the slide face 168' which is slightly inclined relevant to the center axis O may be employed as described above (refer to FIG. 19E). A gap 173' generated by the slide face 168' is smaller than the above gap 173. In this case, the wiper projection section 158 (and the rise section 157) is made of an elastic element, and thus, is elastically deformed itself. Then, this section 158 can invade the retracting section 161 over the slide face 168'.

FIG. 19D is a top plan view showing a state in which the wiper projection section 158 and the retracting section 161 are assembled with each other. In this state, a gap is generated between the rise section 157 and the distal section 160. From this state, when the inner needle 159 is advanced until the grip section A2 of the inner needle 159 has abutted against the proximal end section 151, the wiper projection section 158 is slightly advanced in its tip end direction (a tension is applied to the projection section 158) (refer to FIG. 19C and FIG. 19F). This is because that the distance L1 of the inner needle 159 is slightly greater than the distance L between the proximal section 151 and the edge 167 of the wiper projection section 158.

In the state shown in FIG. 19C and FIG. 19F, the rise section 157 abuts against the distal section 160 in its elongated and deformed state (refer to FIG. 19F). Namely, the gap generated between the rise section 157 and the distal section 160 is eliminated so that the resistance when inner needle 159 and the tube section 152 are inserted into the body can be reduced. If the rise line section adjacent to the retracting section 161 is formed in an R shape, the wiper projection section 158 and the rise section 157 are not scratched or not destroyed even when the tension is applied. Here, the distal section 153 according to the present embodiment may be configured at the distal section 3 of the second embodiment (namely, the relief section may be not present the sheath 2 as shown in FIG. 3A). Operation and advantageous effect caused by the relief section will be described below.

The distal section 153 is percutaneously introduced into a body cavity, but is strongly compressed against a body tissue. The relief section 154 is provided at the distal section 153, and a rise section is disposed therein. This makes it possible to reduce a length of the rise section required for the wiper projection section to remove the dirt and a portion of only an elastic element at the tip end side. Therefore, when the distal section is strongly compressed against the body tissues, a portion of the elastic element only does not move. Hence, the adhesive release of the distal section 153 and the tube section 152 can be prevented more significantly.

When the state shown in FIG. 19C is obtained, the endoscope dirt remover is inserted into a living body. During this insertion as well, a force is applied to the periphery of the wiper projection section 158 and the retracting section 161. However, the rise line section adjacent to the retracting section 161 is formed in the R shape. Thus, the wiper projection section 158 is not destroyed. After the tube section 152 of the tip end insert section 166 has been successfully inserted into the living body, the inner needle 159 is pulled out from the tip end insert section 166, and a part assembly of the tip end insert section 166 and the proximal section 151 is left.

The resistance when only the inner needle 159 is pulled out is very small at the retracting section 161 having the slide face 168 parallel to the center axis O. Even in the slide face 168' having a slight angle relevant to the center axis O, the wiper projection section 158 (and the rise section 157) is elastically deformed and can be released from the retracting section 162. Thus, the inner needle 159 can be easily pulled out.

Now, a case in which the inner needle 159 (refer to FIG. 20A) whose tip end forms a conical shape will be described here. The inner needle 159 is assembled with the proximal end 151 and tip end insert section 166 in the same manner as described above.

FIG. 20B shows a state in which the distal section 60 of the inner needle 159 shown in FIG. 20A is positioned in the vicinity of the wiper projection section 158. The center of the inner needle 159 substantially coincides with that of the tube section 152. In addition, the wiper projection section 158 is arranged at a position shifted more one-sidedly than the center axis O. When the inner needle 159 is advanced from this state, the orientation of the indicator 163 provided on the grip section A2 is aligned with that of the indicator 170 provided on the body section 171 of the tip end insert section 166. In this manner, the retracting section 162 at the tip end of the inner needle 159 and the wiper projection section 158 are positioned in the substantially same direction so that the wiper projection section 158 can be reliably introduced into the retracting section 162.

The most tip end 69 of the inner needle is positioned on the center axis of the tube section 152, and the wiper projection section 158 is arranged to be shifted one-sidedly from the center axis of the tube section 152. Thus, even if the inner needle 159 is advanced, the wiper projection section 158 is not destroyed at the most tip end 169. In addition, the inner needle 159 is inserted while the indicators 163 and 170 are aligned with each other, the wiper projection section 158 moves on the face 156 of the distal section (this section does not move on the blade section). That is, the wiper projection section 158 (and the rise section 157) does not abut against the blade section formed by the rise line 164 of the face 156. Therefore, the wiper projection section 158 is not destroyed by the blade section. At a site on the face 156 which the wiper abutment section 158 abuts against and moves to, a majority of the site is a blade free rise line 172. Thus, the wiper abutment section 158 is not scratched or damaged.

When the inner needle 159 is further advanced from the state shown in FIG. 20B, the wiper projection section 158 is arranged in the retracting section 162 (refer to FIG. 20C). At this time, the slide face 168' in the retracting section 162 is slightly inclined relevant to the center axis O. Thus, the degree of the gap 173' generated when the wiper projection section 158 is combined with the retracting section 162 is small, and an insert resistance can be reduced. In the state shown in FIG. 20C as well, a gap between the rise section 157 and the tip end section 160 is generated in the same manner as described above (refer to FIG. 19D).

When the inner needle 159 is further advanced toward the tip end side until the grip section A2 of the rise section 159 has abutted against the proximal section 151, the wiper projection section 158 is slightly advanced in the tip end direction (a tension is applied to the projection section 158) (refer to FIG. 20D). This is because the distance L1 of the inner needle 159 is slightly greater than the distance L between the proximal section 151 and the edge 167 of the wiper projection section 158.

In the state shown in FIG. 20D, the rise section 157 abuts against the distal section 160 in an elongated and deformed state. Namely, the gap generated between the rise section 157 and the distal section 160 is eliminated so that the resistance when the inner needle 159 and the tube section 152 are inserted into the body can be reduced. As long as the rise section adjacent to the retracting section 161 has an R shape, even if the tension is applied, the wiper projection section 158 and the rise section 157 are not scratched or destroyed.

When the state shown in FIG. 20D is obtained, the endoscope dirt remover is inserted into the living body. During this insertion as well, the force is applied around the wiper projection section 158 and the retracting section 162. However, since the rise line section adjacent to the retracting section 162 is formed in an R shape, the wiper projection section 158 is not destroyed. When the tube section 152 of the tip end insert section 166 has been successfully inserted into the living body, the inner needle 159 is pulled out from the tip end insert section 166, and the part assembly of the tip end insert section 166 and the proximal section 151 is left.

The resistance when only the inner needle 159 is pulled out is smaller in a case of the retracting section 161 having the slide face 168 parallel to the center axis O. However, even in the case of the slide 168' having a slight angle relevant to the center axis O, the wiper projection section 158 (and the rise section 157) is elastically deformed, and can be released from the retracting section 162. Thus, the inner needle 169 can be easily pulled out.

Figure 21A:
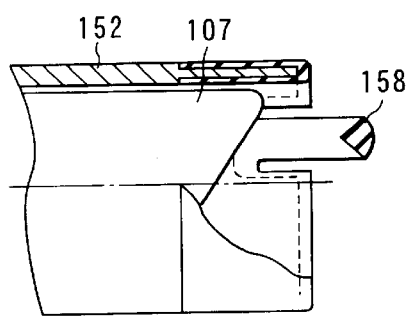
FIG. 21A is a sectional view showing a first actuation state when the endoscope is inserted into the endoscope dirt remover shown in FIG. 17A.
Figure 21B:
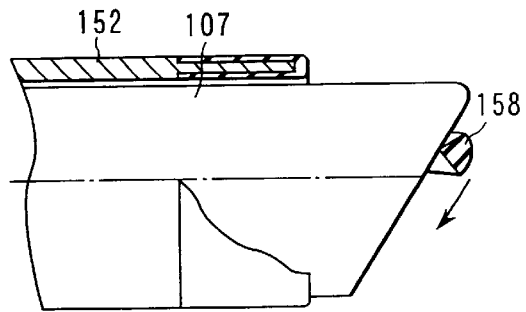
FIG. 21B is a sectional view showing a second actuation state when the endoscope is inserted into the endoscope dirt remover shown in FIG. 17A.
Figure 21C:
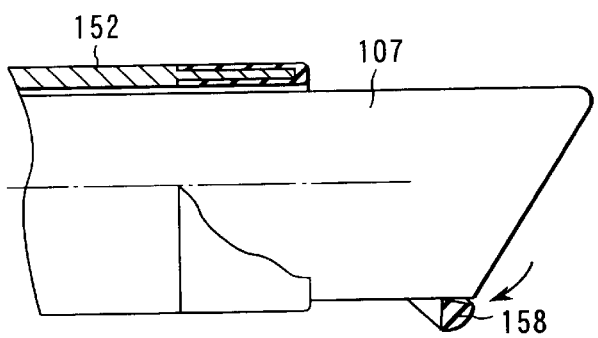
FIG. 21C is a sectional view showing a third actuation state when the endoscope is inserted into the endoscope dirt remover shown in FIG. 17A.
Figure 21D:
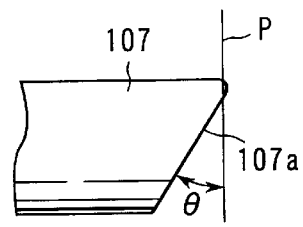
FIG. 21D is a side view showing a tip end of the endoscope.

After the inner needle 159 has been pulled out as described above, the endoscope 107 is inserted into the tip end insert section 166, and the inside of the body is observed. As shown in FIG. 21D, the endoscope 107 is an oblique viewing endoscope in which the lens face 107a at its tip end forms a predetermined angle θ relevant to a vertical face P. An operation after introducing the endoscope 107 into the body conform to general surgical operation under the general endoscope.

The indicator 170 for indicating a position of the wiper projection section 158 is provided at the body section 171 of the tip end insert section 166. Thus, if the endoscope 107 is inserted into the tip end insert section 166 while an upper rim section of the lens face 107a of the endoscope 107 is oriented toward this indicator 170, the wiper projection section 158 is arranged at the upper rim section of the lens face 107a of the endoscope 107 when the endoscope 107 introduced into the tube section 152 passes through the inside of the distal section 153. When the endoscope 107 is further advanced from this state, the edge 167 of the wiper projection section 158 abuts against the top face of the lens face 107a of the endoscope 107. The wiper projection section 158 (and the rise section 157) is made of an elastic member, and thus, extends in its tip end direction as the endoscope 107 is advanced (refer to FIG. 21B). When the endoscope 107 is further advanced from this state, the wiper projection section 158 moves downwardly of the lens face 107a due to an elastic resilience force (restoration force) of the wiper projection section 158 and inclination of the lens face 107a. Finally, the wiper projection section 158 is arranged on a side face of the endoscope 107, and is retracted to the outside of the field of view in the endoscope 107. In this manner, the inside of the body can be observed by the endoscope 107. The subsequent procedure is carried out in accordance with procedures for surgical operation under the endoscope that is generally carried out.

When surgical operation is advanced, a variety of dirt objects such as condensation, cloud of electrical knives, blood or fluid adheres to the lens face 107a of the endoscope 107. If such a dirt is adhered to the tip end of the endoscope 107, the endoscope 107 is slid in its proximal end side direction, and the tip end lens face 107a of the endoscope 107 is moved to the inside of the distal section 153. When the tip end lens face 107a of the endoscope 107 is positioned inside of the distal section 153, the wiper projection section 158 moves from the side face to the front face of the endoscope 107 due to its elastic resilience force (restoration force) (the wiper projection section 158 enters the inside of the field of view in the endoscope 107). Therefore, when the endoscope 107 is slid in its tip end direction again in this state, the edge 167 of the wiper projection portion 158 moves while abutting against the contaminated lens face 107a of the endoscope 107, and the dirt is wiped. The edge 167 is moved while wiping the dirt on the lens face 107a downwardly, and thus, the field of view after wiped is cleared. The wiper projection section 158 is finally retracted to the outside of the field of view (side face of the endoscope), thus enabling subsequent endoscope observation.

When the edge 167 moves from the lens face 107a to the side face of the endoscope 107, the dirt on the lens face 107a is also moved to the side of the endoscope 107. At this time, a part of the dirt is flipped due to the elastic force of the wiper projection section 158. If the dirt cannot be removed by such one cleaning operation, the operation for advancing and retracting the endoscope 107 relative to the wiper projection section 158 is repeated.

Figure 29:
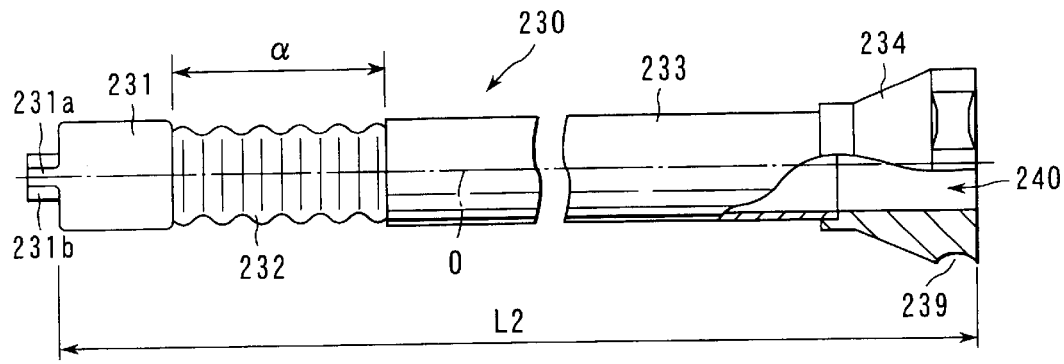
FIG. 29 is a side view showing an endoscope dirt remover according to a ninth embodiment of the present invention.
Figure 30:
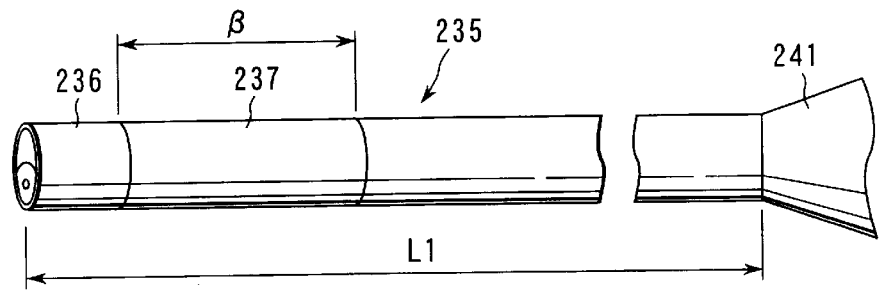
FIG. 30 is a side view showing an endoscope used in combination with the endoscope dirt remover shown in FIG. 29.
Figure 31A:
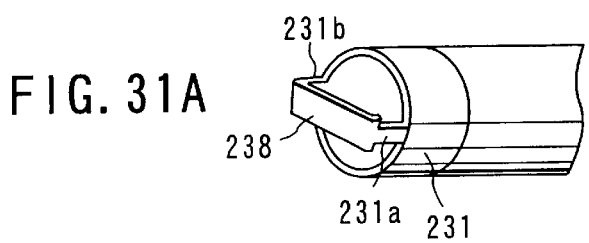
FIG. 31A is a perspective view showing a distal section of the endoscope dirt remover shown in FIG. 29.
Figure 31B:
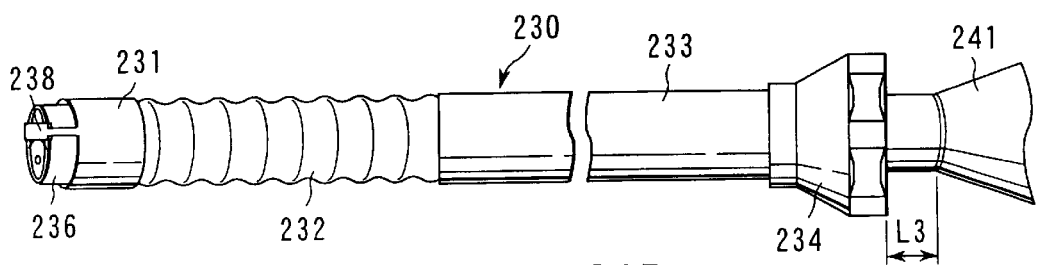
FIG. 31B is a side view showing a state when the endoscope shown in FIG. 30 is inserted into the endoscope dirt remover shown in FIG. 29.
Figure 32A:
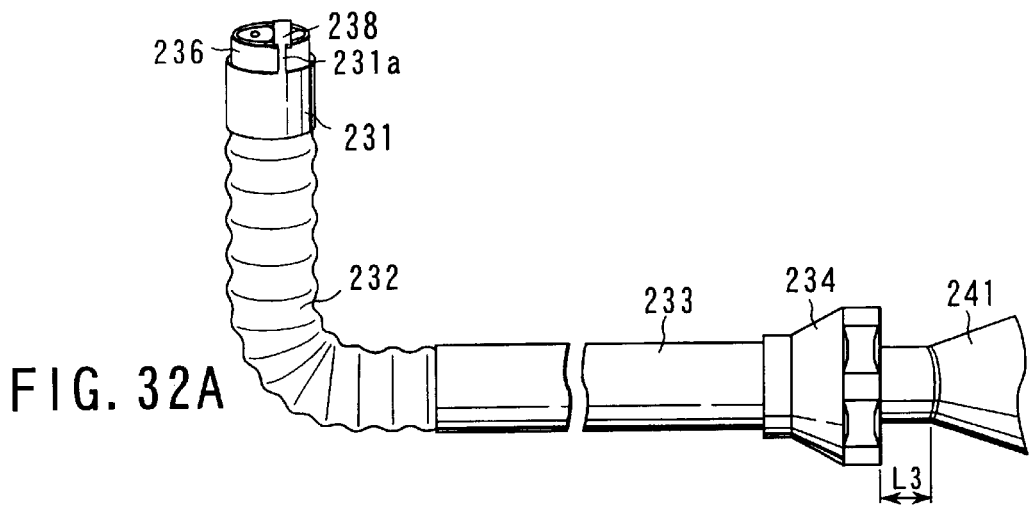
FIG. 32A is a perspective view showing a state when a curved section of the endoscope is curved in the state shown in FIG. 31B.
Figure 32B:
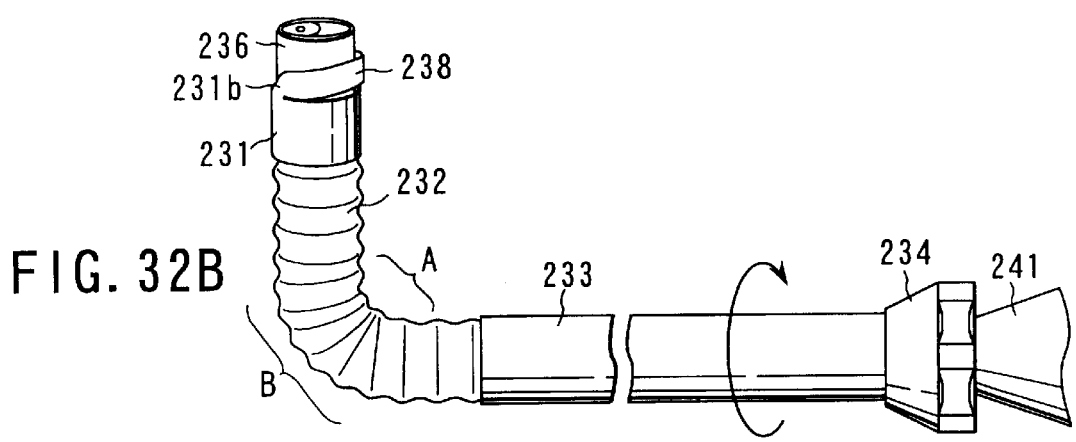
FIG. 32B is a perspective view showing a state in which the endoscope dirt remover is rotated relevant to the endoscope in the state shown in FIG. 31A.

FIG. 29 to FIG. 33 each show a ninth embodiment of the present invention. An endoscope dirt remover according to the present embodiment is used together with an endoscope 235 as shown in FIG. 30. The endoscope 235 is a direct viewing endoscope that has a curved section 237 at a part of its tip end side, and has its flat tip end face. The length of the curved section 237 of the endoscope 235 is set to β, and the length of an insert section of the endoscope 235 is set to L1. The taper-shaped breakage stop member is provided to the proximal side portion of the insert section of the endoscope.

As shown in FIG. 29, an endoscope dirt remover 230 according to the present embodiment is composed of: a distal section 231; a grip section 234; an insert tube section 233; and a curved section 232. The configuration of the distal section 231 is different from the distal section 3 according to the second embodiment in the points raised below.

Rise sections 231a and 231b communicate with an abutment section 238 having a projection which abuts against a lens face at a tip end of the endoscope 235, and these rise sections 231a and 231b are different from each other in width. Specifically, the width of the rise section 231a is set to be smaller than that of the rise section 231b (refer to FIG. 31). In addition, although the rise sections 231a and 231b may be different from each other in thickness (in this case, it is desirable that the thickness of the rise section 231b is greater than that of the rise section 231a), the thickness of these sections are equal to each other in the present embodiment. Thus, these connecting portion i.e., the rise sections 231a, 231b are designed so that the amounts of the elastic deformation of the rise sections 231a, 231b are different from each other when the same load is applied to the rise sections 231a, 231b. In addition, the abutment section 238 is shifted slightly one-sidedly (upwardly in FIG. 29) relevant to the center axis O.

The curved section 232 forms a so-called bellows tube structure. The bellows tube is a structure in which its waveform shapes are continuous, has a predetermined strength in a compression/distortion direction, and can be curved in an arbitrary direction. It is preferable that the bellows tube is formed of a material whose shape is properly deformed such as Teflon or urethane based materials. The curbed section 232 is fixedly bonded to the distal section 231 and the insert section 233. A length α of the curved section 232 is greater than a length β of the curved section 237 of the endoscope 235. Therefore, the curved section 237 of the endoscope 235 is designed so that it is always arranged inside of the curved section 232 of the endoscope dirt remover 230 when the endoscope dirt remover 230 is combined with the endoscope 235.

On the other hand, the insert tube section 233 is a hard tubular member, and its inner hole communicates with the grip section 234, and is fixedly bonded to the grip section 234. The grip section 234 has a plurality of recesses 39 at its periphery so as to easily rotate the grip section, and is easily gripped in shape. In addition, an insert hole 240 through which the endoscope 235 can be inserted is formed at the substantial center of the grip section 234. This insert hole 240 communicates with an inner hole of the insert tube section 233, an inner hole of the curved section 232, and an inner hole of the tip end section 231. The full length L2 of the endoscope dirt remover 230 is shorter than the length L1 of the insert section of the endoscope 235.

Now, a description will be given with respect to a method for removing the dirt on a lens face of the endoscope 235 by using the endoscope dirt remover 230 according to the present embodiment.

First, the endoscope 235 is inserted through the insert hole 240 of the dirt remover 230. In this case, the endoscope 235 is inserted until the distal section 236 of the endoscope 235 abuts against the abutment section 238 of the dirt remover 130 (refer to FIG. 31B). At this time, the full length L2 of the dirt remover 230 is shorter than the full length L1 of the insert section of the endoscope 235. Thus, the dirt remover 230 can be slid in an axial direction relevant to the endoscope 25 by a distance L3 between the proximal section of the dirt remover 230 and a breakage stop 241 of the insert section of the endoscope 235. In the state shown in FIG. 31B, the dirt remover 230 and the endoscope 235 are inserted into the endoscope guide tube that is generally used in surgical operation, and the distal section of the endoscope 235 is inserted into the body.

After the endoscope 235 has been inserted into the body, the abutment section 238 is retracted to the outside of the field of view in accordance with the procedures below. That is, the grip section 234 of the dirt remover 230 is gripped, and the dirt remover 230 is slid in its proximal end direction by the distance L3 relevant to the insert section of the endoscope 235. In this manner, the abutment section 238 is pushed out to its tip end side by the distal section 236 of the endoscope 235, and thus, the rise sections 231a and 231b extends to the tip end side. The dirt remover 230 is slid to the proximal end side by the distance L3, and thus, the grip section 234 is rotated. In this case, the rotation direction is clockwise viewed from the proximal end side. This rotation force is transmitted from the grip section 234 to the tube section 233 and the curved section 232. At this time, the curved section 234 is strong in the distortion direction, and thus, the rotation force can be transmitted to the distal section 231.

Figures 33A, 33B, 33C:
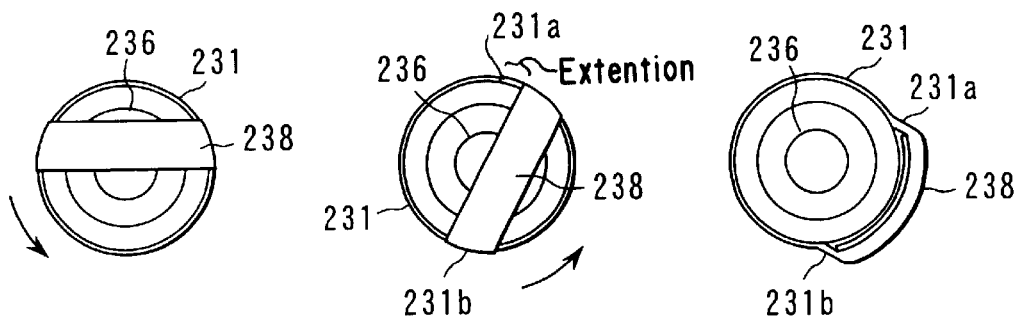
FIG. 33A is a front view showing the endoscope dirt remover in the state shown in FIG. 32A.
FIG. 33B is a front view showing the endoscope dirt remover in a state between the state of FIG. 32A and the state of FIG. 32B.
FIG. 33C is a front view showing the endoscope dirt remover in the state shown in FIG. 32B.

When the distal section 231 of the dirt remover 230 rotates, the abutment section 238 makes movement as shown in FIG. 33 relevant to the distal section 236 of the endoscope 235. That is, first, the distal section 231 rotates in the direction indicated by the arrow shown in FIG. 33A. Then, the rise section 231b moves in the direction indicated by the arrow, and concurrently, the abutment section 238 also moves in the direction indicated by the arrow. On the other hand, the rise section 231a is small in width, and thus, only the rise section 231a extends in the rotation direction while the abutment section 238 does not follow movement of the rise section 231a so strictly (refer to FIG. 33B). In this manner, the abutment section 238 is arranged at a position eccentric to the tip end of the endoscope 235. Here, a tension is applied to the rise sections 231a and 231b to be slid by the distance L3 so that the abutment section 238 tends to move to the proximal end side of the dirt remover 230. Therefore, when the distal section 231 is further rotated from this state, the abutment section 238 positioned eccentrically relevant to the tip end of the endoscope 235 is moved to the proximal end side due to the tension, and finally, is retracted to the side face of the distal section 236 of the endoscope 235. In this manner, when the rise sections 231a, 231b are different from each other in thickness and the distal section 231 is rotated, the dirt can be removed even in the direct viewing endoscope.

The endoscope 235 can be curved at its tip end side, and surgical operation under the endoscope can be carried out under the field of view in which the curved section 237 is arbitrarily curved. At this time, the curved section 237 of the endoscope 235 is arranged inside of the curved section 232 of the dirt remover 230. Thus, when the endoscope 235 is curved, the curved section 232 is curved in accordance with a curving operation of the endoscope 235. In the curved state of the bellow tube of the curved section 232, the waveform shape of the curved inside (section A shown in FIG. 32B) is compressed, and the waveform shape of the curved outside (section B shown in FIG. 32B) positioned at the opposite side extends. In this manner, the dirt remover 230 can be curved without losing the curving of the endoscope 235.

If the dirt adheres to the lens face of the endoscope 235, the grip section 234 is gripped, and the dirt remover 230 is advanced in the tip end direction of the endoscope 235. At this time, the pushing force acting to the grip section 234 transmits the tube section 233 and the curved section 232, and the distal section 231 of the dirt remover 230 is moved in its tip end direction. As described above, the curved section 232 having its bellows shape is strong in force in the compression direction, and thus, the distal section 231 can be reliably moved in its tip end direction. After the abutment section 238 of the distal section 231 has been successfully positioned on the front face of the distal section 236 of the endoscope 235 due to such an operation, the dirt remover 230 is rotated after slid toward the proximal end side by the distance L3, as described above. Then, the abutment section 238 is retracted to be moved in abutment with the lens face at the tip end of the endoscope 235. This operation is carried out repeatedly, thereby removing the dirt on the lens face.

Figure 34A:
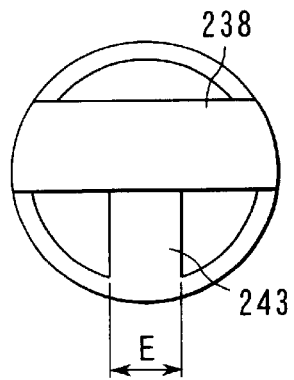
FIG. 34A is a front view showing a distal section according to a modified example of the distal section of the endoscope dirt remover shown in FIG. 29.
Figure 34B:
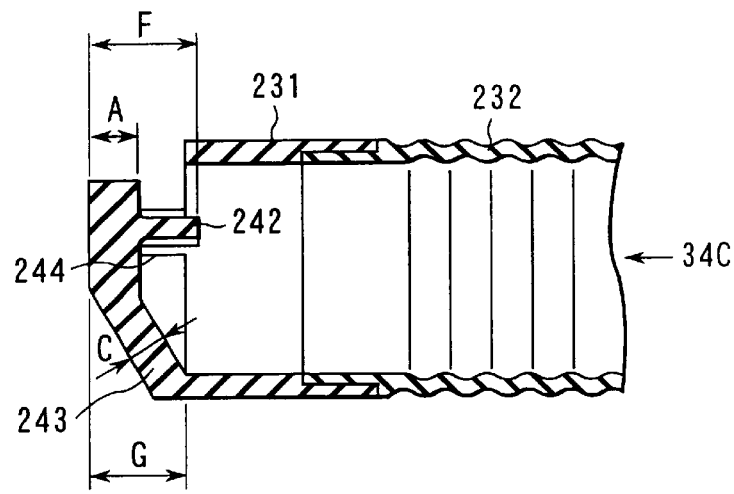
FIG. 34B is a sectional view showing the distal section shown in FIG. 34A.
Figure 34C:
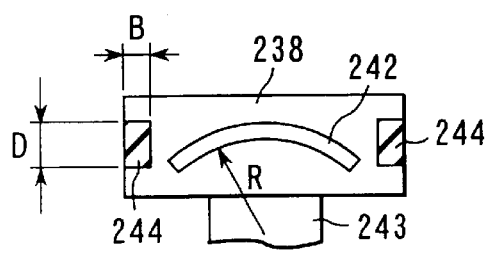
FIG. 34C is a view seen in the direction indicated by the arrow 34 shown in FIG. 34B.

FIG. 34A to FIG. 34C each show a modified example of the distal section 231 of the dirt remover 230. Although a distal section 231 according to this modified example has a configuration substantially identical to that according to the sixth embodiment, they are different from each other in the point raised below.

Thickness A of an abutment section 238 is larger than thickness B of a rise section 244. In addition, thickness C of an auxiliary plate 243 is larger than the thickness B of the rose section 244. In addition, a width E of the auxiliary plate 243 is sufficiently large than a width D of the rise section 244. A projection section 242 on the abutment section 238 abutting against the lens of the endoscope 235 forms an arch shape having an arbitrary curvature R. In addition, a length F of the projection section 242 is greater than a projection length G from the distal section of the abutment section 238.

Now, actuation of the above constructed distal section 231 will be described here.

The procedures for inserting the dirt remover 230 into the endoscope 235 are as described above. First, the endoscope 235 is inserted into the dirt remover 230 until the distal section 236 of the endoscope 235 has abutted against the projection section 242 of the abutment section 238. Then, the dirt remover 230 is guided into the body together with the endoscope 235 via the endoscope guide tube generally used in surgical operation.

After the dirt remover 230 has been inserted into the body, the abutment section 238 is retracted out of the field of view with the following procedure. That is, the grip section 234 is gripped, and only the dirt remover 230 is slide in the proximal end direction. In this manner, the projection section 242 first upwardly abuts against the lens face of the endoscope 235. When the dirt remover 230 is further moved to the proximal end side from this state, a part of the auxiliary plate 243 downwardly abuts against the lens face of the endoscope 235. In this case, the length F of the projection section 242 is greater than the projection length G from the distal section of the abutment section 238. Thus, after the projection section 242 has abutted against the lens face of the endoscope 235, a part of the auxiliary plate 243 abuts against the lens face of the endoscope 235. Therefore, the projection section 242 can be abutted upwardly of the lens face before causing an effect of downward displacement of the projection section 242 due to deformation of the rise section 244 or auxiliary plate 243. In addition, since the projection section 242 forms a shape having an arbitrary curvature R, as shown in FIG. 34C, the projection section 242 can be abutted more upwardly of the lens at the center of the lens to be wiped most. Therefore, a failure to wipe (or non-uniform wiping) can be prevented.

When the dirt remover 230 is further moved to the proximal end side from the state, the distal section 231 and the abutment section 238 are deformed. The rise section 244 is smaller than the auxiliary plate 243 in thickness and in width, the rise section 244 positively extends in its tip end direction. On the other hand, since the auxiliary plate 243 extends more hardly than the rise section 244 in shape, the auxiliary plate 243 does not extend so much in the tip end direction, and is deformed downwardly in FIG. 34B. In this manner, the abutment section 238 communicating with the auxiliary plate 243 is pulled toward the auxiliary plate 243, and moves downwardly. Finally, the abutment section 238 moves to the side face at the tip end of the endoscope 235 due to the downward tension of the auxiliary plate 243 and the elastic force of the rise section 244. In addition, in a process in which the abutment section 238 thus moves on the lens face from the upward direction to the downward direction, the projection section 242 moved on the lens face of the endoscope 235 from the upward direction to the downward direction. Since the thickness A of the abutment section 238 is greater than that of the rise section 244, the abutment section 238 is hardly deformed. Namely, in a process in which the abutment section 238 moves, the shape of the projection section 242 is not deformed, and the abutment state of the projection section 242 against the lens face can be constantly maintained. Then, surgical operation under the endoscope is carried out in the same manner as described above. When a tip end of the endoscope 235 is operated to be curved, the curved section 232 of the dirt remover 230 is curved in accordance with this operation.

Procedures for removing the dirt while the endoscope 235 is curved will be described below.

First, the grip section 234 is gripped, and the dirt remover 230 is slid in its tip end direction. How the force applied to the grip section 234 is transmitted to the distal section is as described above. Therefore, the abutment section 238 moves from the side face of the distal section of the endoscope 235 to the front face thereof. Next, the grip section 234 is slid to the proximal end side relevant to the endoscope 235. In this manner, as described above, the projection section 242 of the abutment section 238 moves upwardly and downwardly on the lens face of the endoscope 235, and wipes the dirt. That is, the dirt on the lens face of the endoscope 235 having a flat face can be wiped out at the projection section 242 by merely moving the dirt remover 230 forth and back.

FIG. 35A to FIG. 35D each show an endoscope dirt remover 300 according to a tenth embodiment of the present invention. This endoscope dirt remover 300 comprises: a distal section 301 having an inner hole; a pipe section 302 having an inner hole through which the endoscope can be inserted; and a grip section 303 at its proximal end side. The distal section 301 is molded of an elastic member, and is molded integrally with the tip end side of the pipe section 302. Although a portion of the distal section 301 molded integrally with the pipe section 302 is not deformed, the other portions of the distal section 301 can be deformed. Hereinafter, this portion is referred to as a retracting section 319. The distal section 301 is formed in a substantially tube shape having an inner hole. The distal section 301 is made of silicon based- or urethane based-elastic material. In addition, a tapered section 310 is provided on the outer face at the tip end of the retracting section 319.

The distal section 301 has an observation hole 304 that is a through hole at its inside. In addition, an opening portion 309 is provided at the retracting section 319 at its side face. This opening portion 309 extends in direction (indicated by the arrow A shown in FIG. 36) vertical to a center axis O of the pipe section 302. The opening shape of the opening portion 309 may be formed in a rectangular shape (opening width is F1), as shown in FIG. 37A or may be formed in a triangular shape (opening width is F2), as shown in FIG. 37B.

The thickness of the retracting section 319 differs in the side of the opening portion 309 and its opposite side. That is, as shown in FIG. 36B, the thickness at the upper side of the retracting section 319 positioned at the side of the opening portion 309 is set to t1, and the thickness of other sites (range in a peripheral direction of an angle θ6 shown in FIG. 35A) of the retracting section 319 is set to t2. A relationship between t1 and t2 is t1>t2. The inner diameter D' of a site positioned between the portion being molded integrally with the pipe section 302 and the opening portion 309 may be defined to be equal to or greater than the outer diameter of the endoscope. However, the inner diameter D' may be slightly smaller than the outer diameter of the endoscope.

Figure 36A:
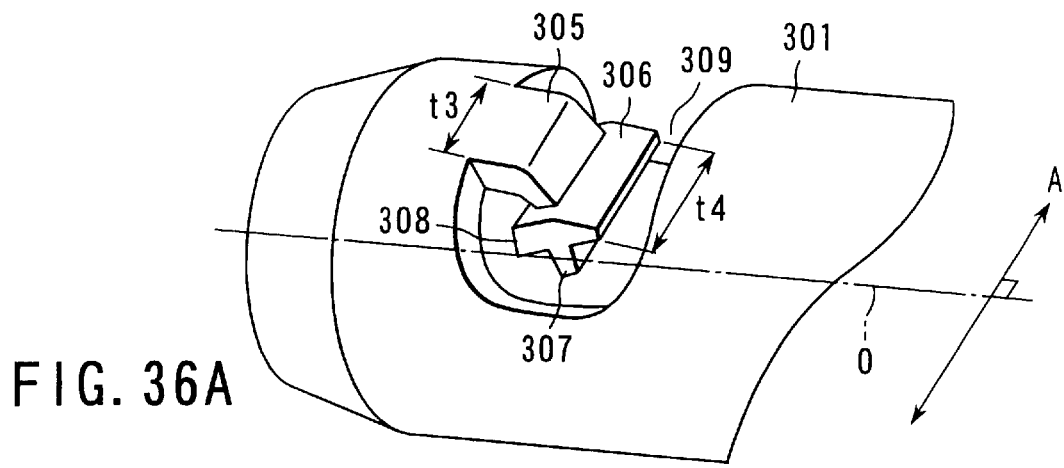
FIG. 36A is an enlarged perspective view showing the distal section of the endoscope dirt remover shown in FIG. 35A.
Figure 36B:
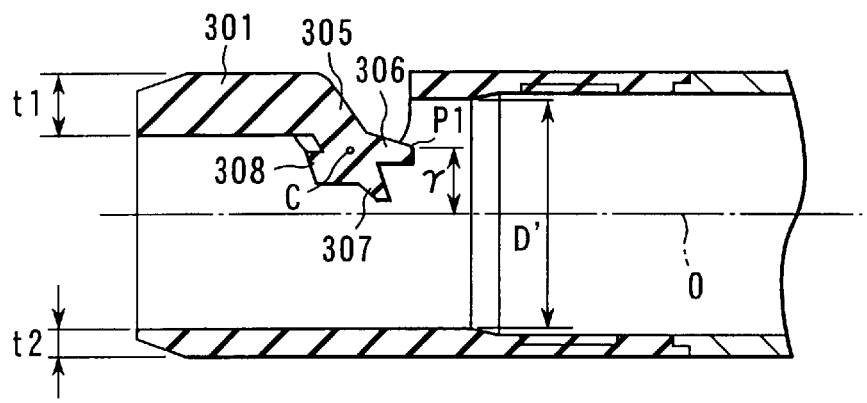
FIG. 36B is a sectional view showing the distal section shown in FIG. 36A.
Figure 37A:
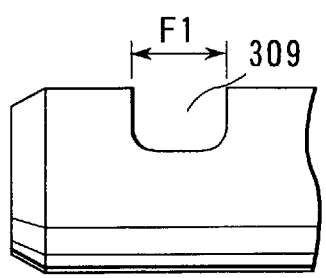
FIG. 37A is a schematic view showing an opening shape of the distal section of the endoscope dirt remover shown in FIG. 35A.
Figure 37B:
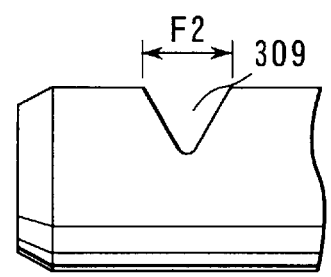
FIG. 37B is a schematic view showing another opening shape of the distal section of the endoscope dirt remover shown in FIG. 35A.

As shown in FIG. 36A an FIG. 36B, the retracting section 319 has an arm 305 which Protrudes from a Site Whose Thickness Is T1 Inwardly in Radial Direction (In the Direction of the inner hole). The arm 305 extends inwardly with a predetermined angle from the opening portion 309 to the center axis O, and the width is set to t3. Namely, one end of the arm 305 is coupled with a side face of the retracting section 319, and the other end of the arm 305 extends with a predetermined angle in the direction of the center axis O of the pipe section 302. Hereinafter, an end portion of the arm 305 positioned at the center axis O is referred to as "tip end". In addition, the center of the tip end of the arm 305 is indicated by C in FIG. 36B. At the tip end of the arm 305, there are molded: a wiper blade, i.e., a first projection 306 extending substantially in parallel to the center axis O of the pipe section 302; a second projection 307 extending with a predetermined angle clockwise relevant to the first projection 306; and a restricting section 308 positioned opposite to the first projection 306 by substantially 180 degrees around the center C of the tip end of the arm 305. Of the tip end of the first projection 306, a portion first abutting against the tip end of the endoscope is indicated by P1 in FIG. 36B. This portion P1 is spaced by a predetermined distance γ from the center axis O of the pipe section 302. As seen. it has a length dimension "t4" that is substantially greater than its thickness or width dimension (measured perpendicularly to the length "t4"). whereby it is line-like in shape. This line-like portion constitutes the lens wiping blade. The first projection 306, the second projection 307, and the restricting section 308 are defined as t4 in width, and vertically extends relevant to the center axis O in the opening portion 309. In addition, the first projection 306, the second projection 307, and the restricting section 308 are integrally structured, and are more rigid than the arm 305. In addition, a site of the retracting section 319 positioned at the side of the opening portion 309 and the arm 305 are defined as t1 in thickness, and is more rigid than any other portion of the retracting section 319 whose thickness is t2. A relationship between t3 and t4 may be t3 =t3, but is preferably t3<t4.

Figure 38A:
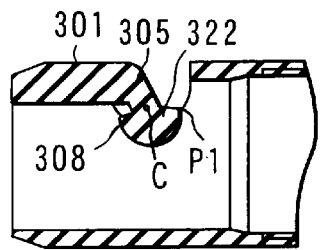
FIG. 38A is a sectional view showing a first modified example of a wiper blade at the distal section of the endoscope dirt remover shown in FIG. 35A.
Figure 38B:
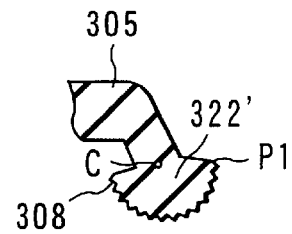
FIG. 38B is a sectional view according to a second modified example showing a wiper blade at the distal section of the endoscope dirt remover shown in FIG. 35A.

Modified examples of the projections 306, 307 and the restricting section 308 are shown in FIG. 38A and FIG. 38B. The projections 306, 307 and the restricting section 308 may form a projection 322 whose sectional view is integrally formed in an arc shape, as shown in FIG. 38A. In addition, as shown in FIG. 38B, these projections may form a sectional arc shape integrally, and may form a projection 322' having irregularities on its arc. The centers of these arcs each coincide with the center C at the tip end of the arm 305, but may not coincide with the center C. In addition, both projections 322 and 322' have: a portion P1 first abutting against a tip end of the endoscope; and a restricting section 108 positioned opposite to the portion P1 by substantial 180 degree around the center C. In this case as well, the portion P1 is positioned in distance γ from the center axis O of the pipe section 302.

Figure 39:
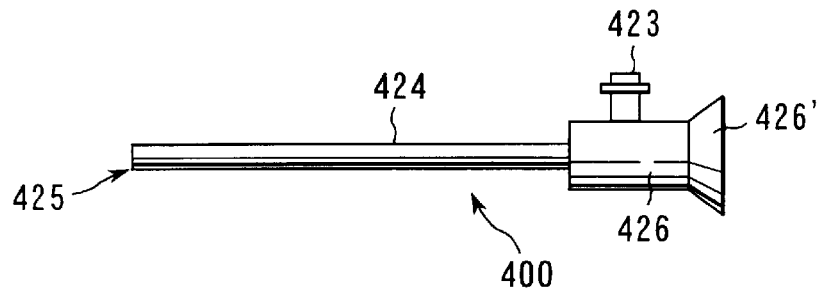
FIG. 39 is a side view showing the endoscope.

An endoscope 400 used with the endoscope dirt remover 300 is shown in FIG. 39. As shown in the figure, the endoscope 400 has: an insert section 424 inserted into a cavity; a distal section 425 having a lens face for observing the inside of the cavity at its tip end; a main body section 426 provided at a proximal end of the insert section 424; and a light guide post (hereinafter, referred to as LG post) 423 positioned on the main body section 426, the post being adopted to guide light from an external light source to the tip end side of the endoscope 400. The LG post 423 is protruded vertically from the main body section 426 of the endoscope 400. In addition, an eyepiece section 126' is provided at the proximal end of the main body section 426 of the endoscope 400.

Figure 40A:
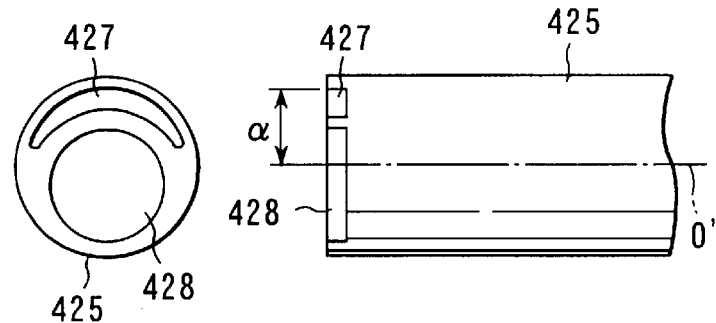
FIG. 40A is a side view and a front view showing a direct viewing endoscope.
Figure 40B:
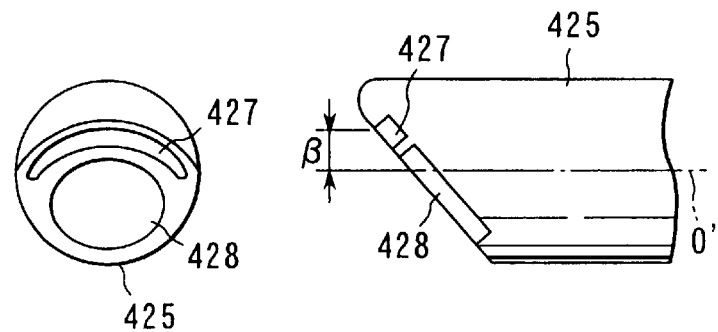
FIG. 40B is a side view and a front view showing an oblique viewing endoscope.

FIG. 40A shows the distal section 425 of the direct viewing type endoscope 400. In addition, FIG. 40B shows the distal section 425 of the oblique viewing type endoscope 400. As shown in FIG. 40A, a tip end face of the distal section 425 of the direct viewing type endoscope 400 is formed as a face vertical to a center axis O' of the endoscope insert section 424. An observation lens face 428 and a light face 427 for emitting the light guided from the LG post 423 to the outside are provided at the distal section 425. A distance between the center axis O' of the endoscope insert section 424 and the upper rim of a light face 427 is defined as α. On the other hand, as shown in FIG. 40B, the tip end face of the pug end portion 425 of the oblique viewing type endoscope 400 is formed as an inclined face that forms a predetermined angle other than an angle vertical to the center axis O' of the endoscope insert section 424 as the direct viewing type. The lens face 428 and the light face 427 are provided at the distal section 425. A distance between the center axis O' of the endoscope insert section 424 and the upper rim of the light face 427 is defined as β. The distances α and β may often differ from each other in general. In the present embodiment, the distance α is defined to be greater than the distance β. In the present embodiment, the light face 427 is provided at the side identical to the LG post 423 (upward side shown in the figure).

In the present embodiment, when the endoscope insert section 424 is arranged inside of the pipe section 302, a design is made so that the center axis O of the pipe section 302 substantially coincides with the center axis O' of the insert section. In addition, a distance γ between the center axis O of the pipe section 302 and the portion P1 is designed so as to be coincide with a greater one of the distances α and β (That is, the distance γ coincides with the distance α in the present embodiment).

As shown in FIG. 35A to FIG. 35D, an assembling section 303' capable of being assembled by inserting the pipe section 302 is provided at the tip end side of the grip section 303 of the endoscope dirt remover 300. In addition, a housing section 314 having a space capable of housing the main body section 426 of the endoscope 400 is provided at the proximal end side of the grip section 303. An endoscope insert hole 315 through which the endoscope insert section 424 can be inserted is provided at the tip end side of the housing section 314. Further, a guide section 313 (cutout-shaped) through which the LG post 423 of the endoscope 400 can be inserted is formed on the side face of the grip section 303. The grip section 303 is integrally formed of a hard elastic element. This hard elastic element is probe to be deformed by external force if the element is small in thickness and to be hardly deformed if the element is large in thickness. Such elastic element can include a silicon element urethane-based element and compound thereof.

Figure 35A:
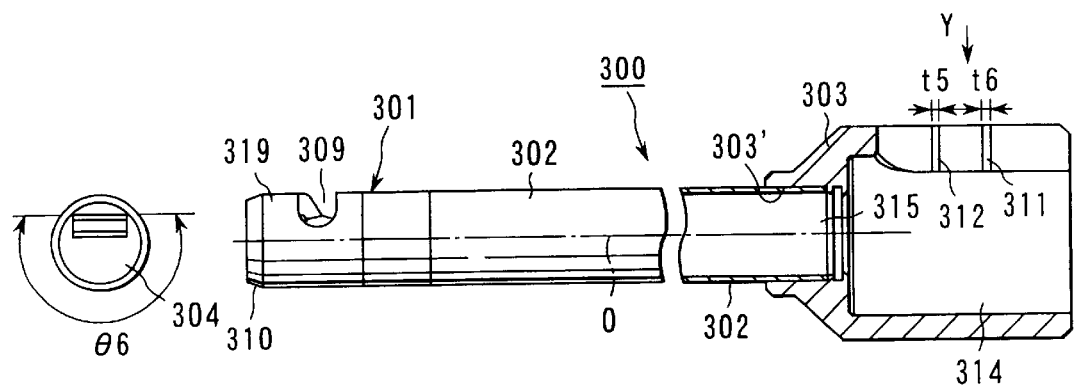
FIG. 35A is a side sectional view and a front view showing an endoscope dirt remover according to a tenth embodiment of the present invention.
Figure 35B:
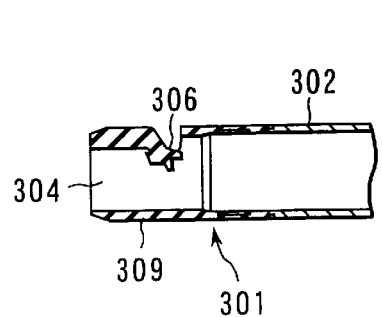
FIG. 35B is a sectional view showing a distal section of the endoscope dirt remover shown in FIG. 35A.
Figure 35C:
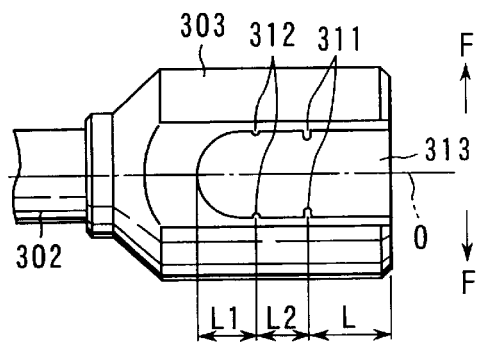
FIG. 35C is a plan view showing a grip section of the endoscope dirt remover shown in FIG. 35A.

A view indicated by the arrow in the Y direction in FIG. 35A is shown in FIG. 35C. As shown in FIG. 35C, the first stoppers 311, 311 and the second stoppers 312, 312 which are protruded inwardly are provided at the guide section 313. These stoppers 311 and 312 are provided in pair at both sides of the center axis O of the guide section 313. The projection quantity of the first stoppers 311 at the proximal end side is greater than that of the second stoppers 312 at its tip end. As shown in FIG. 35A, the thickness of the first stoppers 311 are set to t6, and the thickness of the second stoppers 312 are set to t5. In this case, a relationship between t5 and t6 is t5≦t6. The thicknesses t5 and t6 of the stoppers 311 and 312 are defined so that the stoppers 311 and 312 can be deformed when an external force F is applied to the guide section 313. In addition, the guide section 313 can be slightly deformed at its periphery in the direction of the external force F. The width of the guide section 313 is defined to be slightly greater than the outer diameter of the LG post 423. Each of a distance between the stopper 311 and the stopper 311 and a distance between the stopper 312 and the stopper 312 is slightly smaller than the outer diameter of the LG post 423.

The first stopper 311 is arranged at a position with a distance L from the proximal end of the grip section 303 (namely, release side of the guide section 313). The second stopper 312 is arranged at a position with a distance L2 from the first stopper 311. A distance between the second stopper 312 and the guide section 313 is defined as L1. Each of the distances L1, L2, and L is designed so that the LG post 423 can be housed in the range of each distance. A distance between the first stopper 311 and the portion P1 is slightly smaller than a distance between the tip end of the endoscope and the LG post 423 abutting against the first stopper 311. These distances L1, L2, and L are designed so that the LG post 423 is arranged at its optimal position while the endoscope 400 and the remover 300 are combined with each other. A detailed description will be given with reference to the associated using method described later.

Figure 35D:
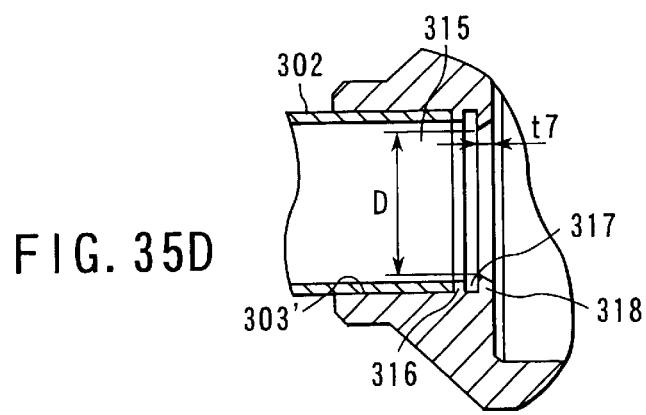
FIG. 35D is an enlarged sectional view showing a tip end side of the grip section of the endoscope dirt remover shown in FIG. 35A.

As shown in FIG. 35D, at the proximal end side of the endoscope insert hole 315, there are provided: a sealing section 316; a relief section 317 adjacent to the sealing section 318; a positioning section 316 adjacent to the relief section 317 and communicating with an assembling section 303' relevant to the pipe section 302. These sections 316, 317, and 318 are provided all over the periphery of the grip section 303. The inner diameter of the positioning section 316 is slightly greater than that of the pipe section 302, and is smaller than the outer diameter of the pipe section 302. In addition, the inner diameter D of the sealing section 318 is smaller than the outer diameter of the endoscope insert section 424. The inner diameter of the relief section 317 arranged between the positioning section 316 and the sealing section 318 is greater than that of the sealing section 318 and the positioning section 316. With such a configuration in the positioning section 316, when the pipe section 302 and the grip section 303 are fixedly bonded with each other, even if the pipe section 302 is inserted into the assembling section 303' blindly, its insert depth is determined by the positioning section 316. Thus, the assembling properties are improved.

The shape of the proximal side portion of the sealing portion 318 is taper so as to be thinner toward the center axis O. The maximal thickness of the sealing portion 318 is set to t7 so as to deform by an external force.

An endoscope guide tube 500 used in combination with the endoscope dirt remover 300 according to the present embodiment is shown in FIG. 41A and FIG. 41B. As shown in the figures, the endoscope guide tube 500 comprises: an insert section 501 introduced into a cavity through a body wall; a distal section 502 formed at a tip end of the insert section 501; a main body 504 contiguously provided at the proximal end side of the insert section 501; an air tightness valve 502 provided inside of the main body section 504; a hole 505 provided at the proximal end side of the main body section 504 and capable of having the remover 300 inserted thereinto; and an intimate contact section 510 fixed into the hole 505 and consisting of an elastic element. The endoscope guide tube 500 has a through hole capable of having the remover 300 inserted thereinto from the hole 505 at the proximal end side to the tip end side of the insert section 501 (this hole is generally interrupted by the air tightness valve 503). The air tightness valve 503 is formed by an elastic element which is deformed if an external force is applied. A slit 506 is provided at the center of the air tight ness valve 503, and the peripheral end portion of the air tightness valve 503 is fixedly bonded with the main body section 504. Namely, if an external force is applied to the slit 506, the slit 506 is opened after deformed. However, if the external force is not applied, the slit 506 is maintained to be closed. Even if the external force is applied, the peripheral end portion of the air tightness valve 503 is not deformed. In FIG. 41, a tip end of the insert section 501 is inclined relevant to the center axis O, but may be vertical to the center axis O.

The air tightness valve 503 shown in FIG. 41 is a so called duck bill valve, but may form a configuration as shown in FIG. 42. That is, an air tightness valve 503A shown in FIG. 42 comprises: a stop plate 509 which turns around a fulcrum 508; and a plate spring 507 biased in a direction in which the stop plate 509 is closed. In FIG. 42A, the stop plate 509 closes the hole 505 upon the receipt of the biasing force of the plate spring 507. If the external force is applied to the stop plate 509, the stop plate 509 turns in a direction A around the fulcrum 508 so that the inner hole of the insert section 501 is opened over its full length. In general, an intimate contact section 510 formed of an elastic element is provided around the hole 505, as shown in FIG. 42. This intimate contact section 510 is fixed to the periphery of the hole 505. A small hole 511 which is smaller than the hole 505 is formed at the center of the intimate contact section 510. This small hole 511 is smaller than the outer diameter of a device to be inserted into the guide tube 500. When the device is inserted, the small hole 511 comes into substantially intimate contact with an outer face of the device.

Now, actuation of the above configuration will be described here. A description will be primarily given with respect to the direct viewing type endoscope 400 and the endoscope guide tube 500 with the duck bill valve constitution.

Before starting surgical operation under the endoscope, the endoscope dirt remover 300 and the endoscope 400 are combined with each other, and preoperative preparation is carried out. At first, the insert section 424 of the endoscope 400 is inserted through the endoscope insert hole 315 of the remover 300. A so-called camera head communicating with an external television device is connected to a proximal end of an eyepiece section 426'. An image acquired through the lens face at the distal section 425 of the endoscope 400 is transmitted to the eye piece section 426'. This transmitted image (so called endoscope image) is transmitted to the camera head, and is displayed on the external television device. When the insert section 424 of the endoscope 400 is inserted as described above, the sealing section 318 comes into substantially intimate contact with the outer face of the insert section 424 because its inner diameter D is smaller than the outer diameter of the insert section 424 of the endoscope 400. That is, the endoscope 400 and the remover 300 are combined with each other in their sealed state.

The sealing section 318 is integrally provided at the inside of the grip section 303, as described above. The grip section 303 and the sealing section 318 are formed of a hard elastic element. The maximum thickness t7 of the sealing section 318 is small. In addition, the sealing section 318 is formed in an inclined shape in which its inner diameter is smaller at its tip end side. Thus, the thickness is smaller at the tip end side. A hard elastic element forming the sealing section 318 is prone to be easily deformed if the element is small in thickness, and thus, the sealing section 318 is deformed by the applied external force. In addition, the relief section 317 adjacent to the sealing section 318 is greater than the inner diameter of the sealing section 318, and thus, is provided as a space when the sealing section 318 is formed in the tip end direction. Therefore, Since the sealing section 318 is further easily deformed at the tip end side, the inner diameter of the sealing section 318 is expanded according to outer diameter of the insert section of the endoscope so as to maintain seal condition. Assume that the through resistance of the endoscope 400 passing though the sealing section 318 is R1.

When the insert section 424 of the endoscope 400 is further advanced, the insert section 424 is positioned at the inside of the pipe section 302. Then, the LG post 423 of the endoscope 400 is positioned at the proximal end side of the grip section 303. At this time, the LG post 423 is aligned with the release side of the guide section 423. When the endoscope 400 is further advanced in this state, the LG post 423 is arranged inside of the guide section 313. Finally, the LG post 423 comes into contact with the first stopper 311. The position of the LG post 423 at this time is indicated by dashed line in FIG. 43. At this time, the main body section 426 of the endoscope 400 is also arranged in the housing section 314 of the grip section 303. The first stopper 311 is provided at a position with the distance L from the proximal end of the guide section 313, and the LG post 23 is designed to be housed in the guide section 313. Thus, the LG post 423 does not come off from the guide portion 313. Here, assume that the through resistance when the LG post 423 passes through the first stopper 311 is R2.

When the LG post 423 is further moved in the tip end direction of the remover 300 while the LG post 423 comes into contact with the first stopper 311, the external force is applied to the stopper 311 by the LG post 423. As described above, the first stopper 311 is protruded with a width "t6" in the direction of the center axis O of the guide section 313, and can be deformed by the external force. Thus, when the first stopper 311 is deformed, the guide section 313 is also deformed in the direction of the external force F indicated by the arrow shown in FIG. 35C. Namely, the through resistance R2depends on the deformation force quantity of the first stopper 311 and that generated around the guide section 313.

If the LG post 423 is arranged at a position indicated by dashed line shown in FIG. 43, the distal section 425 of the endoscope 400 is arranged in the inner hole of the distal section 301 (refer to FIG. 44). At this time, the portion P1 of the first projection section 306 first abutting against the tip end of the endoscope 400 is distant by a distance t8 from the tip end of the endoscope 400. Namely, when the LG post 423 is arranged at a position indicated by dashed line shown in FIG. 43, the first projection section 306 does not come into contact with the distal section 425 of the endoscope 400. At this time, as shown in FIG. 45A, the observation hole 304 is positioned in the range of a viewing angle θ of the endoscope 400. The endoscope image at this time is shown in FIG. 45B. The projection sections 306 and 307 can be verified upwardly of FIG. 45B, and the observation hole 304 can be verified downwardly of the figure. The observation hole 304 is provided as a through hole communicating with the outside, thus making it possible to verify the external state through the observation hole 304 through the endoscope image.

The preoperative preparation is completed while the first stopper 311 and the LG post 423 come into contact with each other (a state indicated by dashed line shown in FIG. 43). In this state, surgical operation under the endoscope is started, the insert section 501 of the endoscope guide tube 500 is inserted into the body wall, and the distal section 502 is disposed in abdominal cavity or thorax. In the present embodiment, a description will be given by exemplifying surgical operation under the endoscope in abdominal cavity. The surgical operation under the endoscope in the abdominal cavity is carried out while the inside of the abdominal cavity is inflated by pneumoperitoneum gas.

When the distal section 502 of the guide tube 500 is arranged in the abdominal cavity, an assembly of the remover 300 and the endoscope 400 is inserted into the guide tube 500. At this time, the distal section 301 of the remover 300 is inserted into the hole 505 of the endoscope guide tube 500. This operation is carried out while the main body section 426 of the endoscope 400 or the camera head at its proximal end is held. The insert section 424 of the endoscope 400 is intimately combined with the sealing section 318. At this tie, the through resistance R1 acts, the first stopper 311 and the LG post 423 come into contact with each other, and the LG post 423 is housed in the guide section 313. Therefore, the endoscope 400 is prevented from being contaminated, displaced back and forth, or rotated relevant to the dirt remover 300 with a small amount of force.

The tapered section 310 is provided at the outer face of the tip end of the distal section 301 of the remover 300. Thus, when the remover 300 is inserted into the hole 505 of the guide tube 500, the taper section 310 serves as a guide, whereby insertion is facilitated. At the intimate contact section 510 provided at the hole 505, its small hole 511 is deformed and increases in diameter. Finally, this small hole is substantially equal to, and comes into intimate contact with, the outer diameter of the dirt remover 300, thus enabling insertion without any problem and enabling to maintain the seal condition. When the dirt remover 300 is further inserted, the remover 300 passed through the valve section 503 of the guide tube 500. As described above, at the valve section 503, the slit 506 positioned at its center is deformed by external force. The slit 506 is deformed to the external shape of the dirt remover 300, and is combined substantially intimately. Therefore, the dirt remover 300 can pass through the valve section 503. In case of the valve section 503A with a spring structure, if the external force is applied to the stop plate 509 as described above, the spring 507 is deformed. Then, the plate 509 moves in its tip end direction around the fulcrum 508 and communicates with the hole of the insert section of the guide tube 500. The resistance when the dirt remover 300 is inserted into the guide tube 500 is defined as R3. Namely, the insertion resistance R3 depends on a resistance when the dirt remover 300 passes through the intimate contact section 510 of the hole 505 and a resistance when the remover passed through the air tightness section 503. In the valve section 503A with a spring structure, the insertion resistance is defined as R3'. A relationship between the insertion resistance R3 (R3') and the previously described through resistances R1 and R2 is R1+R2>R3 (R3'). Namely, R1+R2 is greater than R3. Therefore, when the dirt remover 300 is inserted into the guide tube 500, even if the remover 300 is inserted while a proximal end (or camera head) of the main body section 426 of the endoscope 400 is gripped, the LG post 423 does not pass through the first stopper 311 toward the distal end unintentionally. During insertion, the distal section 425 of the endoscope 400 does not come into contact with the projection section 306 unintentionally or does not push the projection 306 in its tip end direction. Therefore, in this state, the distal section of the endoscope abuts against the projection, the retracting section 319 of the distal section 301 is not deformed unintentionally, and thus, the dirt remover 300 is inserted into the guide tube 500 smoothly. Thus, the insertion properties are improved. In addition, since the distal section 425 of the endoscope 400 does not come into contact with the projection section 306 unintentionally in the guide tube 500, the retracting section 319 can be prevented from being deformed in the guide tube 500, Thus, the retracting section 319 can be prevented from being damaged in the guide tube 500.

In addition, at the dirt remover 300, the outer diameter of its pipe section 302 is intimately combined with the intimate contact section 510, and air tightness is maintained. Further, the outer diameter of the endoscope 400 is intimately combined with the sealing section 318 of the dirt remover 300, and thus, air tightness is maintained. Therefore, the pneumoperitoneum gas inflating the inside of the abdominal cavity does not leak to the outside even if the dirt remover 300 is inserted into the guide tube 500.

The distal section 301 of the dirt remover 300 passes through the inside of the insert section 501 of the guide tube 500, and finally, the distal section 301 is arranged at the inside of the abdominal cavity. It is possible to verify whether or not the distal section 301 is arranged at the inside of the abdominal cavity through the observation hole 304, as described above. Therefore, the distal section 301 does not come into contact with organ in the abdominal cavity unintentionally.

When it is verified by the observation hole 304 that the distal section 301 has been successfully arranged in the abdominal cavity, only the endoscope 400 is slid in the abdominal cavity direction relevant to the dirt remover 300, and the distal section 425 of the endoscope 400 is exposed from the inside of the distal section 301 to the inside of the abdominal cavity. First, the main body section 426 (or camera head) of the endoscope 400 and the grip section 303 of the dirt remover 300 are gripped, and the LG post 423 is moved in the tip end direction of the first stopper 311. At this time, the slide force quantity is applied by the resistance R2 when the first stopper 311 is passed. Then, this stopper 311 is deformed at the tip end side, and the guide section 313 is deformed in a widthwise direction (direction F described above). Thus, the LG post 423 passes through the first stopper 311. The position of the LG post 311 at this time is indicated by single dotted chain line. After the LG post 423 has passed through the first stopper 311, the widths of the first stopper 311 and the guide section 313 are restored in their original state by elastic force of the element. Here, the distance L2 between the first stopper 311 and the second stopper 312 coincides with the distance "t8" between the portion P1 of the first projection section 306 and the distal section of the endoscope 400 when the LG post is arranged at a position indicated by single dotted chain line shown in FIG. 43. Namely, where the LG post 423 is arranged at the position indicated by the single dotted chain line, the tip end of the endoscope 400 is positioned coming slight contact with the portion P1 of the first projection section 306 as shown in FIG. 47. When the LG post 423 is arranged at the position indicated by the single dotted chain line, the post 423 comes into contact with the second stopper 312. However, at this time, the retracting section 319 isn't deformed. Even when the LG post 423 passes through the first stopper 311, the post comes into contact with the second stopper 312. Thus, if the slide force quantity is not applied the LG post 423 does not move to a position at the tip end side (a position indicated by solid line shown in FIG. 46). The resistance when the LG post 423 passes through the second stopper 312 is defined as R4.

A slide force quantity of the resistance R4 is applied to the endoscope 400. Then, the LG post 423 passes through the second stopper 312, and is arranged at a position indicated by solid line shown in FIG. 46. The resistance R4 is smaller that R2 because the projection quantity of the second stopper 312 is smaller than that of the first stopper 311. That is, the LG post 423 can be slid more easily than the resistance R2 at a position indicated by solid line. When the LG post 423 passes through the second stopper 312, the deformation of this stopper 312 is the same as that of the first stopper 311 (the second stopper 312 is deformed at the tip end side, the width of the guide section 313 increases, and the LG post 42 pass through the stopper 312). Of course, the second stopper 312 is restored in its original state by elastic force of the element after the LG post 423 has passed through the stopper 312. When the LG post 423 is arranged at a position indicated by solid line, the tip end of the endoscope 400 is exposed to the inside of the abdominal cavity from the inside of the distal section 303 of the dirt remover 300.

Now, a process in which the distal section 425 of the endoscope 400 is exposed to the inside of the abdominal cavity from the inside of the distal section 301 of the dirt remover 300.

Figure 48A:
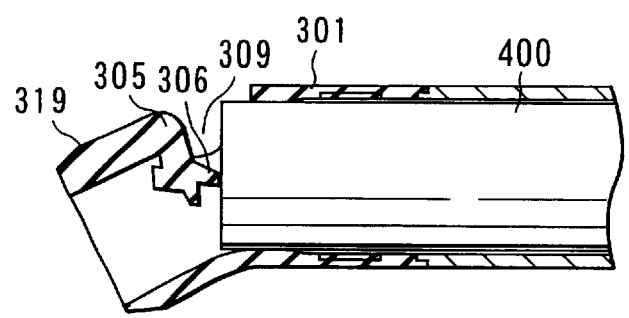
FIG. 48A is a sectional view showing a first actuation state when the endoscope is inserted into the endoscope dirt remover shown in FIG. 35A.
Figure 48B:
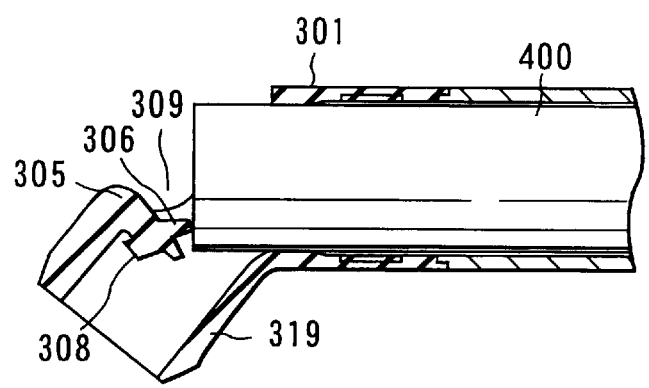
FIG. 48B is a sectional view showing a second actuation state when the endoscope is inserted into the endoscope dirt remover shown in FIG. 35A.
Figure 48C:
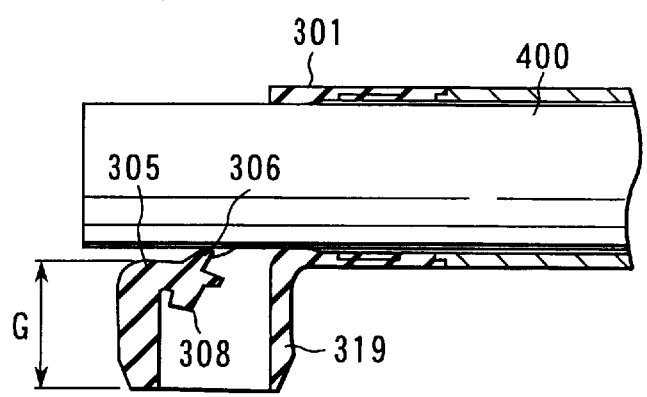
FIG. 48C is a sectional view showing a third actuation state when the endoscope is inserted into the endoscope dirt remover shown in FIG. 35A.
Figure 49:
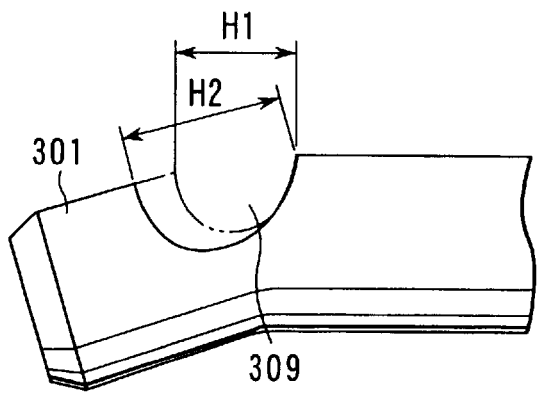
FIG. 49 is a view showing a modified state of an opening of the endoscope dirt remover shown in FIG. 35A.

As shown in FIGS. 48A to 48C, when the LG post 423 moves from the second stopper 312 of the guide portion 313 to the tip end direction, the first projection portion 306 positioned upwardly 306 positioned upwardly of the distal section 425 of the endoscope 400 is moved downwardly. At this time, the projection section 306 is pushed to the distal section 425 of the endoscope 400, and the arm 305 is deformed so as to be bent in the direction of the center axis O of the distal section 301 (refer to FIG. 48A). These changes will be described in more detail.

When the distal section 425 of the endoscope 400 moves in the tip end direction of the distal section 301, first, the projection section 306 is pressed in the tip end direction. Then, the force quantity is applied to the arm 305 that communicates with the projection section 306. The force quantity applied to the arm 305 pushes upwardly the tip end side of the opening section 309 in the tip end direction, and affects the deformation of the opening section 309 (deformation in the direction in which the width increases). As described above, when a sectional view vertical to the tip end center axis is taken at the center of the opening section 309, the thickness in the section is obtained as t2. On the other hand, the thickness upwardly at the tip end side of the retracting section 319 including the arm 305 is obtained as t1. A relationship between these thicknesses is t1>t2, therefore, the thickness t2-portion of the opening section 309 is positively deformed (of course, the thickness t1-portion is also deformed). Therefore, the entirety of the retracting section 319 is positively moved downwardly.

In addition, the projection section 306 is pushed in the tip end direction by the distal section 425 of the endoscope 400, and a contact angle when the projection section 306 comes into contact with the tip end of the endoscope 400 changes (in the direction in which an angle between the arm 305 and the projection section 306 increases). However, when this contact angle changes, a change in bending of the arm 305 starts at the same time. Thus, a change in contact angle is small, and the projection section 306 moves downwardly on the distal section 425 of the endoscope 400 while the retracting section 319 moves downwardly due to a change of the opening section 309.

Further, when the endoscope 400 is advanced, the arm 305 and the opening section 309 are further deformed, and the projection section 306 moves more downwardly of the distal section 425 of the endoscope 400. At this time, the contact angle of the projection section 306 changes as well. An angle between the arm 305 and the projection section 306 changes in the increasing direction while an angle between the restricting section 308 and the arm 305 changes in the decreasing (narrowing) direction (because the projection section 306 and the restricting section 308 are integrally structured). When the angle between the projection section 306 and the arm 305 changes to a predetermined degree, the restricting section 308 abuts against the internal wall of the top face at the tip end side of the opening section 309. Thus, the restricting section 308 hardly changes, and for this reason, the deformation in the increasing direction between the projection section 306 and the arm 305 hardly occurs (because the projection section 306 and the restricting section 308 are integrally structured). Therefore, an angle between the arm 305 and the projection section 306 is not set to 180 degrees (i.e. flat). Therefore, the arm 305 and protrusion section 306 can be prevented from being apparently planer. Namely, no contact with the distal section 425 of the endoscope 400 occurs on a large face. Abutment against the distal section 425 of the endoscope 400 occurs only at the narrow and long portion P1 of the projection section 306, and the top on the tip end face move downwardly (refer to FIG. 48B). Finally, the projection section 306 is positioned on the side face of the endoscope 400 (refer to FIG. 48B). The opening section 309 is deformed in the widthwise direction, and the distal section 425 of the endoscope 400 is protruded therebetween.

The inside of the insert section 501 of the endoscope guide tube 500 may be contaminated with blood or fluid. When the distal section 301 passes through the inside of the guide tube 500, the dirt adheres to the outside of the distal section 301. The first projection section 306 and the second protrusion section 307 are arranged inside of the distal section by the arm 305. Therefore, the dirt does not adhere to these projection sections 306 and 307. Therefore, even if an operation for exposing the distal section 425 of the above described endoscope 400 to the inside of the abdominal cavity is made, and the first projection portion 306 moves the distal section, no contamination occurs. Namely, when the endoscope 400 is inserted from the outside of the body to the inside of the abdominal cavity through the guide tube 500 together with the dirt remover 300, the inside of the abdominal cavity can be observed immediately without requiring a dirt removing operation described later.

Hereinafter, a state when the LG post 423 is set at a position indicated by solid line is referred to as an "endoscope observation state", a state when the LG post is set at a one-dotted chain position is referred to as a "dirt removal preparation state", and a state when the LG post is set at a position indicated by dashed line is referred to as a "guide tube insertion state".

As described above, the opening section 309 may be formed in a shape as shown in FIG. 37. Although the widths of the opening sections 309 are defined as F1 and F2, deformation occurs in a direction in which the width increases due to the operation described above, and the distal section 425 of the endoscope 400 can be protruded from the opening section 309 to the outside. The surgical operation under the endoscope is carried out in this state. In the insertion resistance R3 of the guide tube 500, the insertion through resistance R1 of the dirt removing section 300, and the though resistance R4 when the LG post 423 pass through the second stopper 312, the relationship is R1+R4>R3 (R3'). Therefore, when operation is carried out by only the endoscope 400, the LG post 323 does not pass through the second stopper 312 unintentionally (thus, dirt removal preparation state doesn't occur).

When the "endoscope observation state" is established, the retracting section 319 exists on the side face in the vicinity of the tip end of the endoscope 400. The retracting section 319 has a distance G between the tip end of the dirt remover 300 and the opening 309. Namely, the retracting section 319 is spaced with the distance G between the side face of the endoscope 400 and the distal section 301 of the dirt remover 300. Therefore, when the endoscope 400 is operated while the organ exists on the lower face of the endoscope 400, first, the tip end of the retracting section 319 comes into contact with the organ. This prevent the organ from coming into contact with the distal section 425 of the endoscope 400 unintentionally and the field of view from being contaminated. In addition, the retracting section 319 is made of an elastic element, this section is properly deformed due to the external force. Therefore, the retracting section is properly deformed when the section comes into contact with the organ, and thus, the organ is not damaged. Therefore, the projection section 306 exists in the retracting section 319. Thus, even if the retracting section 319 comes into contact with the organ, the projection section 306 is not contaminated by blood or fluid.

When tissues are treated by electronic knife or ultrasonic coagulation dissector and the like in the course of surgical operation under the endoscope, a smoke or mist occurs, and the field of view is contaminated. Alternatively, when the organ is discharged with pressure, the organ comes into contact with the distal section 425 of the endoscope 400 unintentionally, and the field of view may be contaminated. If the field of view is thus contaminated, and a clear endoscope image is obtained, disabling observation, the field of view is recovered in accordance with the following procedure. If the field of view is contaminated, the proximal end (or a camera head) of the main body section 426 of the endoscope 400 and the grip section 303 of the dirt remover 300 are gripped, and the LG post 423 is slid at the position indicating "dirt removing preparation state" in the guide section 313. When the LG post 423 is slid from the position indicated by solid line to the position indicated by single dotted chain line, the post passes through the second stopper 312. When the LG post 423 passes through this stopper 312, the force quantity of R4 described above is required. The force quantity of R4 is lower than that of R2 as described above, and thus, can be easily slid.

When the LG post 423 passes through the second stopper 312, first, the resistance R4 is felt. Then, the feeling of the resistance is eliminated, and the LG post 423 is arranged at the position indicated by single dotted chain line. This resistance can be felt at the frontal side, and thus, the "dirt removing preparation state" is found to have been established with sense (of course, the projection section appears in the endoscope image, and thus, this state can be visually identified).

Figure 50:
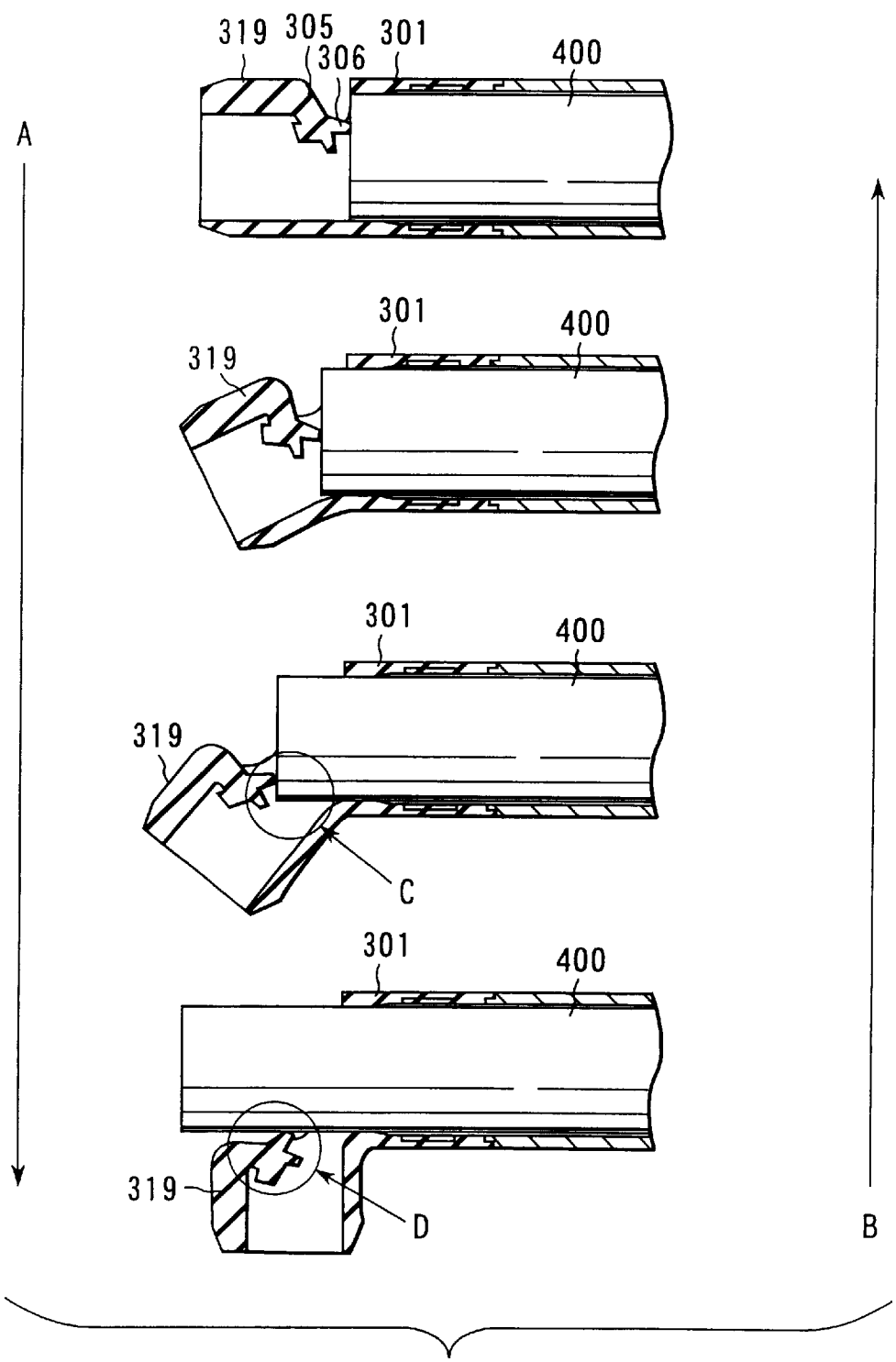
FIG. 50 is a sectional view showing a series of actuation states when the endoscope is inserted into the endoscope dirt remover shown in FIG. 35A.

At the same time of this operation, the distal section 425 of the endoscope 400 moves in the retracted direction from the state in which the distal section is protruded from the opening section 309. The retracting section 319 positioned in the vicinity of the distal section 425 of the endoscope 400 is restored in its original state in which the retracting section is positioned on the front face of the distal section 425 of the endoscope 400. In FIG. 50, a series of changes of the distal section 301 during these operations is indicated. The arrow A indicates a status change when the LG post 423 moves from the position indicated by solid line to the position indicated by single dotted chain line. That is, this arrow represents a state in which a relationship between the distal section 425 of the endoscope 400 and the distal section 301 of the dirt remover 300 has been changed from the "dirt removing preparation state" to the "endoscope observation state". On the other hand, the arrow B indicates a status change when the LG post 423 moves from the position indicated by single dotted chain line to the position indicated by solid line. That is, this arrow represents a state in which a relationship between the distal section 425 of the endoscope 400 and the distal section 301 of the dirt remover 300 has been changed from the "endoscope observation state" to the "dirt removing preparation state".

As described above, the distance $\gamma$ between the center axis O and P1 coincides with the distance $\alpha$ between the center axis O' of the endoscope 400 and the upper rim of the light face 427. Therefore, when the LG post 423 is arranged at a position indicated by single dotted chain line (dirt removing preparation state), the portion P1 of the first projection section 306 comes into contact with an upward part including the light face 427 of the distal section 425 of the endoscope 400. Next, in order to remove the dirt, the LG post 423 is moved to the position indicated by solid line (endoscope observation state). Then, the first projection section 306 moves downwardly from this position (position shifted from the center axis with the distance $\gamma$). Then, the projection section 306 moves downwardly in contact with the light face 427. This section wipes dirt at this section downwardly at the projection section 306. In this manner, the projection section 306 first abuts against a portion indicating the light face 427, and moves downwardly in abutment, whereby the dirt on the light face 427 can be removed (pushed downwardly). That is, obtaining diminished light due to the dirt adhered to the light face 427 is avoided and the light output is restored to its original light quantity. In addition, the distal section 425 of the endoscope 400 can be prevented from being too hot due to light being converted into heat as it strikes the dirt adhered to the light face 427.

When the LG post 423 moves to the position indicated by solid line, the opening section 309 is deformed as described above. Then, the deformed opening section 309 moves on the light face 427 and the lens face 428 at the tip end of the endoscope 400 while the first projection section 306 comes into contact with the deformed opening section. Due to this movement, the dirt existing on the faces 427 and 428 is moved downwardly and wiped (removed).

Now, movement of the first projection section 306 will be additionally described.

By referring to FIG. 48, a description has been given with respect to a change in tip end side from the dirt removing preparation state to the endoscope observation state. At the first projection section 306, the arm 305 is deformed, thereby reducing a change in contact angle when the projection section 306 moves downwardly on the light face 427 and the lens face 428. In more detail, if a predetermined force quantity is applied when the distal section 425 of the endoscope 400 moves to the first projection section 306 in the tip end direction, the force quantity is applied to the associated arm 305 as well. Then, the force quantity is transmitted from the arm 305 to the entirety of the retracting section 319. The thickness of the periphery of the opening section 309 is defined as t2, and is smaller than the thickness t1 at the upward part of the arm 305 or retracting section 319. Therefore, the deformation of the opening section 309 positively occurs, and then, the arm 305 is deformed. In this manner, the entirety of the retracting section 319 moves downwardly. The projection section 306 moves downwardly together with this movement. However, the arm 305 is properly deformed in accordance with the downward movement of the entirety of the retracting section 319 and, the force of compressing the projecting section 306 against the face is continuously generated by the elastic force of the arm 305. At this time, the angle between the arm 305 and the projection section 306 increases. Namely, the projection section moves downwardly in contact with the top of the face (427, 428). In this duration, the projection section can move while a change quantity of a contact angle between the face and the projection section is reduced to the possible minimum. In this manner, the projection section always comes into contact with the face at a contact angle in a predetermined range, and the dirt is wiped. Thus, so called chattering of the projection section 306 due to an unintentional angle does not occur, and non-uniform wiping can be prevented. In addition, the projection section 306 can be prevented from being partially floated relevant to the face due to the action of pressing the projection section 306 against the face due to the elastic force of the arm 305 (thus, non-uniform wiping can be prevented).

Now, a description of the restricting section 308 will be given here. As described above, although the angle between the arm 305 and the projection section 306 changed in an increasing direction, the restricting section 308 abuts against the inside wall of the top face at the tip end side of the opening section 309, whereby the angle between the arm 305 and the restricting section 308 is not changed into a predetermined angle or more. Namely, the angle between the arm 305 and the restricting section 308 is not set to 180 degrees, and thus, a "flat face" is not apparently formed. Therefore, a broad range of contact with the distal section 425 of the endoscope 400 does not occur at the periphery of the projection section 306 including the arm 305 (only a contact with the portion P1 side of the projection section 306 occurs). If a contact with a wide range of face occurs, it is difficult to apply force uniformly. Therefore, the top of the distal section 425 of the endoscope 400 is moved while a partially contacted portion is floated or waved, thus reducing an effect of removing the dirt (blurring or failure to wipe easily occurs). In this way, the angle is restricted at the restricting section 308, and no "face (flat face)" is apparently formed between the arm 305 and the projection section 306, thereby making it possible to bring into contact with the distal section 425 of the endoscope 400 only at the portion P1 side of the projection section 306. Therefore, the projection section 306 can be moved downwardly from the upward part of the distal section 425 of the endoscope 400 without reducing the effect of wiping the dirt.

Finally, the projection section 306 is positioned on the side face of the distal section 425 of the endoscope 400. When the projection section 306 moves from the state indicated by C shown in FIG. 50 to the state indicated by D, the dirt moved downwardly by the projection section 306 is flipped to the outside by the elastic force of the arm 305 and the projection section 306. Therefore, only a minute amount of the dirt adheres to the periphery of the projection section 306. By the above operation, the dirt of the blood or fluid on the face is wiped, the field of view is restored, and a clear endoscope image can be obtained.

Now, an effect of the inner diameter D' shown in FIG. 36B will be described here. When the inner diameter D' is smaller as compared with the outer diameter of the endoscope 400, the superior effect is achieved. When a large amount of dirt is adhered to the projection section 306 during surgical operation, and the dirt described above cannot be removed well by "flipping" it, the dirt remover 300 must be washed with water after removed from the inside of the body. After the remover has been lightly washed with water at the outside, if the endoscope 400 is inserted while water remains in the pipe section 302, when the endoscope passed through the inner diameter D', the outer diameter of the endoscope 400 is intimately inserted because the inner diameter D' is shorter. Namely, the water remaining in the tube path is prevented from dropping in the tip end direction of the endoscope 400 (so-called water drop is prevented).

Figure 55A:
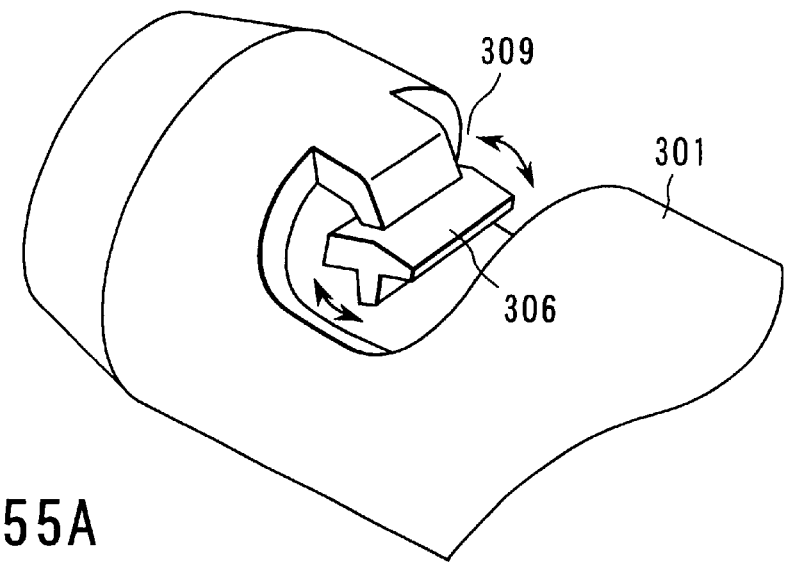
FIG. 55A is a perspective view showing a distal section of the endoscope dirt remover shown in FIG. 35A.
Figure 55B:
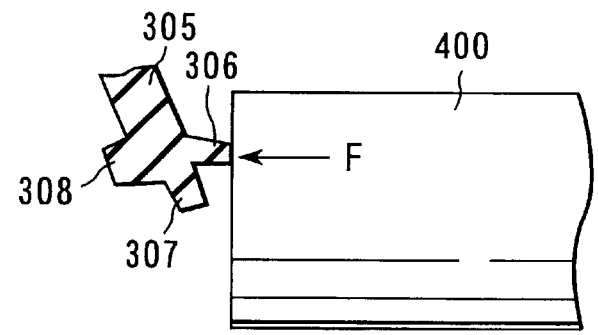
FIG. 55B and FIG. 55C are sectional views each showing a series of actuation states when the endoscope is inserted into the endoscope dirt remover shown in FIG. 35A.
Figure 55C:
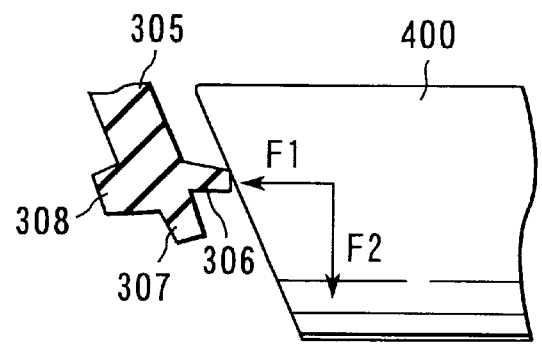

When the dirt cannot be fully wiped by this operation once, the dirt is removed by repeating this operation several times. That is, an operation of B→A→B shown in FIG. 55 is repeated (the position of the LG post 423 is changed from the position indicated by solid line→the position indicated by single dotted line→the position indicated by dashed line: see FIG. 46). As described above, since the dirt is flipped to the outside, the quantity of dirt is reduced by repeating this operation. Finally a clear endoscope image can be obtained. In addition, the quantity of dirt adhered to the projection section 306 is minute, the removed dirt does not adhere to the face again. Thus, the face is not contaminated.

Now, a description of the second projection section 307 will be given here.

Figure 51:
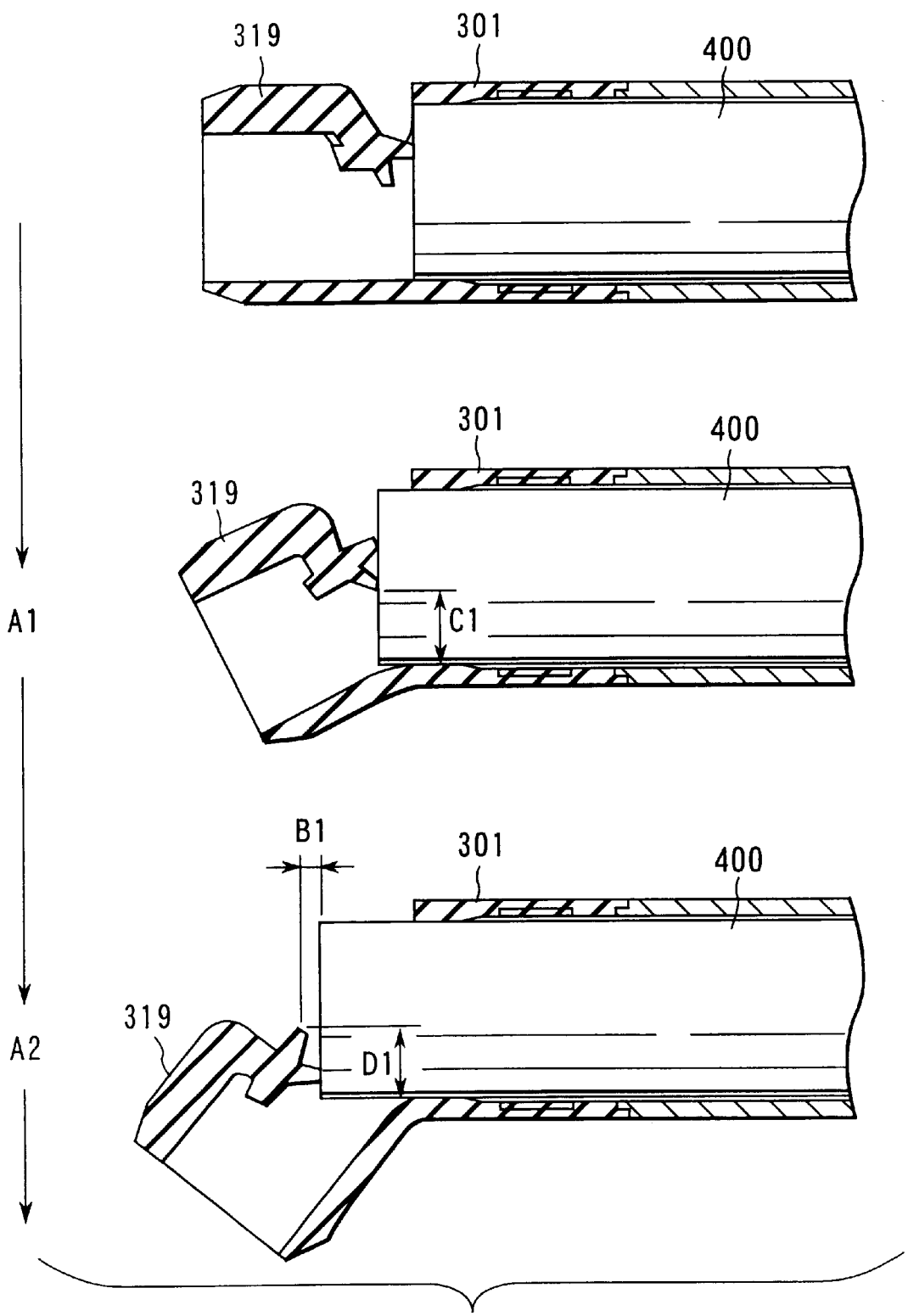
FIG. 51 is a sectional view showing a series of actuation states when the endoscope is inserted into the endoscope dirt remover shown in FIG. 35A.

The distal section 425 of the endoscope 400 may be wet or dried depending on its periphery. In general, a temperature of the inside of abdominal cavity is different from that of the distal section 425 of the endoscope 400 (at the first stage of surgical operation, the distal end 425 of the endoscope 400 is low in temperature). Then, condensation occurs on the surface of the distal section 425 of the endoscope 400, and so-called wet state is established. At this time, when dirt removing operation is carried out, the projection section 306 moves as described above. However, if surgical operation takes a long time, the distal section 425 of the endoscope 400 may be dried. The distal section 425 of the endoscope 400 has a function to emit the externally guided light to the inside of the abdominal cavity on the light face 427. Therefore, if the light is emitted from the light face 427 to the inside of abdominal cavity, a temperature at the periphery of the distal section may be higher than that of the inside of abdominal cavity, and may enters a dried state. When an operation for removing the dirt described above is made in this state, a frictional resistance between the first abutment section 306 and the distal end 425 of the endoscope 400 increases. That is, the first projection section 306 changes in a direction in which an angle relevant to the arm 305 decreases (narrows). If this change continues, the second projection section 307 comes into contact with the distal section 425 of the endoscope 400 as in the state A1 shown in FIG. 51. This position at which the second projection section 307 comes into contact with the distal section 425 of the endoscope 400 with the downward position of the endoscope as a reference is defined as a distance C1. Namely, the first projection section 306 and the second projection section 307 are in contact with the distal section 425 of the endoscope 400 at the same time. While the dirt removing state is changed to the state A1, only the first projection section 306 moves downwardly in contact with the distal section 425 of the endoscope 400.

Further, when the distal section 425 of the endoscope 400 is advanced in its tip end direction, both of the projection sections 306 and 307 changes from the state A1 to the state A2. While the state A1 is changed to the state A2, the first projection section 306 and the second projection section 307 move downwardly in contact with the distal section 425 of the endoscope 400. When the state A2 is established, the first projection section 306 starts leaving the distal section 425 of the endoscope 400 according to a downward movement of the retracting section 319 (refer to B1 of FIG. 51). This position at which the first projection section 306 starts leaving the distal section 425 of the endoscope 400 with the downward position of the endoscope 400 as a reference is defined as a distance D1.

Figure 52A:
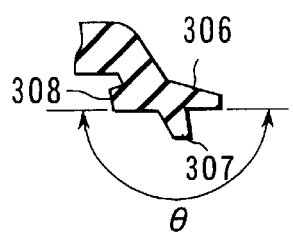
FIG. 52A is an enlarged sectional view showing a projection section.
Figure 52B:
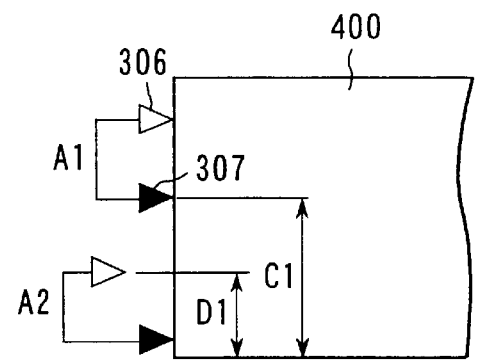
FIG. 52B is a view showing an abutment state of the endoscope against the projection section show in FIG. 52A.

When the distal section 425 of the endoscope 400 is further advanced from the state A2 to the tip end direction, only the second projection section 307 moves downwardly in contact with the distal section 425. Finally, the projection section 307 is positioned on the side face in the vicinity of the distal section 425 of the endoscope 400. A relationship between the distance C1 and the distance D1 is C1>D1. The second projection section 307 is designed to be thus positioned. FIG. 52B briefly represents the movement of the first projection section 306 and the second projection section 307. In the first operation, the first projection section 306 is distant from the distal section 425 of the endoscope 400 at the position of the distance D1, so that the dirt in this range cannot be wiped by the first projection section 306. However, the second projection section 307 can wipe a portion of distance D1 that cannot be wiped. By carrying out this operation several times, the dirt on the tip end face of the endoscope 400 can be reduced, and finally, a clear field of view can be restored. In addition, even when the first projection section 306 causes a change such that the angle relevant to the arm 305 decreases due to the frictional resistance on the tip end face of the endoscope 400, the face (flat face) formed by the first projection section 306 and the restricting section 308 can be prevent from coming into contact with the distal section 425 of the endoscope 400, due to the presence of the second projection section 307. That is, even if the wetting degree of the distal section 425 of the endoscope 400 changes, the projection section 306 can be properly brought into contact with the face.

Even in a state other than the state of the distal section 425 of the endoscope 400 described above, a behavior between the arm 305 and the projection 306 may occur. In such a case as well, the dirt at the downward position of the distal section 425 of the endoscope 400 can be wiped reliably.

On the other hand, a description will be given with respect to the mode of removing the dirt if a projection section whose sectional view is formed in an arc shape is provided as shown in FIG. 38.

The projection shape shown in FIG. 38 is all the same except that the projection shape and sectional view described above are formed in an arc shape. When a dirt removing operation is made, the portion P1 of a projection 322 comes into contact with the distal section 425 of the endoscope 400. Then, as in the projection section 306 described above, the projection 322 moved downwardly from the upward part of the distal end 425 of the endoscope 400. The projection section whose sectional view is formed in an arc shape is effective in dirt removing operation such that an angle between the arm 305 and the projection section decreases.

Figure 53A:
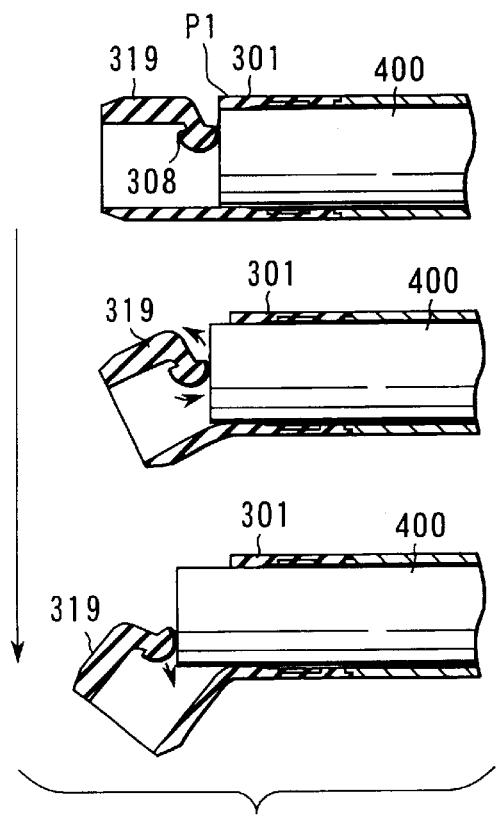
FIG. 53A is a sectional view showing a series of actuation states when the endoscope is inserted into the endoscope dirt remover shown in FIG. 35A.
Figure 53B:
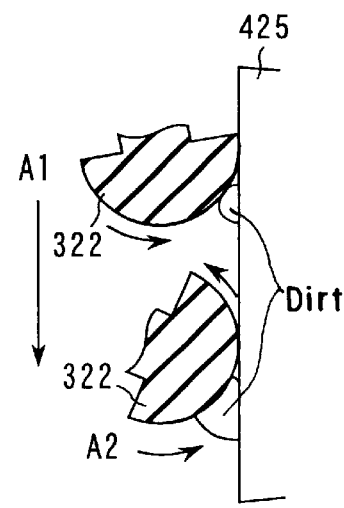
FIG. 53B is a view showing an abutment state of the endoscope against the projection section shown in FIG. 38A.

When the behavior as described above is shown, the projection section removes the dirt while the distal section of the endoscope 400 is moved downwardly from the upward part. When the distal section reaches a predetermined position, a portion coming into contact with the distal section on the projection section moves (refer to FIG. 53). Namely, the distal section of the endoscope rolls at the arc shaped section, and the projection section moves. At this time, the force is applied to the projection section in the direction of the distal section of the endoscope by the arm 305, and thus, the projection section is not floated. Therefore, the dirt moved from the upward part as well moves downwardly (refer to a change from state A1 to state A2 shown in FIG. 53B). From the foregoing, when the projection section whose sectional view is formed in an arc shape is used, even in a behavior such that an angle between the arm and projection section, the dirt can be removed by only one operation. In addition, the projection section always comes into contact with the distal section of the endoscope, there is no foaling portion, and thus, the dirt can be removed reliably.

Figure 54:
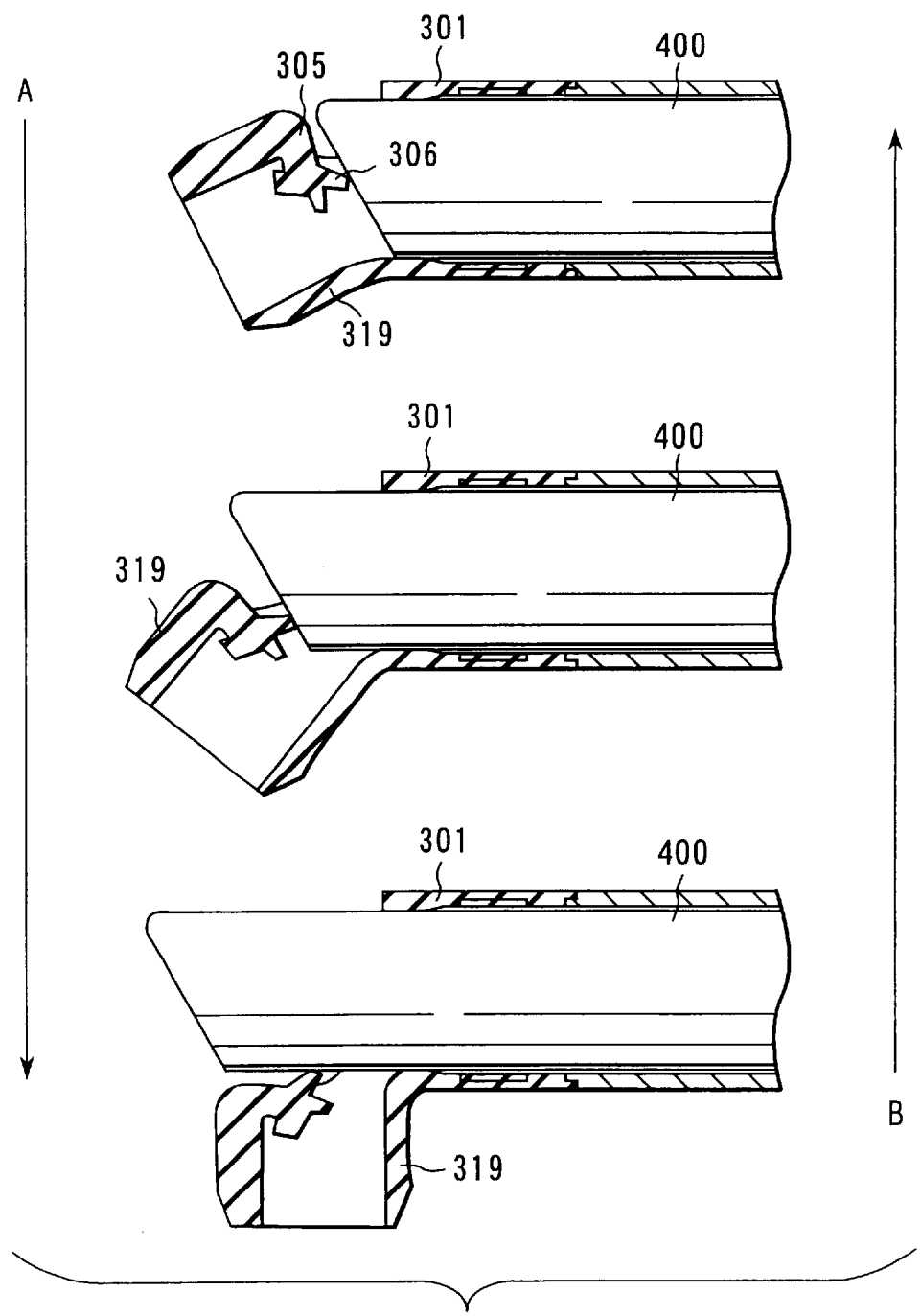
FIG. 54 is a sectional view showing a series of actuation states when the endoscope is inserted into the endoscope dirt remover shown in FIG. 35A.

When the sectional view is formed in the arc shape and the irregularities such as a projection 322' is provided on its surface, the dirt is efficiently wiped and moved in a downward direction at the tip end of its protrusion section, which is better. A description of removing the dirt using a so called direct viewing type of the endoscope distal section has been given. This invention can provide an effect of removing the dirt similarly even if the endoscope distal section is provided as a so called oblique viewing endoscope. FIG. 54 illustrates its behavior. As described above, the portion P of the projection section 306 comes into contact with the endoscope distal section. The portion P1 of the protrusion section 306 is spaced with the distance $\gamma$ from the center. This distance coincides with the distance $\alpha$ from the center including the direct viewing light face 427. A distance including the light face 427 from the center in the oblique viewing endoscope is defined as $\beta$. A relationship $\alpha<\beta$ is established, and thus, the projection section 306 reliably comes into contact with a upward position including the light face 427 of the endoscope. The projection section 306 makes operation for wiping the dirt downwardly from this position. In this manner, even an oblique viewing endoscope makes it possible to reliably wipe the dirt on the light face.

Dirt removing operation moves the tip end of the endoscope in distal direction or distal end direction (the LG post 423 moves from the position indicated by solid line to the position indicated by single dotted chain line or moves from the position indicated by single dotted chain line to the position indicated by solid line). Then, the angle between the arm 305 and the projection section 306 moves in an increasing direction. The force quantity applied to the perspective face differs depending on a direct viewing type. If an abutment portion is inclined, the downwardly applying force is increased in force quantity applied to the projection section 306 (refer to FIG. 55B). F, F1, and F2 are resistance forces (nominal force). The resistance force of F2 occurs when the tip end is inclined. Since the endoscope does not move downwardly, the projection section positively moves downwardly. That is, although the projection section 306 tends to change in the downward direction, the arm 305 is deformed in a bending direction. Thus, the position of the projection section 306 is not changed so drastically, and moves in the downward direction.

Figure 57:
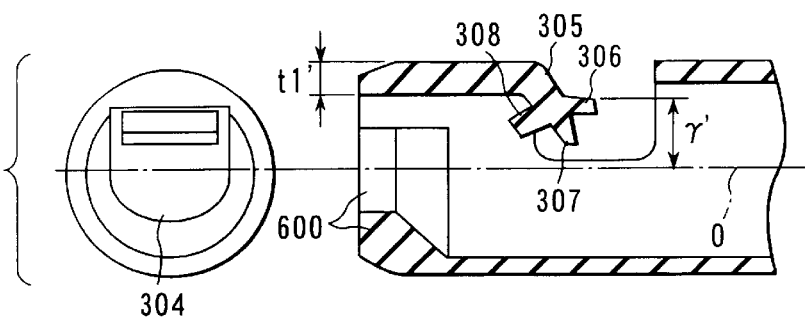
FIG. 57 is a sectional view according to a modified example of the retracting section of the distal section of the endoscope dirt remover shown in FIG. 35A.

If the oblique viewing endoscope rotates clockwise or counterclockwise relevant to the center axis, floating can occur on a face on which the tip end face of the oblique viewing endoscope and the projection section 306 comes into contact with each other. The tip end portion is properly deformed in the direction indicated by the arrow shown in FIG. 55A, thus making it possible for the projection section 306 to come into contact with the distal section of the endoscope without generating such floating. When t3<t4, the projection section 306 is more rigid than the arm 305. Thus, the arm 305 is likely to properly bent, and is easily deformed in accordance with the shape of the distal section. Now, a construction of the distal section will be described with respect to a case in which a change is made as shown in FIG. 57.

Only three differences from the previously described construction are that the tip end side of the retracting section is thick (600); a position of the first projection section 306 is shifted upwardly of the opening section; and a portion t1' is thicker than the previously descried construction. A distance γ' between the center axis O and the first projection section 306 is longer than the previously described distance γ. The other constituent elements are similar to those described previously. A behavior when the projection section is advanced and retracted relevant to the tip end of the endoscope in this configuration will be described here.

Figure 58:
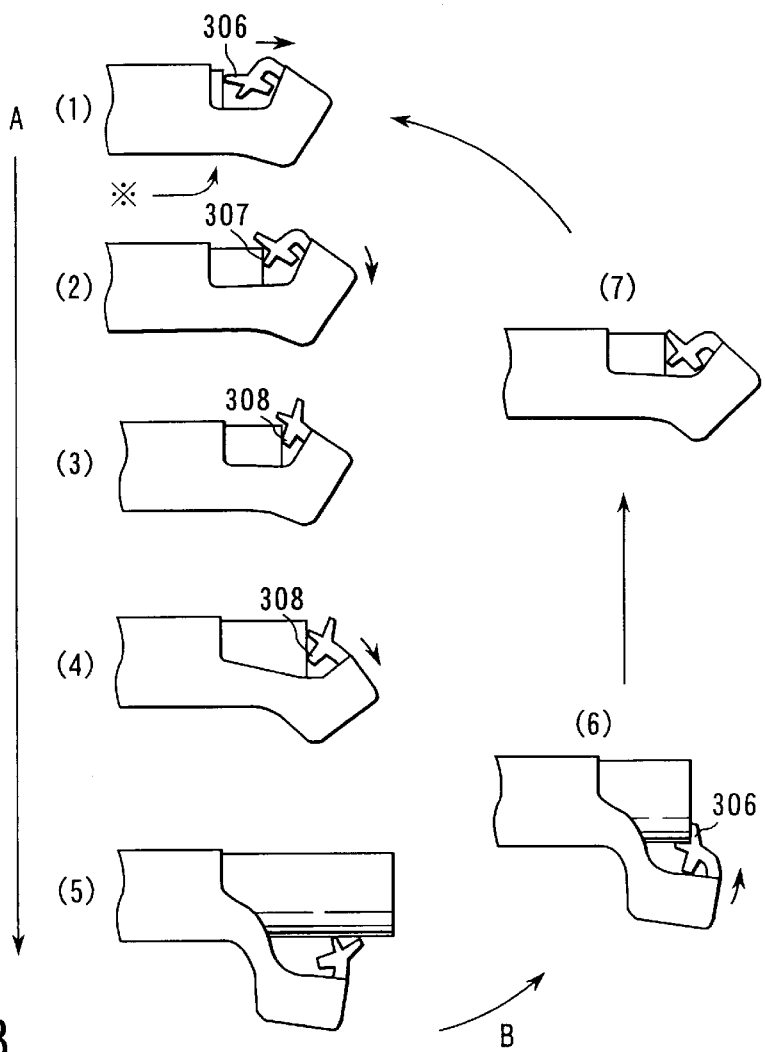
FIG. 58 is a view showing a series of actuation states when a direct viewing endoscope is inserted into the endoscope dirt remover shown in FIG. 57.

FIG. 58 shows a state in which the projection section 306 is advanced and retracted relevant to a direct viewing type endoscope. If the distal section is thicker, the strength of its periphery section is improved, and the cylindrical shape at the tip end side of the retracting section is hardly deformed by advancing and retracting operation. In addition, the behaviors of the projection section and the arm are different from those of the previously described construction in that a position at which the first projection section 306 abuts against the tip end face of the endoscope is changed to the distance γ' and in that t1' is thicker.

The movement in the direction the projection section is retracted relevant to the tip end of the endoscope is indicated by the arrow A of FIG. 58. When the projection section is retracted, the first projection section 306 first abuts against the upward part of the light face. Concurrently, the entire retracting section is deformed in the tip end direction. At the retracting section, a portion of t2 that is thinner than deformation of the arm (around the area marked with *) is positively deformed by the thickness of t1' and thickness 600 (FIG. 58 <1>). Then, the arm follows the behavior of the retracting section that is deformed downwardly while the arm is slightly deformed. In this manner, the projection section 306 moves upwardly, and the second projection section 307 abuts against the upward part of the light face (FIG. 58 <2>). When the projection section is further retracted, the second projection section 307 moves upwardly in accordance with the behaviors of the retracting section and the arm. Then, the restriction section 308 also abuts against the upward part of the light face (FIG. 58 <3>), and the restricting section 308 moves downwardly in abutment against the top of the tip end face of the endoscope (FIG. 58 <4>). At this time, the first and second projection sections do not come into contact with the tip end face. Namely, the restricting section 308 is obtained as a third projection capable of wiping the tip end face of the endoscope. Finally, these projection sections are protruded from the opening section to the outside, and are positioned at the side face of the endoscope. However, since the strength at the tip end side of the retracting section increases, the projection sections are restored in its original state. As a result, only the first projection section 306 and the second projection section 307 come into contact with the side face of the endoscope (FIG. 58 <5>).

On the other hand, when the projection section is advanced toward the endoscope, the first projection section 306 comes into contact with the tip end lower face of the endoscope (FIG. 58 <6>). When the projection section is further advanced, the second projection section 307 also comes into contact with the tip end lower face. Along with the behavior of the retracting section restoring in its original state, the first projection section and the second projection section move from the bottom face to the top face in contact with each other (FIG. 58 <7>), and the retracting section (and the projection section) are restored in their original states. At this time, the restricting section, i.e., the third projection does not come into contact with the tip end face. When the tip end face of the endoscope is contaminated, the projection section is thus advanced and retracted relevant to the tip end face of the endoscope, thereby making it possible to remove the dirt adhered onto the lens face. Although the dirt is adhered in the state of FIG. 58 <5> (in the observation state), if the projection section is advanced (as indicated by the arrow B), a predetermined degree of dirt can be removed at the first and second projection sections. Next, when the projection section is retracted (as indicated by the arrow A), the dirt remaining at the third projection (i.e., retracting section) is removed.

Figure 59:
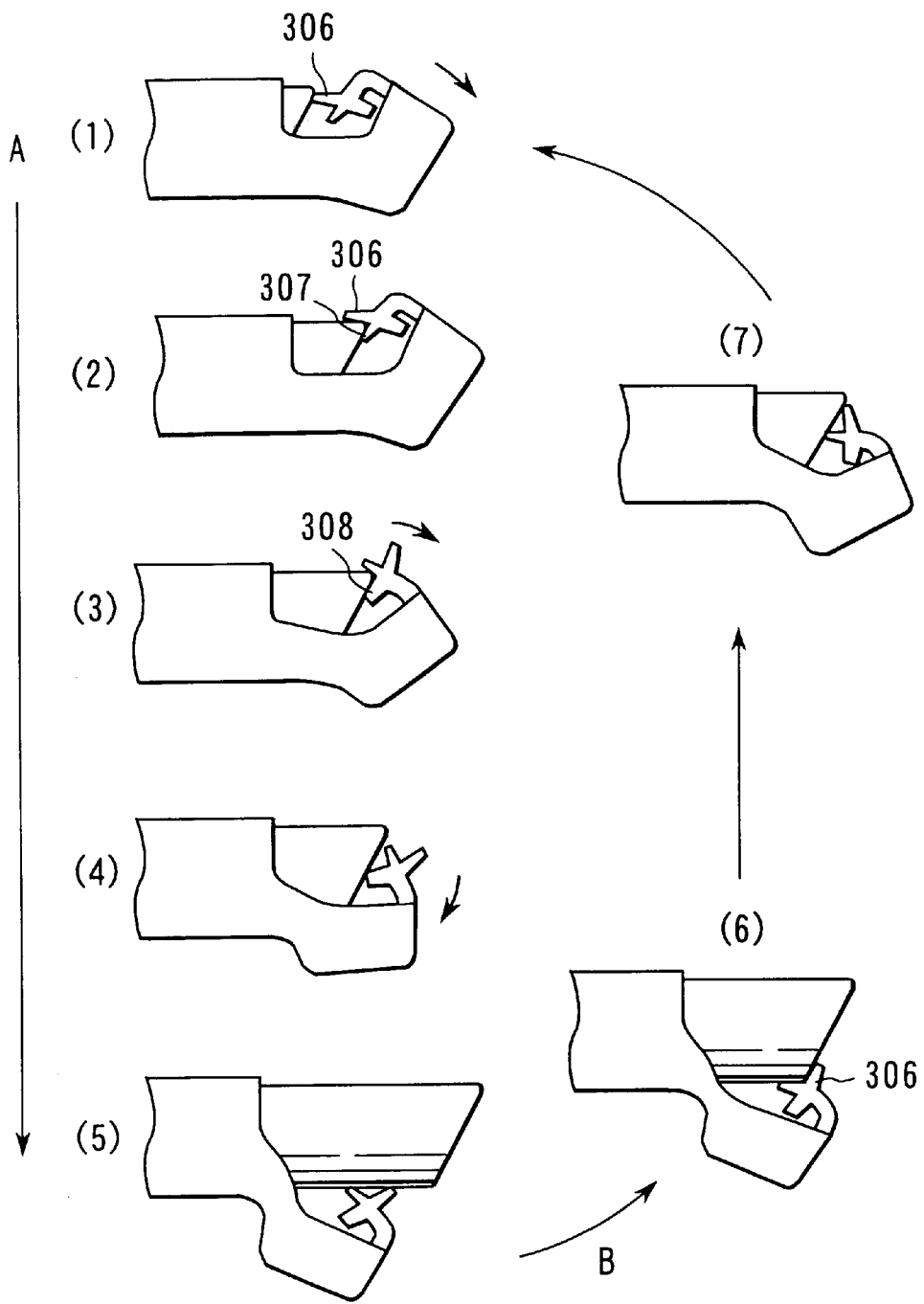
FIG. 59 is a view showing a series of actuation states when an oblique viewing endoscope is inserted into the endoscope dirt remover shown in FIG. 57.

Now, a case of use with a forward-oblique viewing endscope as shown in FIG. 59 will be described here. For the forward-oblique viewing endoscope, the behaviors are different from each other in FIG. 58 <2> only. The other elements are similar to those described previously. The behavior shown in FIG. 58 <2> sandwiches the tip end upper part of the endoscope between the projection section 306 and the projection section 307. If the projection section is retracted as is, the restricting section 308 being the third embodiment comes into contact with the tip end face, as described previously, and the dirt is wiped. Namely, the distance from the center O of the projection section 306 is γ', which is upper than the position of γ described previously. Thus, the projection section 306 easily moves to the upper section at the tip end of the endoscope. Next, pinching between this projection section and the projection section 307 is provided, whereby the projection section 307 returns due to a retracting operation, and the third projection 308 comes into contact with the top section of the tip end face.

Thus, the respective projection sections always remove the dirt in a unidirectional manner (the first and second projections remove the dirt when they are advanced and the third projection removes the dirt when it is retracted), thus making it possible to reliably remove the dirt with one operation. In addition, even if the tip end shapes of the endoscope are different from each other, the projection section presents similar behavior. Thus, the dirt can be constantly removed.

Therefore, even if the shape of the endoscope distal section is changed by the arm 305 and the projection section 306, the dirt can be properly removed from the top of the face, and a clear field of view can be restored. After the dirt has been successfully removed, the endoscope is set to enable observation, and surgical operation is continued. The endoscope during surgical operation is manipulated by gripping the proximal end or camera head. When an attempt is made to acquire the endoscope image after the endoscope is retracted in the direction of the outside of the body, the retracting section 319 at the tip end of the dirt remover 300 abuts against the edge of a trocal. An interference resistance when the retracting section 319 abuts against the rim of the trocal is defined as X. The interference resistance X is greater than each of the resistances (R1 to R4) among the guide tube 500, the endoscope 400, and the dirt remover 300, respectively. Therefore, if the interference resistance X occurs, a relationship among the resistance R3 between the guide tube 500 and the dirt remover 300, the resistance R4 (observed by the endoscope) between the dirt remover 300 and the endoscope 400, and the resistance R1 of the sealing section 318 is given below.

Figure 56:
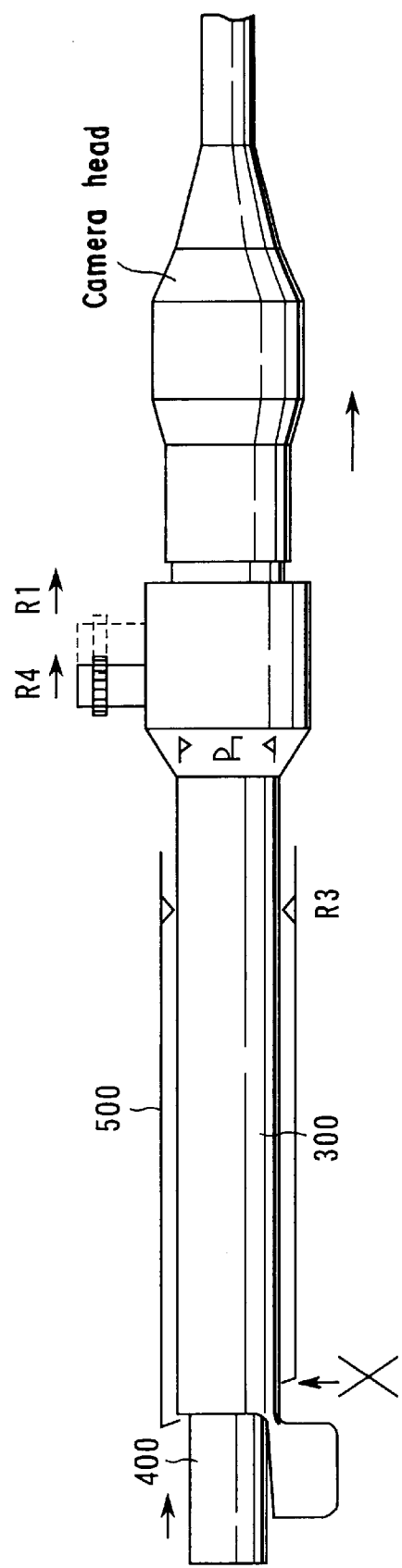
FIG. 56 is a view illustrating an insertion through resistance of the endoscope against the endoscope dirt remover.

X+R3>R1+R4 (refer to FIG. 56)

Therefore, only the endoscope 400 moves in the proximal end direction. Then, the LG post 423 moves from the position indicated by solid line to the position indicated by single dotted chain line. In this manner, the retracting section 319 is restored in its original state, and the interference resistance C is set to 0. Therefore, the fact that the endoscope 400 cannot be retracted any more in the direction of the outside of the body can be visually checked, and the image when the endoscope is retracted to the maximum can be obtained. If an attempt is made to remove the endoscope, the dirt remover 300 can be removed together with the endoscope by retracting the endoscope when R1+R2>R3. Thus, the endoscope 400 is removed while the dirt remover 300 remains in the guide tube 500, and the pneumoperitoneum gas in the abdominal cavity can be prevented from a leakage to the outside. In addition, the retracting section 319 is restored in its original position according to the removing operation of the endoscope 400. Thus, the breakage of the retracting section 319 can be prevented without interference with trocal. In this manner, this invention can provide always stable capability of removing the dirt even if the environment of the periphery at the distal section of the endoscope changes. The dirt can be removed at a proper position relevant to an endoscope with its different tip end shapes. Even if the endoscope is suddenly removed, interference between the retracting section and trocal distal section can be automatically eliminated. In addition, operation can be carried out without the external leakage of pneumoperitoneum gas in the abdominal cavity, thus improving the safety.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope dirt remover comprising:
    a tube through which an insert section of an endoscope having an objective lens is inserted;
    an elastic member coupled with said tube; and
    a wiper blade having a line-like shape coupled with said elastic member and being constructed to slide over and wipe said dirt of the objective lens, at least part of the wiper blade coming into contact with objective lens of the endoscope and slidingly moving on said objective lens, said elastic member being constructed to maintain said wipe blade in pressurized contact against said objective lens as it slides on said objective lens.

2. An endoscope dirt remover according to claim 1, wherein said wiper blade comprising a coupling section to be coupled with said elastic member and a wiping section which wipes the dit of the objective lens of said endoscope, said wiping section and said coupling section being different from each other in thickness.

3. An endoscope dirt remover according to claim 2, wherein said wiping section is thicker than aid coupling section.

4. An endoscope dirt remover according to claim 1, wherein said wiper blade has at least one projection, and when said wiper blade moves on the objective lens of said endoscope, the projection abuts against said objective lens.

5. An endoscope dirt remover according to claim 4, wherein said projection consists essentially of a porous member.

6. An endoscope dirt remover according to claim 5, wherein said porous member consists essentially of a water absorptive element.

7. An endoscope dirt remover according to claim 4, wherein said projection is independent of said wiper blade, and said projection is fixed to said wiper blade.

8. An endoscope dirt remover according to claim 7, wherein said projection is bonded to said wiper blade by adhesive, and said adhesive has elasticity even after dried.

9. An endoscope dirt remover according to claim 4, wherein said projection consists essentially of a soft element as compared with said wiper blade.

10. An endoscope dirt remover according to claim 4, wherein said projection comprises an edge, and when said wiper blade moves on the objective lens of said endoscope, the edge abuts against said objective lens.

11. An endoscope dirt remover according to claim 10, wherein a sectional view of said projection is formed in a shape selected from the group consisting of a substantially trapezoidal shape, a substantial rectangular shape, and a substantially triangular shape.

12. An endoscope dirt remover according to claim 4, wherein said projection is provided eccentrically from the center axis of said tube.

13. An endoscope dirt remover according to claim 1, wherein said elastic member is disposed inside of said tube.

14. An endoscope dirt remover according to claim 13, wherein said tube is formed as a trocar capable of inserting the inner needle into the inside thereof.

15. An endoscope dirt remover according to claim 14, wherein said wiper blade functions as a valve which opens or closes an inner hole of said trocar.

16. An endoscope dirt remover according to claim 15, wherein said wiper blade is inclined relevant to an axis in a longitudinal direction of said trocar and has at least one projection inclined relevant to an axis in a direction in which the wiper blade extends.

17. An endoscope dirt remover according to claim 14, wherein said trocar has a distal section and a proximal section other than said distal section, and said wiper blade is provided at said proximal section.

18. An endoscope dirt remover according to claim 15, wherein said guide tube comprises a proximal section into which said inner needle is inserted and a distal section at which said inner needle is projected, and said valve is provided at said proximal section side of said trocar.

19. An endoscope dirt remover according to claim 1, wherein said wiper blade is optically transparent.

20. An endoscope dirt remover according to claim 1, wherein said tube has a section to be curved.

21. An endoscope dirt remover according to claim 1, wherein said wiper blade has a face inclined relevant to the longitudinal axial direction of said tube.

22. An endoscope dirt remover comprising:
   a tube through which an insert section of an endoscope having an objective lens is inserted;
   an elastic member coupled with said tube; and
   a wiper blade coupled with said elastic member and wiping dirt of the objective lens, at least part of the wiper blade coming into contact with an objective lens of the endoscope and moving on said objective lens together with deformation of said elastic member, wherein said tube and said elastic member each are formed in a hollow shape and comprise respective first and second openings; the first opening of said tube is connected with the first opening of said elastic member; and said insert section of said endoscope is inserted from the second opening of said tube into said tube.

23. An endoscope dirt remover according to claim 22, wherein said wiper blade is formed in a strip shape, both ends of which are coupled with said elastic member.

24. An endoscope dirt remover according to claim 23, wherein said wiper blade has at least one projection, and when said wiper blade moves on the objective lens of said endoscope, the projection abuts against said objective lens.

25. An endoscope dirt remover according to claim 24, wherein said projection extends along a longitudinal direction of said wiper blade.

26. An endoscope dirt remover according to claim 25, wherein said projection is longer than the diameter of the objective lens of said endoscope.

27. An endoscope dirt remover according to claim 24, wherein said projection is provided eccentrically from the center axis of said tube.

28. An endoscope dirt remover according to claim 23, wherein two connecting portions to connect said wiper blade and said elastic element with each other are different from each other in elastic deformation quantity when the same load is applied.

29. An endoscope dirt remover according to claim 23, wherein the longitudinal direction of said wiper blade is parallel to an axis orthogonal to a center axis of said tube.

30. An endoscope dirt remover according to claim 22, wherein said wiper blade is formed in a T shape, each end of which is coupled with said elastic member.

31. An endoscope dirt remover according to claim 30, wherein said wiper blade has at least one projection, and when said wiper blade moves on the objective lens of said endoscope, the projection abuts against said objective lens.

32. An endoscope dirt remover according to claim 31, wherein said projection is provided eccentrically from the center axis of said tube.

33. An endoscope dirt remover according to claim 22, wherein said elastic member is formed in a hollow cylinder shape.

34. An endoscope dirt remover according to claim 33, wherein said wiper blade comprises one first projection, and when said wiper blade moved on the objective lens of said endoscope, the projection abuts against said objective lens.

35. An endoscope dirt remover according to claim 34, wherein said wiper blade comprises a second projection other than said first projection, and when said wiper blade moved on the objective lens of said endoscope, the second projection abuts against said objective lens.

36. An endoscope dirt remover according to claim 33, wherein the elastic member comprises a proximal section connected with the tube and a distal section positioned at the distal side of the second opening.

37. An endoscope dirt remover according to claim 36, wherein the distal section is thicker than the proximal section.

38. An endoscope dirt remover according to claim 36, wherein a third opening communicating the hollow inside of the elastic member with the outside of the elastic member is provided at the distal section, and the third opening is an observation window through which the outside can be observed by the objective lens of the endoscope.

39. An endoscope dirt remover according to claim 33, wherein said wiper blade extends from the side face of said elastic member to the inside of said elastic member in said second opening.

40. An endoscope dirt remover according to claim 33, wherein said wiper blade comprises a plurality of projections; and these projections come into contact with the objective lens of the endoscope when said wiper blade moves on the objective lens.

41. An endoscope dirt remover according to claim 40, wherein said plurality of projections are a first projection which moves in contact with the objective lens of the endoscope when the tube is advanced relative to the endoscope; and a second projection which moves in contact with the objective lens of the endoscope when the tube is retracted relative to the endoscope.

42. An endoscope dirt remover according to claim 40, wherein said projections are protruded from the second opening of the elastic member to the inside of the elastic member.

43. An endoscope dirt remover according to claim 40, wherein the elastic member comprises a proximal section connected with the tube and a distal section positioned at the distal side of the second opening.

44. An endoscope dirt remover according to claim 43, wherein the distal section is thicker than the proximal section.

45. An endoscope dirt remover according to claim 43, wherein a third opening communicating the hollow inside of the elastic member with the outside of the elastic member is provided at the distal section, and the third opening is an observation window through which the outside can be observed by the objective lens of the endoscope.

46. An endoscope dirt remover according to claim 22, further comprising: a grip section to be gripped to advance or retract said tube relevant to said insert section of said endoscope, the grip section being provided in the vicinity of said second opening of said tube.

47. An endoscope dirt remover according to claim 46, further comprising:
   a handle connected to said grip section.

48. An endoscope dirt remover according to claim 46, wherein said grip section comprises a recess, and a light guide connector provided at a frontal grip section of said endoscope is connected operatively in the recess.

49. An endoscope dirt remover according to claim 48, wherein said recess comprises a restriction projection section which restricts movement of said light guide connector.

50. An endoscope dirt remover according to claim 22, further comprising:
   a first flow path formed between an outer face of said insert section and an inner face of said tube when the insert section of said endoscope is inserted into said tube; and
   a fluid injection section formed at said tube, the fluid injection section having a second flow path for injecting fluid into said first flow path, wherein said elastic member has a wall for closing at least part of said second opening of the elastic member.

51. An endoscope dirt remover according to claim 22, wherein said tube is formed a trocar capable of inserting an inner needle into the inside thereof, and said inner needle is inserted through said second opening of said tube and protruded from said first opening of said elastic member.

52. An endoscope dirt remover according to claim 51, wherein said inner needle comprises a groove for retracting said wiper blade from a face forming a needle of said inner needle, and the groove is formed at a site of the inner needle protruded from the second opening of said elastic member.

53. An endoscope dirt remover comprising:
a tube through which an insert section of an endoscope having an objective lens is inserted;
an elastic member coupled with said tube; and
a wiper blade coupled with said elastic member and wiping dirt of the objective lens, at least part of the wiper blade coming into contact with an objective lens of the endoscope and moving on said objective lens together with deformation of said elastic member, wherein said tube and said elastic member each are formed in a hollow shape and have two first and second openings; the first opening of said tube is connected with the first opening of said elastic member; the second opening of said elastic member is smaller than the first opening of said elastic member and configures said wiper blade; and said insert section of said endoscope is inserted into said tube through the second opening of said tube.

54. An endoscope dirt remover according to claim 53, wherein said wiper blade comprises a projection formed at a rim of said second opening of said elastic member, and the projection is protruded inside of said elastic member.

55. An endoscope dirt remover according to claim 54, wherein the second opening of said elastic member is provided eccentrically from the center axis of said tube.

56. An endoscope dirt remover comprising:
a tube through which an insert section of an endoscope having an objective lens is inserted;
an elastic member coupled with said tube; and
a wiper blade coupled with said elastic member and wining dirt of the objective lens, at least part of the wiper blade coming into contact with an objective lens of the endoscope and moving on said objective lens together with deformation of said elastic member,
wherein said wiper blade has at least one projection, and when said wiper blade moves on the objective lens of said endoscope, the projection abuts against said objective lens, and wherein said projection comprises a curved face, and when said wiper blade moves on the objective lens of said endoscope, the curved face abuts against said objective lens.

* * * * *